(12) United States Patent
Hartz et al.

(10) Patent No.: US 9,932,320 B2
(45) Date of Patent: Apr. 3, 2018

(54) QUINOLINE-BASED KINASE INHIBITORS

(71) Applicant: BRISTOL-MYERS SQUIBB COMPANY, Princeton, NJ (US)

(72) Inventors: Richard A. Hartz, Middletown, CT (US); Vijay T. Ahuja, Princeton, NJ (US); John E. Macor, Washington Crossing, PA (US); Joanne J. Bronson, Durham, CT (US); Bireshwar Dasgupta, East Hampton, CT (US); Carolyn Diane Dzierba, Middletown, CT (US); Susheel Jethanand Nara, Mumbai (IN); Maheswaran Sivasamban Karatholuvhu, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/112,294

(22) PCT Filed: Jan. 23, 2015

(86) PCT No.: PCT/US2015/012649
§ 371 (c)(1),
(2) Date: Jul. 18, 2016

(87) PCT Pub. No.: WO2015/116492
PCT Pub. Date: Aug. 6, 2015

(65) Prior Publication Data
US 2016/0332985 A1 Nov. 17, 2016

Related U.S. Application Data

(60) Provisional application No. 61/934,152, filed on Jan. 31, 2014.

(51) Int. Cl.
| | |
|---|---|
| *C07D 401/14* | (2006.01) |
| *C07D 401/04* | (2006.01) |
| *C07D 215/12* | (2006.01) |
| *C07D 215/18* | (2006.01) |
| *C07D 413/04* | (2006.01) |
| *C07D 471/04* | (2006.01) |

(52) U.S. Cl.
CPC ......... *C07D 401/04* (2013.01); *C07D 215/12* (2013.01); *C07D 215/18* (2013.01); *C07D 401/14* (2013.01); *C07D 413/04* (2013.01); *C07D 471/04* (2013.01)

(58) Field of Classification Search
CPC .................................................. C07D 401/04
USPC ....................................................... 514/275
See application file for complete search history.

(56) References Cited

U.S. PATENT DOCUMENTS 6,919,335 B2    7/2005  Iwanowicz et al.

FOREIGN PATENT DOCUMENTS

| WO | WO2013134336    | *  | 7/2013 |
| WO | WO 2013/134336 A2 |   | 9/2013 |
| WO | WO 2016/053794 A1 |   | 4/2016 |

OTHER PUBLICATIONS

Aisen (Alzheimer's Research & Therapy (2009), vol. 1, pp. 1-6).*
Buonanno, A., "The neuregulin signaling pathway and schizophrenia: From genes to synapses and neural circuits", Brain Research Bulletin, vol. 83, pp. 122-131 (2010).
Conner, S.D. et al., "AAK1-Mediated µ2 Phosphorylation is Stimulated by Assembled Clathrin", Traffic, vol. 4, pp. 885-890 (2003).
Conner, S.D. et al., "Identification of an adaptor-associated kinase, AAK1, as a regulator of clathrin-mediated endocytosis", The Journal of Cell Biology, vol. 156, No. 5, pp. 921-929 (2002).
Greenwood, T.A. et al., "Analysis of 94 Candidate Genes and 12 Endophenotypes for Schizophrenia from the Consortium on the Genetics of Schizophrenia", Am. J. Psychiatry, vol. 168, No. 9, pp. 930-946 (2011).
Henderson, D.M. et al., "A Novel AAK1 Splice Variant Functions at Multiple Steps of the Endocytic Pathway", Molecular Biology of the Cell, vol. 18, pp. 2698-2706 (2007).
Jaaro-Peled, H. et al., "Review of Pathological Hallmarks of Schizophrenia: Comparison of Genetic Models with Patients and Nongenetic Models", Schizophrenia Bulletin, vol. 36, No. 2, pp. 301-313 (2010).
Jackson, A.P. et al., "Clathrin promotes incorporation of cargo into coated pits by activation of the AP2 adaptor µ2 kinase", The Journal of Cell Biology, vol. 163, No. 2, pp. 231-236 (2003).

(Continued)

*Primary Examiner* — Kendra D Carter
*Assistant Examiner* — Taina D Matos Negron
(74) *Attorney, Agent, or Firm* — Pamela A. Mingo

(57) ABSTRACT

The present disclosure is generally directed to compounds of formula (I) which can inhibit AAKI (adaptor associated kinase 1), compositions comprising such compounds, and methods for inhibiting AAKI.

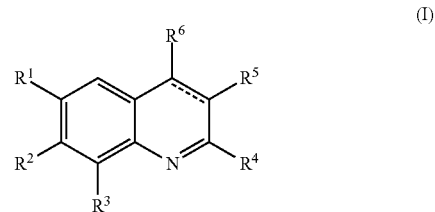

10 Claims, No Drawings

(56) References Cited

OTHER PUBLICATIONS

Kuai, L. et al., "AAK1 Identified as an Inhibitor of Neuregulin-1/ErbB4-Dependent Neurotrophic Factor Signaling Using Integrative Chemical Genomics and Proteomics", Chemistry & Biology, vol. 18, pp. 891-906 (2011).

Latourelle, J.C. et al., "Genomewide association study for onset age in Parkinson disease", BMC Medical Genetics, vol. 10 (2009), doi:10.1186/1471-2350-10-98.

Motley, A.M. et al., "Functional Analysis of AP-2 α and μ2 Subunits", Molecular Biology of the Cell, vol. 17, pp. 5298-5308 (2006).

Ricotta, D. et al., "Phosphorylation of the AP2 μ subunit by AAK1 mediates high affinity binding to membrane protein sorting signals", The Journal of Cell Biology, vol. 156, No. 5, pp. 791-795 (2002).

Wen, L. et al., "Neuregulin 1 regulates pyramidal neuron activity via ErbB4 in parvalbumin-positive interneurons", Proc. Natl. Acad. Sci., vol. 107, No. 3, pp. 1211-1216 (2010).

Watterson, S.H. et al., "Novel Inhibitors of IMPDH: A Highly Potent and Selective Quinolone-Based Series", Bioorganic & Medicinal Chemistry Letters, 13, pp. 543-546 (2003).

Database PubChem Compound [Online], NCBI; Aug. 20, 2012 (Aug. 20, 2012), Database accession No. CID60028612.

\* cited by examiner

QUINOLINE-BASED KINASE INHIBITORS

CROSS-REFERENCE TO RELATED APPLICATIONS

This application claims priority to Provisional Patent Application U.S. Ser. No. 61/934,152 filed Jan. 31, 2014, hereby incorporated by reference in its entirety.

The present disclosure is generally directed to compounds which can inhibit adaptor associated kinase 1 (AAK1), compositions comprising such compounds, and methods for inhibiting AAK1.

Adaptor associated kinase 1 (AAK1) is a member of the Ark1/Prk1 family of serine/threonine kinases. AAK1 mRNA exists in two splice forms termed short and long. The long form predominates and is highly expressed in brain and heart (Henderson and Conner, *Mol. Biol. Cell.* 2007, 18, 2698-2706). AAK1 is enriched in synaptosomal preparations and is co-localized with endocytic structures in cultured cells. AAK1 modulates clatherin coated endocytosis, a process that is important in synaptic vesicle recycling and receptor-mediated endocytosis. AAK1 associates with the AP2 complex, a hetero-tetramer which links receptor cargo to the clatherin coat. The binding of clatherin to AAK1 stimulates AAK1 kinase activity (Conner et. al., *Traffic* 2003, 4, 885-890; Jackson et. al., *J. Cell. Biol.* 2003, 163, 231-236). AAK1 phosphorylates the mu-2 subunit of AP-2, which promotes the binding of mu-2 to tyrosine containing sorting motifs on cargo receptors (Ricotta et. al., *J. Cell Bio.* 2002, 156, 791-795; Conner and Schmid, *J. Cell Bio.* 2002, 156, 921-929). Mu2 phosphorylation is not required for receptor uptake, but phosphorylation enhances the efficiency of internalization (Motely et. al., *Mol. Biol. Cell.* 2006, 17, 5298-5308).

AAK1 has been identified as an inhibitor of Neuregulin-1/ErbB4 signaling in PC12 cells. Loss of AAK1 expression through RNA interference mediated gene silencing or treatment with the kinase inhibitor K252a (which inhibits AAK1 kinase activity) results in the potentiation of Neuregulin-1 induced neurite outgrowth. These treatments result in increased expression of ErbB4 and accumulation of ErbB4 in or near the plasma membrane (Kuai et. al., *Chemistry and Biology* 2011, 18, 891-906). NRG1 and ErbB4 are putative schizophrenia susceptibility genes (Buonanno, *Brain Res. Bull.* 2010, 83, 122-131). SNPs in both genes have been associated with multiple schizophrenia endophenotypes (Greenwood et. al., *Am. J. Psychiatry* 2011, 168, 930-946). Neuregulin 1 and ErbB4 KO mouse models have shown schizophrenia relevant morphological changes and behavioral phenotypes (Jaaro-Peled et. al., *Schizophrenia Bulletin* 2010, 36, 301-313; Wen et. al., Proc. Natl. Acad. Sci. USA. 2010, 107, 1211-1216). In addition, a single nucleotide polymorphism in an intron of the AAK1 gene has been associated with the age of onset of Parkinson's disease (Latourelle et. al., *BMC Med. Genet.* 2009, 10, 98). These results suggest that inhibition of AAK1 activity may have utility in the treatment of schizophrenia, cognitive deficits in schizophrenia, Parkinson's disease, neuropathic pain, bipolar disorder, and Alzheimer's disease.

In its first aspect the present disclosure provides a compound of formula (I)

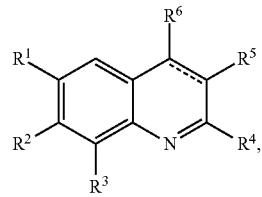

(I)

or a pharmaceutically acceptable salt thereof, wherein:

$R^1$ is selected from imidazopyridazine, isoquinolinyl, oxazolyl, pyridinyl, pyrimidinyl, pyrrolopyridinyl, and quinolinyl, wherein each ring is optionally substituted with $C_1$-$C_3$acylamino, $C_1$-$C_3$alkyl, amino, $C_1$-$C_3$alkoxy, $C_3$-$C_6$cycloalkyl, $C_3$-$C_6$cycloalkylamino, $C_1$-$C_3$dialkylamino, —$NHCO_2(C_1$-$C_3)$alkyl, and phenylcarbonylamino optionally substituted with a halo or haloalkyl group;

$R^2$ is selected from hydrogen, $C_1$-$C_3$alkoxy, and $C_1$-$C_3$alkyl;

$R^3$ is selected from hydrogen, $C_1$-$C_3$alkoxy, $C_1$-$C_3$alkyl, cyano, and halo;

$R^4$ is selected from $C_3$-$C_6$alkyl optionally substituted with one group selected from amino, haloalkyloxy, hydroxy and oxo; and $C_3$-$C_6$cycloalkyl$C_1$-$C_3$alkyl optionally substituted with amino;

$R^5$ is selected from hydrogen, $C_1$-$C_6$alkyl, amido, cyano, and halo;

when ⇌ is a double bond, $R^6$ is selected from hydrogen, $C_1$-$C_6$alkoxy, $C_1$-$C_6$alkyl, amido, cyano, $C_1$-$C_6$dialkylamino, halo, hydroxy, and a five-membered heteroaromatic ring; and when ⇌ is a single bond, $R^6$ is =S.

In a first embodiment of the first aspect the present disclosure provides a compound of formula (I) wherein $R^3$ is halo.

In a second embodiment of the first aspect the present disclosure provides a compound of formula (I), or a pharmaceutically acceptable salt thereof, wherein wherein $R^3$ is hydrogen. In a third embodiment $R^2$ is $C_1$-$C_3$alkoxy.

In a fourth embodiment of the first aspect the present disclosure provides a compound of formula (I), or a pharmaceutically acceptable salt thereof, wherein wherein $R^3$ is hydrogen and $R^2$ is hydrogen. In a fifth embodiment $R^5$ is selected from $C_1$-$C_6$alkyl, amido, cyano, and halo.

In a sixth embodiment of the first aspect the present disclosure provides a compound of formula (I), or a pharmaceutically acceptable salt thereof, wherein $R^3$ is hydrogen, $R^2$ is hydrogen, and $R^5$ is hydrogen.

In a second aspect the present disclosure provides composition comprising a pharmaceutically acceptable amount of a compound of formula (I), or a pharmaceutically acceptable salt thereof, and a pharmaceutically acceptable carrier.

In a third aspect the present disclosure provides a method of inhibiting adaptor associated kinase 1 (AAK1) activity, comprising contacting AAK1 with a compound of formula (I), or a pharmaceutically acceptable salt thereof.

In a fourth aspect the present disclosure provides a method for treating or managing a disease or a disorder mediated by AAK1 activity, the method comprising administering to a patient in need thereof a therapeutically effective amount of a compound of formula (I), or a pharmaceutically acceptable salt thereof. In a first embodiment of the fourth aspect the disease or disorder is selected from Alzheimer's disease, bipolar disorder, pain, Parkinson's disease, and schizophrenia. In a second embodiment of the fourth aspect the pain is neuropathic pain. In a third embodiment of the fourth aspect the neuropathic pain is fibromyalgia or peripheral neuropathy.

Other aspects of the present disclosure may include suitable combinations of embodiments disclosed herein.

Yet other aspects and embodiments may be found in the description provided herein.

This disclosure is based, in part, on the discovery that AAK1 knockout mice exhibit a high resistance to pain. That discovery prompted research that ultimately led to the discovery of AAK1 inhibitors, compositions comprising them, and methods of their use.

The description of the present disclosure herein should be construed in congruity with the laws and principals of chemical bonding. In some instances it may be necessary to remove a hydrogen atom in order to accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule. For example, when n is 2, each of the two $R^6$ groups may be the same or different.

As used in the present specification, the following terms have the meanings indicated:

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

In some instances, the number of carbon atoms in any particular group is denoted before the recitation of the group. For example, the term "$C_{1-6}$ alkyl" denotes an alkyl group containing one to six carbon atoms. Where these designations exist they supercede all other definitions contained herein.

The term "acylamino," as used herein, refers to —NHC(O)R wherein R is an alkyl group.

The term "alkoxy," as used herein, refers to an alkyl group attached to the parent molecular moiety through an oxygen atom.

The term "alkyl," as used herein, refers to a group derived from a straight or branched chain saturated hydrocarbon.

The term "amido," as used herein, refers to —C(O)NH$_2$.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having zero heteroatoms. Representative examples of cycloalkyl groups include, but are not limited to, cyclopropyl, cyclopentyl, and cyclohexyl.

The term "cycloalkylalkyl," as used herein, refers to a cycloalkyl group attached to the parent molecular moiety through an alkyl group.

The term "cycloalkylamino," as used herein, refers to —NHR wherein R is a cycloalkyl group.

The term "dialkylamino," as used herein, refers to NR$_2$, wherein each R is an alkyl group. The two alkyl groups are the same or different.

The term "five-membered heteroaromatic ring," as used herein, refers to a ring containing five members wherein the ring contains at least one heteroatom. It should be understood that the term encompasses only those rings that are stable and known to one of skill in the art.

The term "halo," as used herein, refers to Br, Cl, F, and/or I.

The term "haloalkoxy," as used herein, refers to a haloalkyl group attached to the parent molecular moiety through an oxygen atom.

The term "haloalkyl," as used herein, refers to an alkyl group substituted by one, two, three, or four halogen atoms.

The term "hydroxy," as used herein, refers to —OH.

The term "oxo," as used herein, refers to =O.

The term "phenylcarbonylamino," as used herein, refers to —NHC(O)-Ph, wherein Ph is a phenyl group.

Asymmetric centers may exist in the compounds of the present disclosure. It should be understood that the disclosure encompasses all stereochemical isomeric forms, or mixtures thereof, which possess the ability to inhibit AAK1. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of formula (I), and pharmaceutically acceptable enantiomers, diastereomers, and salts thereof. Similarly, references to intermediates are meant to embrace their salts where the context so permits.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

One embodiment of this disclosure encompasses methods of inhibiting adaptor associated kinase 1 (AAK1), both in vitro and in vivo, which comprise contacting AAK1 with a compound of formula I or a pharmaceutically acceptable salt thereof.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. Unless otherwise indicated, a "therapeutically effective amount" of a compound is an amount sufficient to provide a therapeutic benefit in the treatment or management of a disease or condition, or to delay or minimize one or more symptoms associated with the disease or condition. The term "therapeutically effective amount" can encompass an amount that improves overall therapy, reduces or avoids symptoms or causes of a disease or condition, or enhances the therapeutic efficacy of another therapeutic agent.

The term "therapeutically effective amount," as used herein, refers to an amount of a compound or compounds sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, that provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Compounds of the disclosure may be administered in combination with one or more additional therapeutic or prophylactic agents. For example, when used for the treatment of pain, possible additional agents include immunosuppressive agents, anti-inflammatory agents, and/or other agents used in the treatment of pain.

Immunosuppressants suitable for use in the methods and compositions of this disclosure include those known in the art. Examples include aminopterin, azathioprine, cyclosporin A, D-penicillamine, gold salts, hydroxychloroquine, leflunomide, methotrexate, minocycline, rapamycin, sulfasalazine, tacrolimus (FK506), and pharmaceutically acceptable salts thereof. A particular immunosuppressant is methotrexate.

Additional examples of immunosuppressants include anti-TNF antibodies, such as adalimumab, certolizumab pegol, etanercept, and infliximab. Others include interleukin-1 blockers, such as anakinra Others include anti-B cell (CD20) antibodies, such as rituximab. Others include T cell activation blockers, such as abatacept.

Other immunosuppressants include inosine monophosphate dehydrogenase inhibitors, such as mycophenolate mofetil (CellCept®) and mycophenolic acid (Myfortic®).

Anti-inflammatory drugs suitable for use in the methods and compositions of this disclosure include those known in the art. Examples include glucocorticoids and NSAIDs. Examples of glucocorticoids include aldosterone, beclometasone, betamethasone, cortisone, deoxycorticosterone, dexamethasone, fluorocortisones, hydrocortisone, methylprednisolone, prednisolone, prednisone, triamcinolone, and pharmaceutically acceptable salts thereof.

Examples of NSAID include salicylates (e.g., aspirin, amoxiprin, benorilate, choline magnesium salicylate, diflunisal, faislamine, methyl salicylate, magnesium salicylate, salicyl salicylate, and pharmaceutically acceptable salts thereof), arylalkanoic acids (e.g., diclofenac, aceclofenac, acemetacin, bromfenac, etodolac, indometacin, nabumetone, sulindac, tolmetin, and pharmaceutically acceptable salts thereof), arylpropionic acids (e.g., ibuprofen, carprofen, fenbufen, fenoprofen, flurbiprofen, ketoprofen, ketorolac, loxoprofen, naproxen, oxaprozin, tiaprofenic acid, suprofen, and pharmaceutically acceptable salts thereof), arylanthranilic acids (e.g., meclofenamic acid, mefenamic acid, and pharmaceutically acceptable salts thereof), pyrazolidine derivatives (e.g., azapropazone, metamizole, oxyphenbutazone, phenylbutazone, sulfinprazone, and pharmaceutically acceptable salts thereof), oxicams (e.g., lornoxicam, meloxicam, piroxicam, tenoxicam, and pharmaceutically acceptable salts thereof), COX-2 inhibitors (e.g., celecoxib, etoricoxib, lumiracoxib, parecoxib, rofecoxib, valdecoxib, and pharmaceutically acceptable salts thereof), and sulphonanilides (e.g., nimesulide and pharmaceutically acceptable salts thereof).

Other agents used in the treatment of pain (including but not limited to neuropathic and inflammatory pain) include, but are not limited to, agents such as pregabalin, lidocaine, duloxetine, gabapentin, carbamazepine, capsaicin, and other serotonin/norepinephrine/dopamine reuptake inhibitors, and opiates (such as oxycontin, morphine, and codeine).

In the treatment of pain caused by a known disease or condition, such as diabetes, infection (e.g., herpes zoster or HIV infection), or cancer, compounds of the disclosure may be administered in combination with one or more additional therapeutic or prophylactic agents directed at the underlying disease or condition. For example, when used to treat diabetic neuropathy, compounds of the disclosure may be administered in combination with one or more anti-diabetic agents, anti-hyperglycemic agents, hypolipidemic/lipid lowering agents, anti-obesity agents, anti-hypertensive agents and appetite suppressants. Examples of anti-diabetic agents include biguanides (e.g., metformin, phenformin), glucosidase inhibitors (e.g., acarbose, miglitol), insulins (including insulin secretagogues and insulin sensitizers), meglitinides (e.g., repaglinide), sulfonylureas (e.g., glimepiride, glyburide, gliclazide, chlorpropamide, and glipizide), biguanide/glyburide combinations (e.g., Glucovance), thiazolidinediones (e.g., troglitazone, rosiglitazone, and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, dipeptidyl peptidase IV (DPP4) inhibitors, and sodium-glucose co-transporter 2 (SGLT2) inhibitors (e.g., dapagliflozin, canagliflozin, and LX-4211).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

Unless otherwise indicated, the terms "manage," "managing", and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

This disclosure is intended to encompass compounds having Formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: Ph for phenyl; OAc for acetate; DME for 1,2-dimethoxyethane; DMF for N,N-dimethylformamide; n-BuLi for n-butyl lithium; AcOH for acetic acid; THF for tetrahydrofuran; Me for methyl; DMAc or DMAC for dimethylacetamide; AIBN for azobisisobutyronitrile; TosMIC for tosylmethyl isocyanide; MeOH for methanol; EtOH for ethanol; LDA for lithium diisopropylamide; TBTU for O-benzotriazol-1-yl-1,1,3,3-tetramethyluronium tetrafluoroborate; DIAD for diisopropyl azodicarboxylate; MeCN or ACN for acetonitrile; Et for ethyl; NBS for N-bromosuccinimide; PPA for polyphosphoric acid; TEA or $Et_3N$ for triethylamine; DCM for dichloromethane; DCE for 1,2-dichloroethane; DIEA for diisopropylethylamine; EtOAc for ethyl acetate; MeOD for $CD_3OD$; TFA for trifluoroacetic acid; h for hours; DEA for diethylamine; R.T. or RT for room temperature or retention time (context will dictate); DPPF for 1,1'-bis(diphenylphosphanyl)ferrocene; EDC for 1-(3-dimethylaminopropyl)-3-ethylcarbodiimide hydrochloride; HOBT for hydroxybenzotriazole; and DMAP for N,N-dimethylaminopyridine.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present disclosure may be prepared using the reactions and techniques described in this section as well as other synthetic methods known to those of ordinary skill in the art. The reactions are performed in solvents appropriate to the reagents and materials employed and suitable for the transformation being affected. Also, in the description of the synthetic methods described below, it is to be understood that all proposed reaction conditions, including choice of solvents, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula 8, wherein $R^1$, $R^2$, and $R^3$ are as defined in formula (I), can be prepared as described in Scheme 1. Treatment of ethyl acetoacetate with sodium hydride and n-butyllithium in a polar aprotic solvent such as THF followed by the addition of 1-iodo-2-methylpropane (3) affords methyl 6-methyl-3-oxoheptanoate (4). It is recognized by one skilled in the art that a variety of alkyl halides, in addition to 1-iodo-2-methylpropane, may be reacted with 2 to furnish compounds with various alkyl groups in place of the 3-methylbutyl substituent in 4. Compound 4 is condensed with anilines of formula 5 in the presence of an acid such as acetic acid and 4 Å molecular sieves in a solvent such as toluene at temperatures ranging from 60° C. to 120° C. to furnish compounds of formula 6. Compounds of formula 6 are heated at 250° C. in phenyl ether resulting in cyclization to form compounds of formula 7. Coupling of compounds of formula 7 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 8. The coupling reaction is carried out by heating the reaction mixture using standard laboratory methods or by heating the reaction mixture in a microwave.

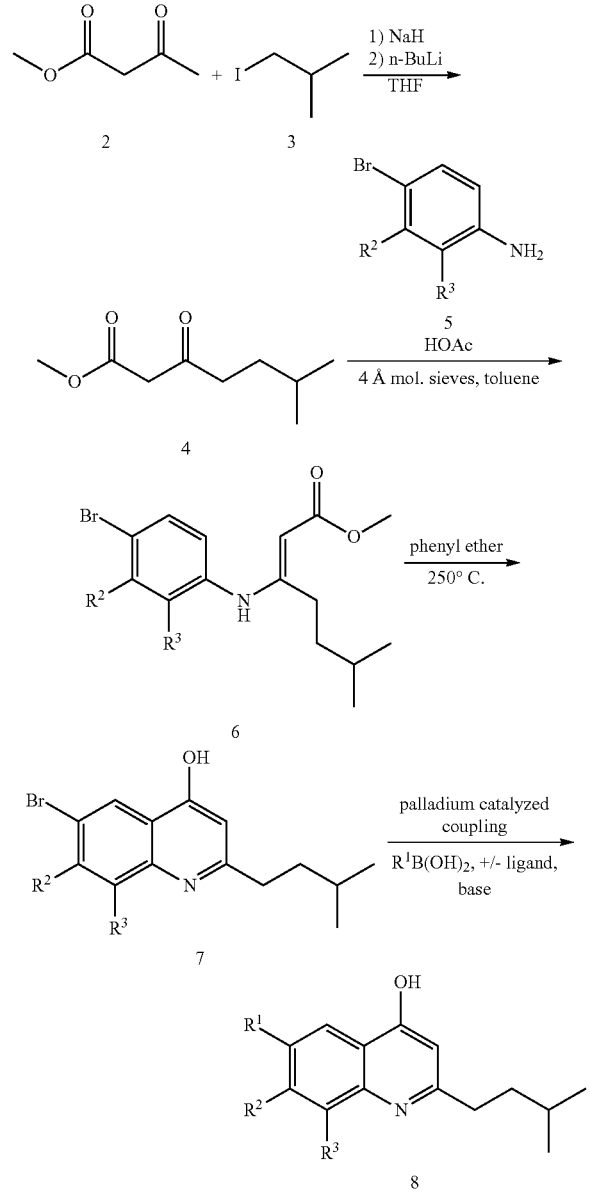

Scheme 1

Using the methods described in Scheme 2, compounds of formula 9, wherein $R^1$, $R^2$, and $R^3$ are as defined in formula (I), can be prepared from compounds of formula 8 by treating the later with a base such as sodium hydride, potassium carbonate, potassium hydroxide or sodium hydroxide in a solvent such as DMF or THF. Subsequent addition of a methylating agent such as iodomethane or dimethylsulfate and stirring the reaction mixture at temperatures ranging from 0 to 100° C. furnishes compounds of formula 9. Compounds of formula 10, wherein R', R², and R³ are as defined in formula (I), can be prepared from compounds of formula 8 by stirring the later in the presence of phosphorus tribromide in a solvent such as DMF. Alternatively, this reaction can be carried out by heating compounds of formula 8 in the presence of phosphorus oxybromide and catalytic DMF in a solvent such as dichloroethane at temperatures ranging from 50 to 100° C. to afford compounds of formula 10.

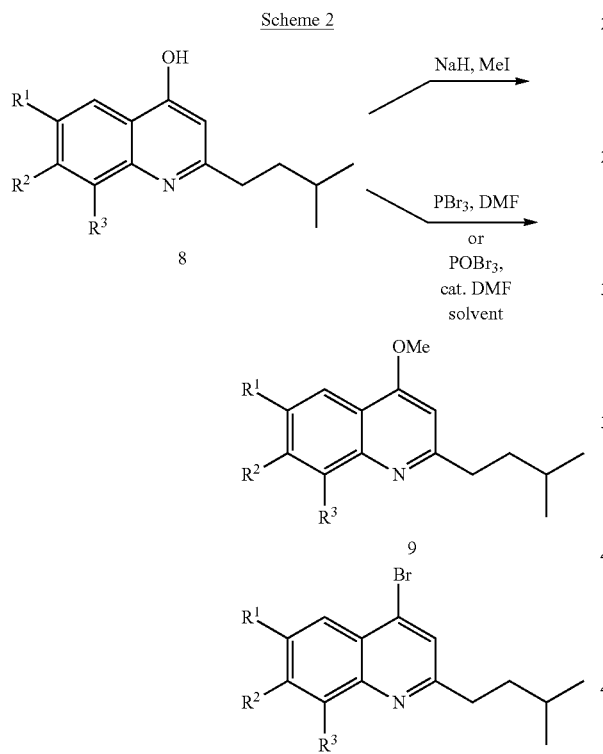

Using the methods described in Scheme 3, compounds of formula 11, wherein R¹, R², and R³ are as defined in formula (I), can be prepared from compounds of formula 10 by treating the later with palladium on carbon in a solvent such as methanol or ethanol and stirring the resulting mixture under a hydrogen atmosphere. Compounds of formula 12, wherein R¹, R², and R³ are as defined in formula (I), can be prepared from compounds of formula 10 by stirring the later in the presence of a palladium catalyst and appropriate ligand, if necessary, along with zinc cyanide in a solvent such as DMF, DME, or DMAC in the presence or absence of water. The reaction is carried out at temperatures ranging from 70 to 150° C. to furnish compounds of formula 12. The coupling reaction is carried out by heating the reaction mixture using standard laboratory methods or by heating the reaction mixture in a microwave.

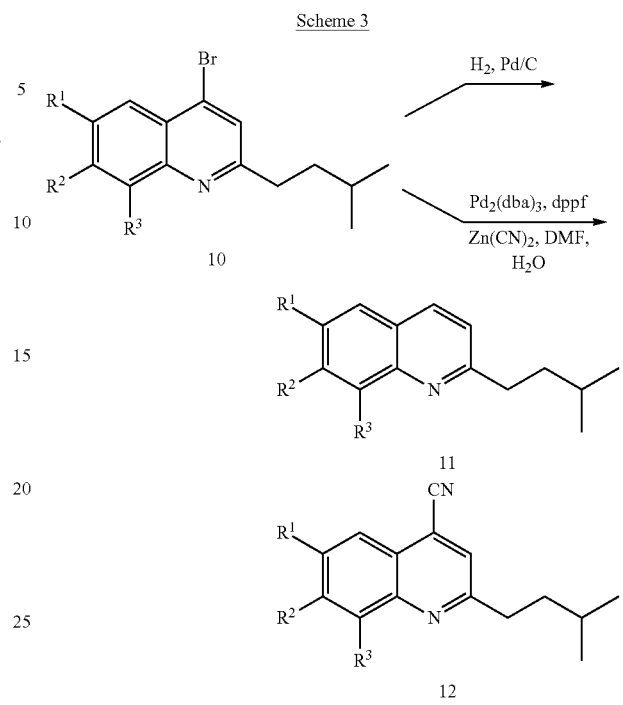

Compounds of formula 15, wherein R¹, R², and R³ are as defined in formula (I), can be prepared as described in Scheme 4 from compounds of formula 12. Treatment of the later with a brominating agent such as N-bromosuccinimide and AIBN in carbon tetrachloride with heating affords compounds of formula 13. Displacement of the bromide with sodium azide in an organic solvent such as acetone, acetonitrile, DMF or pyridine affords compounds of formula 14. Reduction of the azide to the amine can be carried out by treating compounds of formula 14 with triphenylphosphine in a mixture of THF and water to give compounds of formula 15. Alternatively, compounds of formula 14 can be placed under a hydrogen atmosphere in the presence of palladium on carbon in a solvent such as methanol or ethanol to furnish compounds of formula 15.

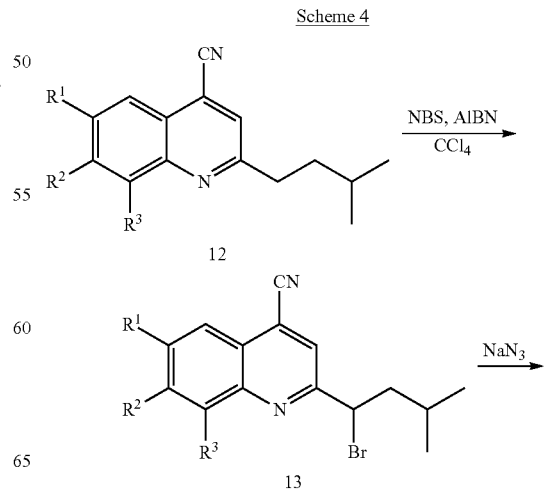

-continued

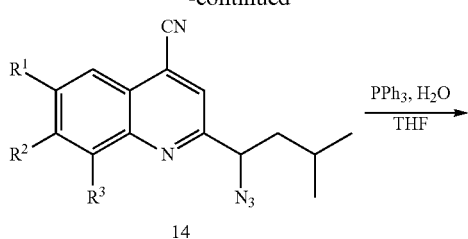

14

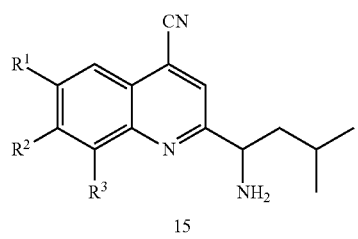

15

It is recognized by one skilled in the art that the order of incorporation of some substituents may be changed. For example, the $R^1$ and $R^2$ substituents in compounds of formula (I) wherein $R^1$=oxazol-5-yl and $R^2$=methoxy can be incorporated as shown in Scheme 5. Treatment of compounds of formula 16, which contains a methoxy group at $R^2$, with TosMIC in the presence of a base such as potassium carbonate in a solvent such as methanol affords compounds of formula 17. Reduction of the nitro group in 17 is accomplished using standard conditions such as, but not limited to, $H_2$ and Pd/C, zinc with ammonium chloride, or tin chloride in an appropriate solvent such as methanol or ethanol at temperatures ranging from 0° C. to 100° C. to give compounds of formula 18. Compounds of formula 18 can be further processed using the appropriate procedures described in Schemes 1-4 to provide compounds of formula 19, wherein $R^4$=3-methylbutyl or 1-amino-3-methylbutyl; $R^5$=H; and $R^6$=H, Br, OMe, or CN.

Scheme 5

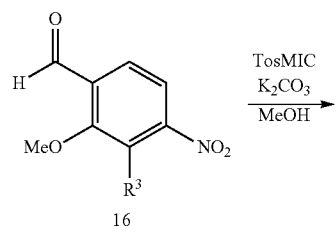

16

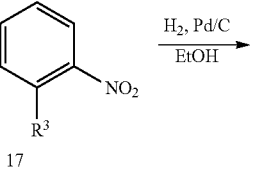

17

-continued

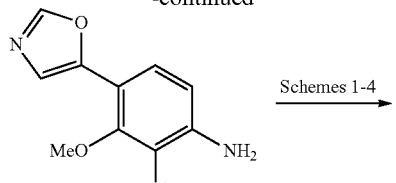

18

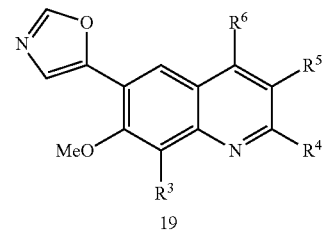

19

Compounds of formula 23, wherein $R^1$, $R^2$, and $R^3$ are as defined in formula (I), can be prepared as described in Scheme 6. Compounds of formula 20 and 21 are combined and heated with phosphorus oxychloride to furnish compounds of formula 22. Coupling of compounds of formula 22 with aryl and heteroarylboronic acids in the presence of a palladium catalyst such as Pd(PPh$_3$)$_4$ or Pd(OAc)$_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 23. The coupling reaction is carried out by heating the reaction mixture using standard laboratory methods or by heating the reaction mixture in a microwave.

Scheme 6

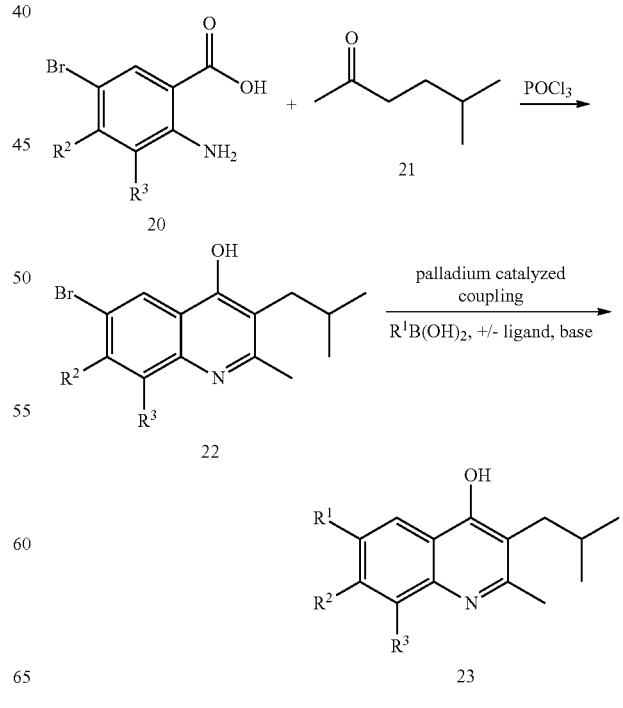

Compounds of formula 29, wherein $R^1$, $R^2$, and $R^3$ are as defined in formula (I), can be prepared as described in Scheme 7. Treatment of 24 with a base such as LDA in a polar aprotic solvent such as THF followed by the addition of ethyl formate (25) affords 26. Compound 26 can be condensed with anilines of formula 5 in the presence of an acid such as acetic acid and 4 Å molecular sieves in a solvent such as toluene at temperatures ranging from 60° C. to 120° C. to furnish compounds of formula 27. Compounds of formula 27 are heated at 250° C. in phenyl ether resulting in cyclization to form compounds of formula 28. Coupling of compounds of formula 28 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 29. The coupling reaction is carried out by heating the reaction mixture using standard laboratory methods or by heating the reaction mixture in a microwave.

Scheme 7

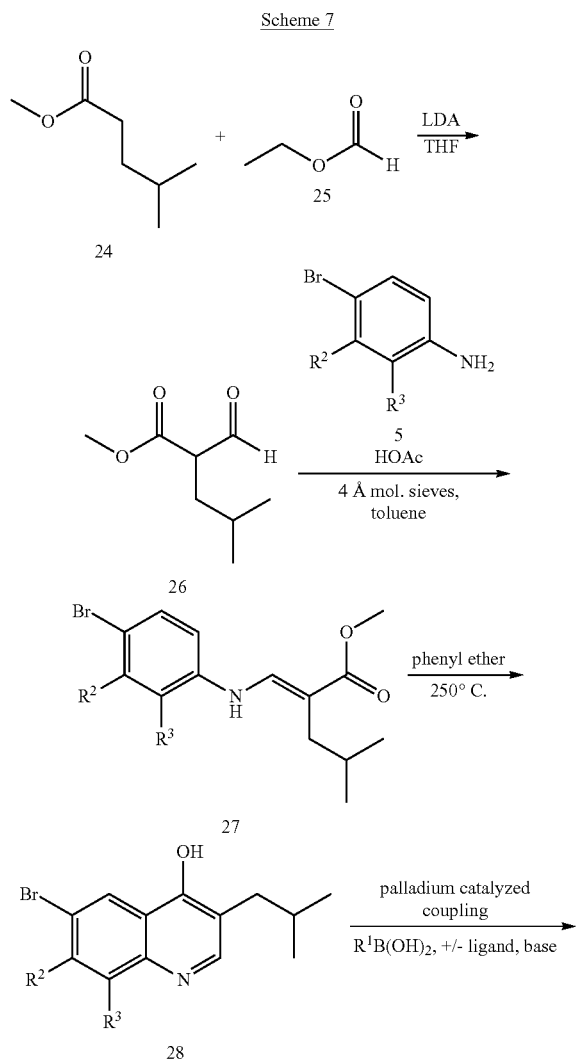

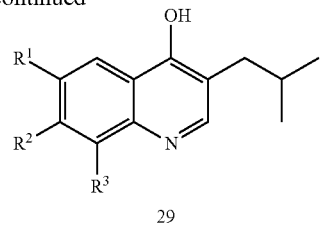

Compounds of formula 31, wherein $R^1$, $R^2$, $R^3$, and $R^4$ are as defined in formula (I), can be prepared as described in Scheme 8. Compounds of formula 30 can be prepared as illustrated in Scheme 1. Treatment of 30 with bromine in acetic acid furnishes compounds of formula 31.

Scheme 8

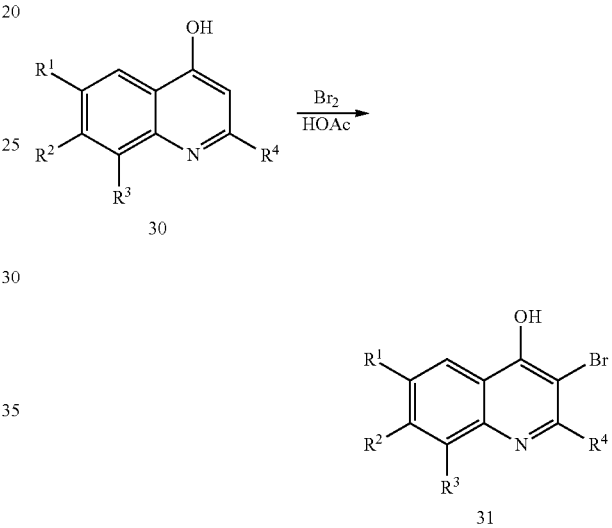

Compounds of formula 35, wherein $R^1$, $R^2$, and $R^3$ are as defined in formula (I), can be prepared from compounds of formula 6 (prepared as shown in Scheme 1) as described in Scheme 9. Compounds of formula 6 are heated in the presence of DMF and $POCl_3$ to furnish compounds of formula 32. Hydrolysis of the ester in 32 with reagents such as lithium hydroxide, sodium hydroxide or potassium hydroxide affords compounds of formula 33. Treatment of compounds of formula 33 with oxalyl chloride and catalytic DMF gives the corresponding acid chloride, which in turn is treated with ammonium hydroxide to afford compounds of formula 34. Coupling of compounds of formula 34 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 35. The coupling reaction is carried out by heating the reaction mixture using standard laboratory methods or by heating the reaction mixture in a microwave.

Scheme 9

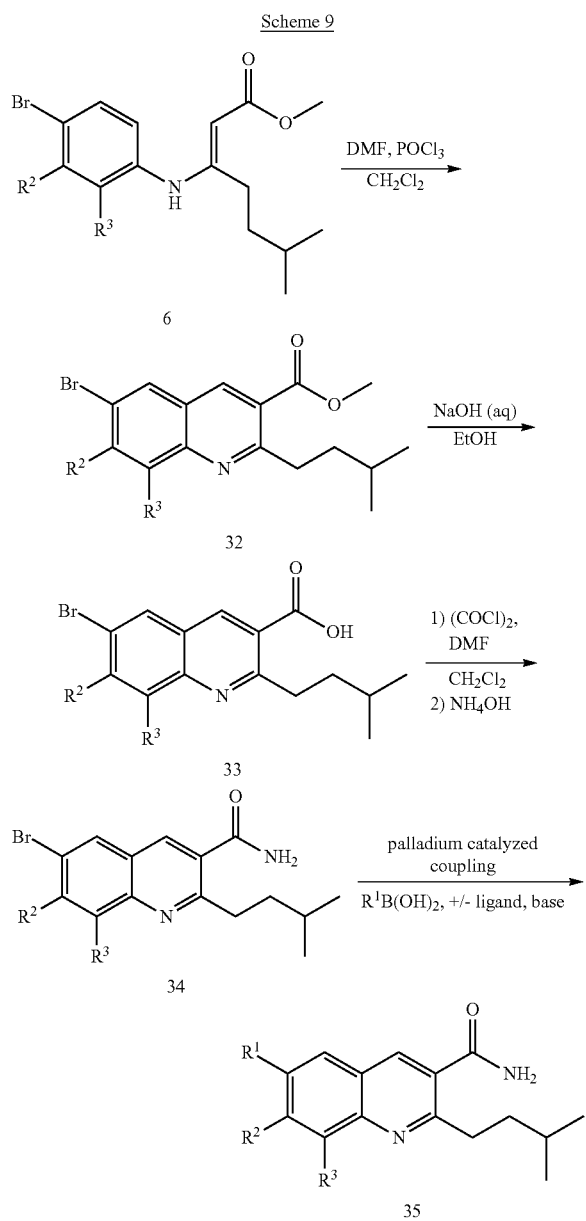

Compounds of formula 37, wherein $R^1$, $R^2$, and $R^3$ are as defined in formula (I), can be prepared from compounds of formula 34 (prepared as shown in Scheme 9) as described in Scheme 10. Treatment of compounds of formula 34 with trifluoroacetic anhydride in the presence of a base such as triethylamine or N,N-diisopropylethylamine results in the formation of compounds of formula 36. Coupling of compounds of formula 36 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 37. The coupling reaction is carried out by heating the reaction mixture using standard laboratory methods or by heating the reaction mixture in a microwave.

Compounds of formula 41 wherein $R^4$=4-methylpentan-2-one can be prepared from compounds of formula 38 as illustrated in Scheme 11. Treatment of compounds of formula 38 with N,O-dimethylhydroxylamine in the presence of a coupling agent such as TBTU and a base such as triethylamine or N,N-diisopropylethylamine results in the formation of compounds of formula 39. Treatment of compounds of the formula 39 with a Grignard reagent in a solvent such as THF or diethyl ether results in the formation of compounds of the formula 40. Coupling of compounds of formula 40 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 41 wherein $R^4$=4-methylpentan-2-one. The coupling reaction is carried out by heating the reaction mixture using standard laboratory methods or by heating the reaction mixture in a microwave.

Scheme 11

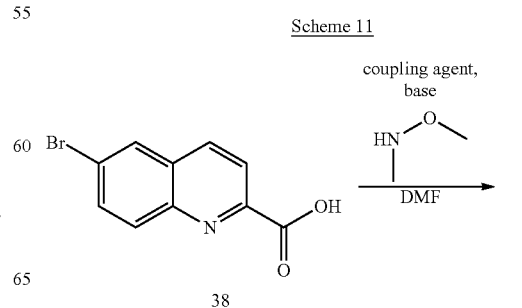

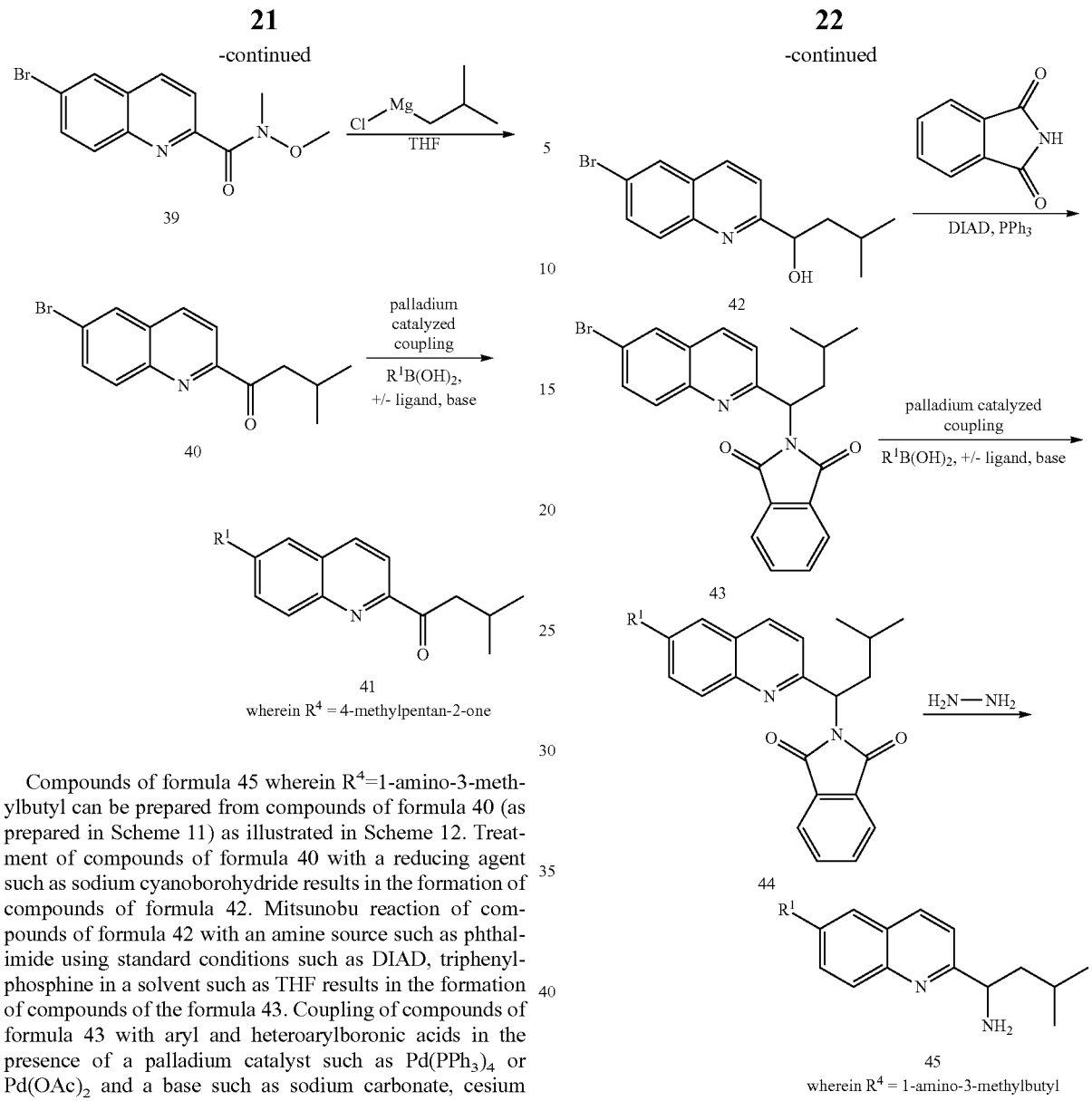

Compounds of formula 45 wherein $R^4$=1-amino-3-methylbutyl can be prepared from compounds of formula 40 (as prepared in Scheme 11) as illustrated in Scheme 12. Treatment of compounds of formula 40 with a reducing agent such as sodium cyanoborohydride results in the formation of compounds of formula 42. Mitsunobu reaction of compounds of formula 42 with an amine source such as phthalimide using standard conditions such as DIAD, triphenylphosphine in a solvent such as THF results in the formation of compounds of the formula 43. Coupling of compounds of formula 43 with aryl and heteroarylboronic acids in the presence of a palladium catalyst such as Pd(PPh$_3$)$_4$ or Pd(OAc)$_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 44. The coupling reaction is carried out by heating the reaction mixture using standard laboratory methods or by heating the reaction mixture in a microwave. Deprotection of the phthalate of compounds of formula 44 with a reagent such as hydrazine furnishes compounds of formula 45 wherein $R^4$=1-amino-3-methylbutyl.

Scheme 12

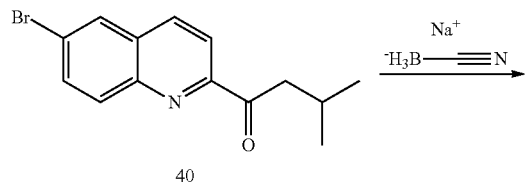

Compounds of formula 52 wherein $R^4$=1-amino-3-methylbutyl can be prepared from compounds of formula 46 as illustrated in Scheme 13. Treatment of compounds of formula 46 with an oxidizing agent such as selenium dioxide results in the formation of compounds of formula 47. Sulfinamide formation with racemic or optically pure t-butylsulfinamide in the presence of a dehydrating agent such as tetraethoxy titanium affords compounds of formula 48 as a mixture of diastereomers. Treatment of compounds of the formula 48 with a Grignard reagent in a solvent such as THF or diethyl ether results in the formation of compounds of the formula 49. Conversion of compounds of formula 49 via palladium mediated coupling with hexamethylditin in the presence of a palladium catalyst such as Pd(PPh$_3$)$_4$, PdCl$_2$(PPh$_3$)$_2$, or Pd(OAc)$_2$ in a solvent such as MeCN, toluene, THF, or dioxane at temperatures ranging from 40 to 150° C. furnishes compounds of formula 50. Stille coupling of compounds of formula 50 with aryl and heteroarylhalides in the presence of a palladium catalyst such as Pd(PPh$_3$)$_4$, PdCl$_2$(PPh$_3$)$_2$, or Pd(OAc)$_2$ and a base such as sodium carbonate, cesium carbonate, potassium carbonate, or potassium phosphate in the presence or absence of an additive such as tetramethyl ammonium bromide or fluoride in a solvent such as DME, DMF, toluene, THF, or dioxane at temperatures ranging from 20 to 150° C. furnishes compounds of formula 51. The coupling reaction is carried out by heating the reaction mixture using standard laboratory methods or by heating the reaction mixture in a microwave. Deprotection of the sulfinamide of compounds of formula 51 with a reagent such as HCl furnishes compounds of formula 52 wherein $R^4$=1-amino-3-methylbutyl.

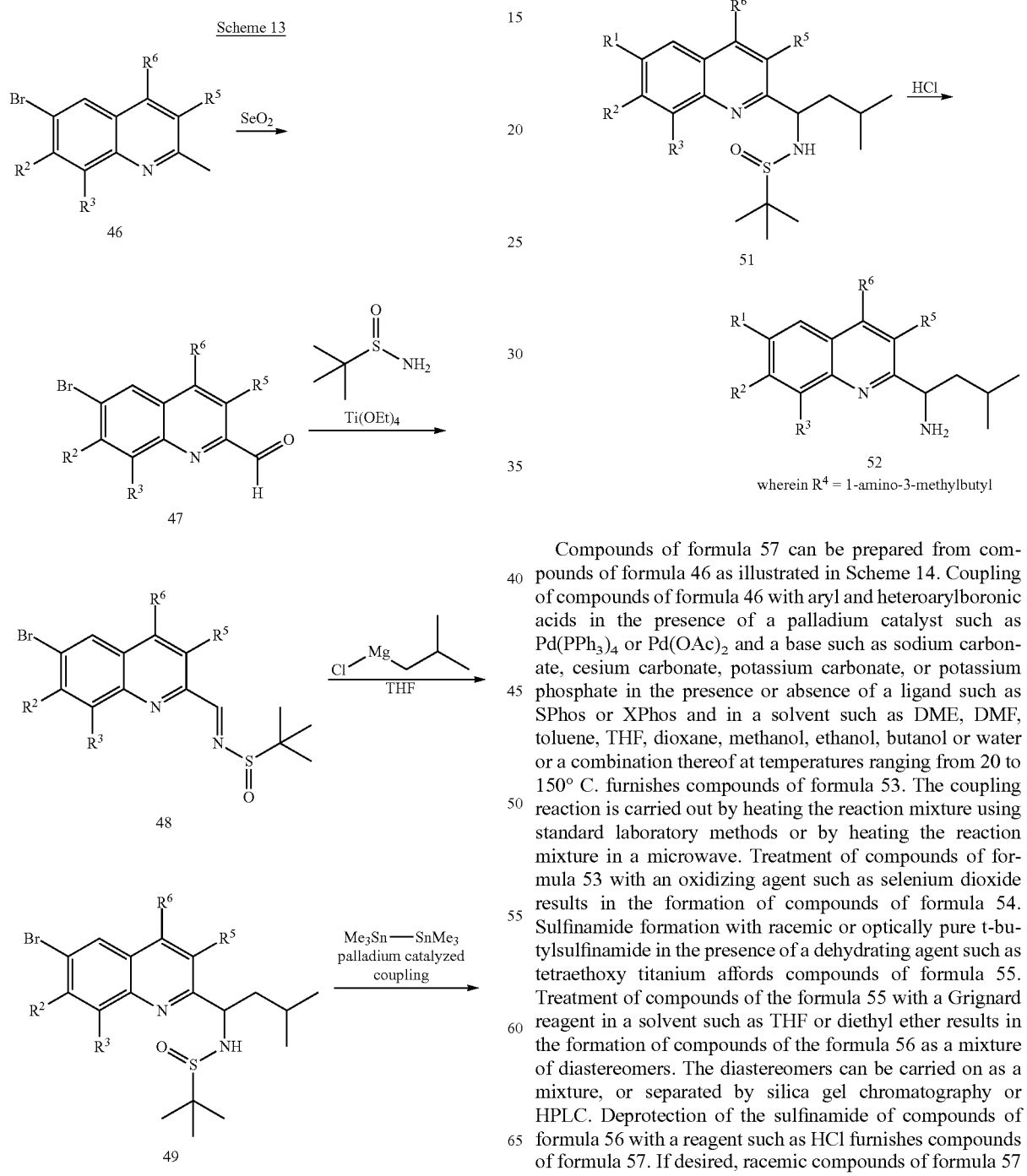

Compounds of formula 57 can be prepared from compounds of formula 46 as illustrated in Scheme 14. Coupling of compounds of formula 46 with aryl and heteroarylboronic acids in the presence of a palladium catalyst such as Pd(PPh$_3$)$_4$ or Pd(OAc)$_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 53. The coupling reaction is carried out by heating the reaction mixture using standard laboratory methods or by heating the reaction mixture in a microwave. Treatment of compounds of formula 53 with an oxidizing agent such as selenium dioxide results in the formation of compounds of formula 54. Sulfinamide formation with racemic or optically pure t-butylsulfinamide in the presence of a dehydrating agent such as tetraethoxy titanium affords compounds of formula 55. Treatment of compounds of the formula 55 with a Grignard reagent in a solvent such as THF or diethyl ether results in the formation of compounds of the formula 56 as a mixture of diastereomers. The diastereomers can be carried on as a mixture, or separated by silica gel chromatography or HPLC. Deprotection of the sulfinamide of compounds of formula 56 with a reagent such as HCl furnishes compounds of formula 57. If desired, racemic compounds of formula 57 can be separated into the two enantiomers via chiral HPLC.

Scheme 14

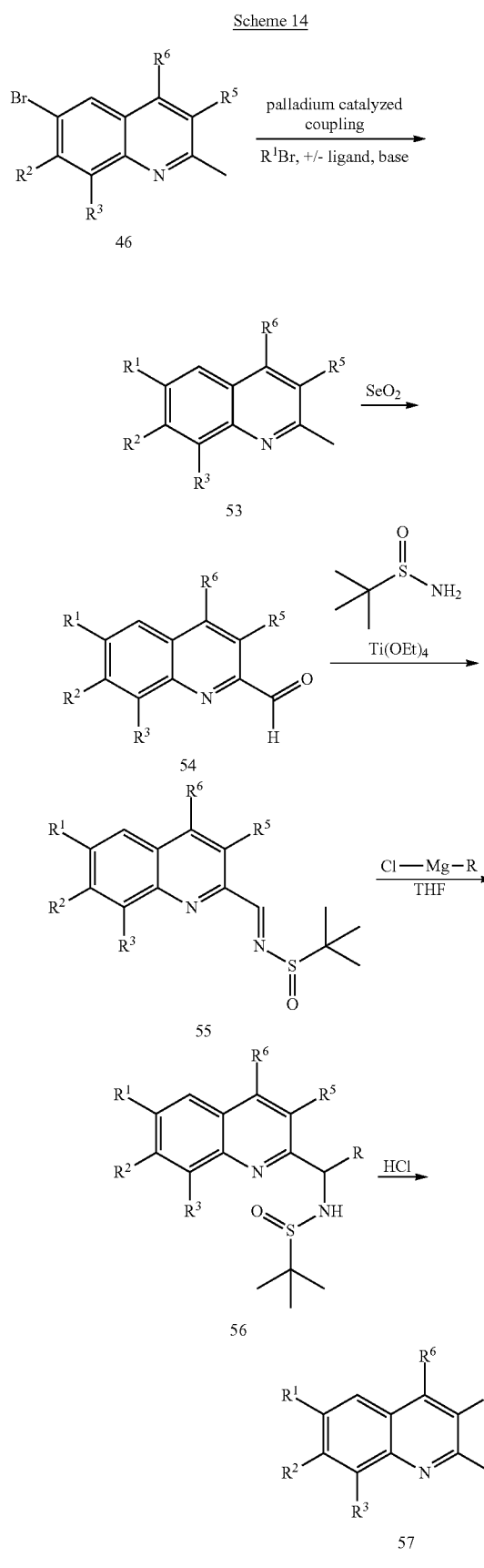

Using the methods described in Scheme 15, compounds of formula 64 can be prepared from compounds of formula 10 (prepared as described in Scheme 2). Treatment of compounds of formula 10 with NBS in the presence of AIBN in a solvent such as carbon tetrachloride can afford compounds of formula 58. Treatment of compounds of formula 58 with sodium azide in a solvent such as acetone at elevated temperatures can afford compounds of formula 59. Reduction of the azide in compounds of formula 59 with triphenylphosphine in a solvent such as THF can afford compounds of formula 60. Protection of the amine with a group such as BOC followed by Negishi coupling with $Zn(CN)_2$ in the presence of a coupling agent such as tris-dibenzylideneacetone and a ligand such as DPPF in a solvent system such as DMF and water at temperatures ranging from 80 to 150° C. furnishes compounds of formula 62. Conversion of the nitrile in compounds of formula 62 to the tetrazole can be carried out in the presence of sodium azide and ammonium chloride in a solvent such as DMF at temperatures ranging from 80 to 120° C. to afford compounds of formula 63. Deprotection of compounds of formula 63 with a reagent such as HCl furnishes compounds of formula 64. If desired, racemic compounds of formula 64 can be separated into the two enantiomers via chiral HPLC.

Scheme 15

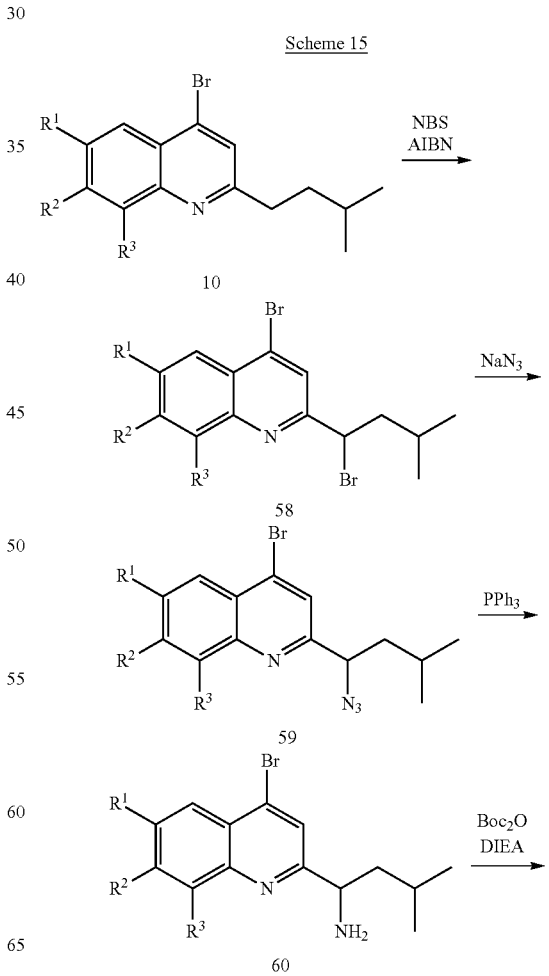

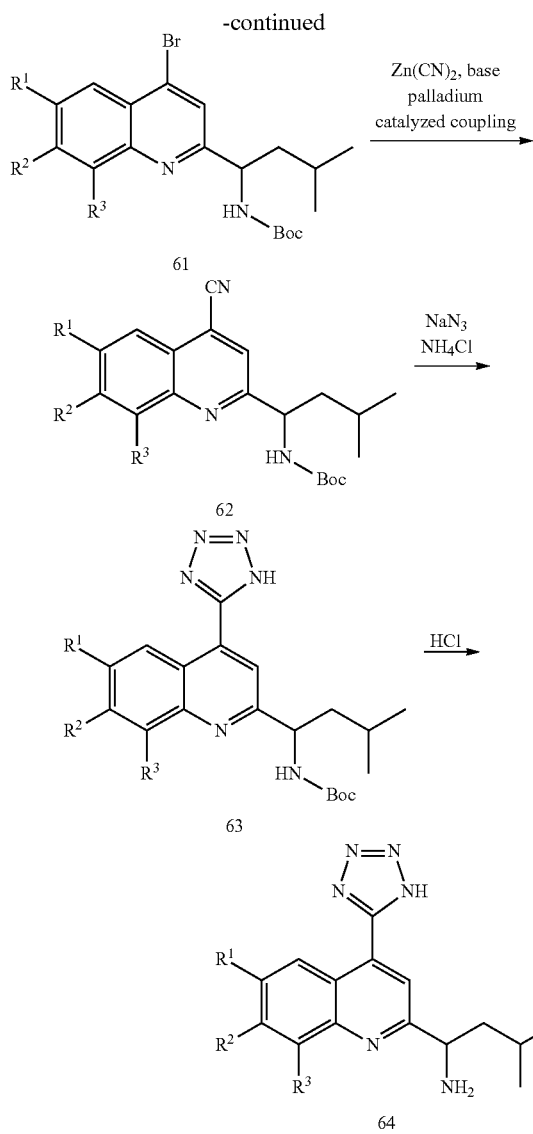

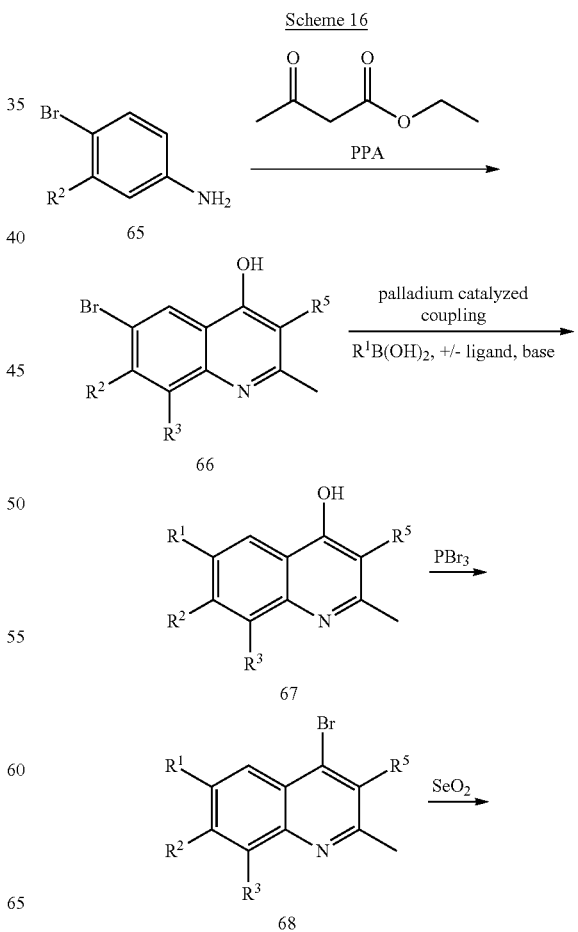

Scheme 16 tetraethoxy titanium affords compounds of formula 70. Treatment of compounds of the formula 70 with a Grignard reagent in a solvent such as THF or diethyl ether results in the formation of compounds of the formula 71 as a mixture of diastereomers. The diastereomers can be carried on as a mixture, or separated by silica gel chromatography or HPLC. Stille coupling of compounds of formula 71 with tributylethenylstannane in the presence of a palladium catalyst such as $Pd(PPh_3)_4$, $PdCl_2(PPh_3)_2$, or $Pd(OAc)_2$ and a base such as sodium carbonate, cesium carbonate, potassium carbonate, or potassium phosphate in the presence or absence of an additive such as tetramethyl ammonium bromide or fluoride in a solvent such as DME, DMF, toluene, THF, or dioxane at temperatures ranging from 20 to 150° C. furnishes compounds of formula 72. The coupling reaction is carried out by heating the reaction mixture using standard laboratory methods or by heating the reaction mixture in a microwave. Compounds of the formula 72 can be hydrogenated in the presence of palladium on carbon in a solvent such as methanol or ethanol to afford compounds of the formula 73. Deprotection of the sulfinamide of compounds of formula 73 with a reagent such as HCl furnishes compounds of formula 74. If desired, racemic compounds of formula 74 can be separated into the two enantiomers via chiral HPLC.

Compounds of formula 74 can be prepared from compounds of formula 65 as illustrated in Scheme 16. Condensation of 65 with ethyl 3-oxobutanoate in the presence of an acid such as PPA can afford compounds of the formula 66. Coupling of compounds of formula 66 with aryl and heteroarylboronic acids in the presence of a palladium catalyst such as $Pd(PPh_3)_4$ or $Pd(OAc)_2$ and a base such as sodium carbonate, cesium carbonate, potassium carbonate, or potassium phosphate in the presence or absence of a ligand such as SPhos or XPhos and in a solvent such as DME, DMF, toluene, THF, dioxane, methanol, ethanol, butanol or water or a combination thereof at temperatures ranging from 20 to 150° C. furnishes compounds of formula 67. The coupling reaction is carried out by heating the reaction mixture using standard laboratory methods or by heating the reaction mixture in a microwave. Treatment of compounds of formula 67 with a reagent such $PBr_3$ results in the formation of compounds of formula 68. Treatment of compounds of formula 68 with an oxidizing agent such as selenium dioxide results in the formation of compounds of formula 69. Sulfinamide formation with racemic or optically pure t-butylsulfinamide in the presence of a dehydrating agent such as -continued

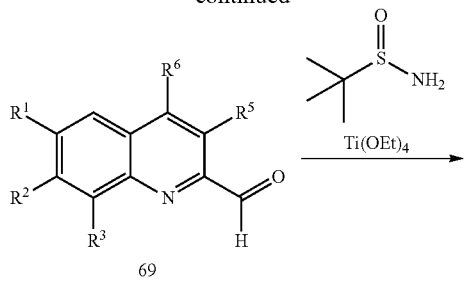 
69

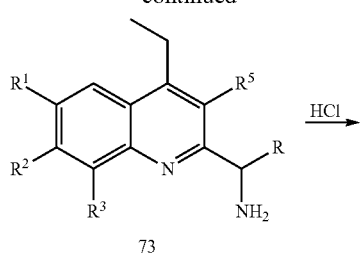
73

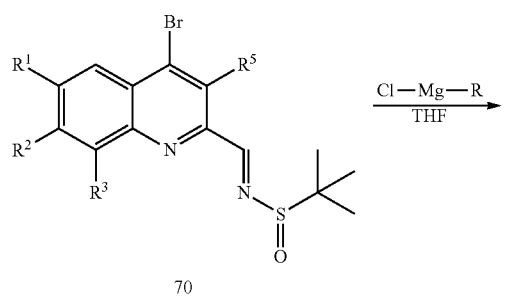
70

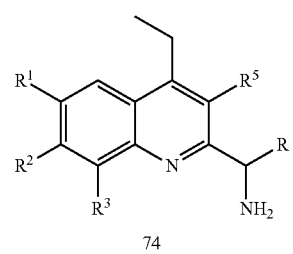
74

Intermediates of formula 75 are prepared as outlined in Scheme 17. 2-Amino-4-bromopyridine can be acylated with an acid chloride in the presence of a base such as TEA or DIEA in a solvent such as DMF or DCM to afford intermediates of the formula 75.

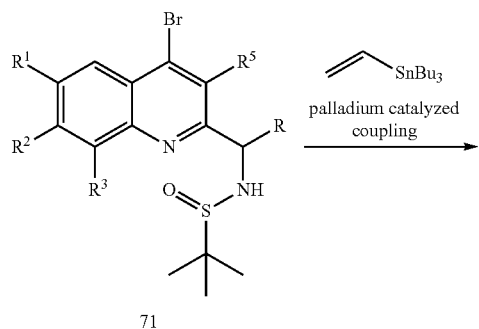
71

Scheme 17

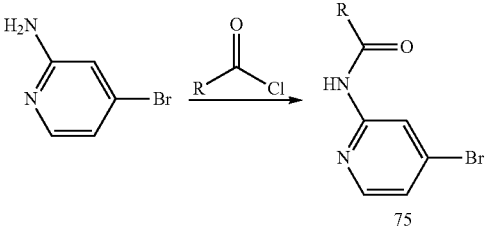
75

Intermediates of formula 76 are prepared as outlined in Scheme 18. 4-Bromo-2-fluoropyridine can be treated with an alkylamine in the presence of a base such as cesium carbonate in a solvent such as DMF to afford intermediates of the formula 76.

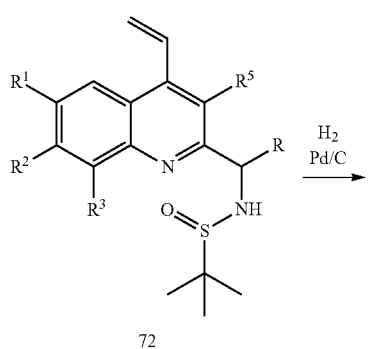
72

Scheme 18

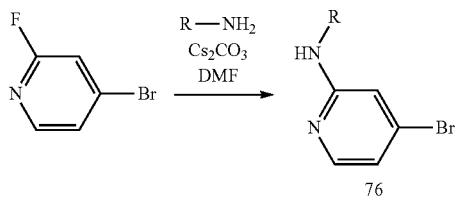
76

Intermediate 79 can be prepared as outlined in Scheme 19. Aniline can be treated with 4-methylbenzenesulfinic acid at 260° C. followed by treated with ethyl 2-cyanoacetate at 260° C. to afford 77. Intermediate 77 can be brominated in the presence of phosphorous oxybromide and phosphorous tribromide at 150° C. to give bromide 78. Intermediate 78 can be acylated with acetyl chloride in DCM to afford intermediate 79.

Scheme 19

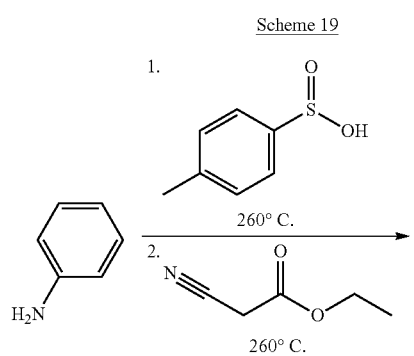

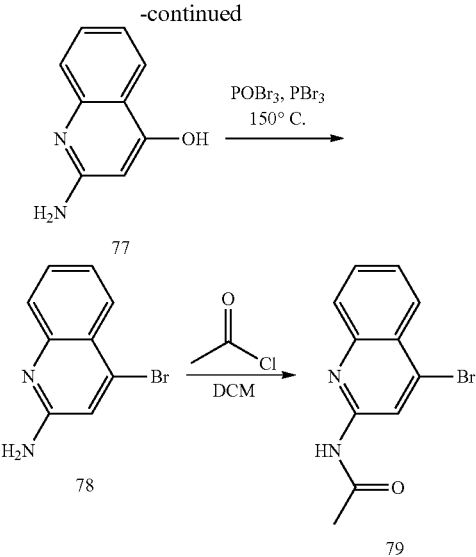

Various analogs synthesized using Schemes 1-16 are listed in Table 1. AAK1.

TABLE 1

(I)

| Example | $R^1$ | $R^2$ | $R^3$ | $R^4$ | $R^5$ | $R^6$ | $(M + H)^+$ |
|---|---|---|---|---|---|---|---|
| 1 | 4-pyridyl | H | H | isohexyl | H | OH | 293.1 |
| 2 | 4-pyridyl | H | H | isohexyl | H | OMe | 307.2 |
| 3 | 4-pyridyl | H | H | isohexyl | H | Br | 355.0 |
| 4 | 4-pyridyl | H | H | isohexyl | H | H | 277.1 |
| 5 | 4-pyridyl | H | H | isohexyl | H | N(Me)$_2$ | 320.1 |

TABLE 1-continued

| # | (col2) | (col3) | (col4) | (col5) | (col6) | (col7) | (col8) |
|---|---|---|---|---|---|---|---|
| 6 | pyridin-4-yl | H | H | isobutyl | H | CN | 302.1 |
| 7 | pyridin-4-yl | H | H | (S)-1-amino-3-methylbutyl | H | CN | 317.2 |
| 8 | pyridin-4-yl | H | H | (R)-1-amino-3-methylbutyl | H | CN | 317.2 |
| 9 | oxazol-5-yl | OMe | H | isobutyl | H | OH | 313.1 |
| 10 | oxazol-5-yl | OMe | H | isobutyl | H | Br | 375.0 |
| 11 | oxazol-5-yl | OMe | H | isobutyl | H | CN | 322.1 |
| 12 | oxazol-5-yl | OMe | H | 1-amino-3-methylbutyl | H | CN | 337.1 |
| 13 | oxazol-5-yl | OMe | H | 1-amino-3-methylbutyl | H | CN | 337.1 |
| 14 | pyridin-4-yl | H | H | Me | isobutyl | OH | 293.0 |
| 15 | pyridin-4-yl | H | H | H | isobutyl | OH | 279.2 |
| 16 | pyridin-4-yl | H | H | isobutyl | Br | OH | 371.1 |

TABLE 1-continued

| 17 | pyridin-4-yl | H | H | (isobutyl-methyl) | CONH₂ | H | 320.1 |
| 18 | pyridin-4-yl | H | H | (isobutyl-methyl) | CN | H | 302.1 |
| 19 | pyridin-3-yl | H | H | (isobutyl-methyl ketone) | H | H | 291.1 |
| 20 | pyridin-4-yl | H | H | (1-amino-3-methylbutyl) | H | H | 292.2 |
| 21 | pyridin-4-yl | H | H | (1-amino-3-methylbutyl) | H | H | 292.2 |
| 22 | 3-methoxypyridin-4-yl | H | H | (1-amino-3-methylbutyl) | H | H | 322.2 |
| 23 | 3-methoxypyridin-4-yl | H | H | (1-amino-3-methylbutyl) | H | H | 322.2 |
| 24 | 2-methoxypyridin-4-yl | H | H | (1-amino-3-methylbutyl) | H | H | 322.1 |
| 25 | 1H-pyrrolo[2,3-b]pyridin-4-yl | H | H | (1-amino-3-methylbutyl) | H | H | 331.0 |

TABLE 1-continued

| | | | | | | | |
|---|---|---|---|---|---|---|---|
| 26 | (quinolin-4-yl) | H | H | (1-amino-3-methylbutyl) | H | H | 342.0 |
| 27 | (isoquinolin-6-yl) | H | H | (1-amino-3-methylbutyl) | H | H | 342.0 |
| 28 | (2-(dimethylamino)pyrimidin-4-yl) | H | H | (1-amino-3-methylbutyl) | H | H | 336.0 |
| 29 | (2-aminopyridin-4-yl) | H | H | (1-amino-3-methylbutyl) | H | H | 307.0 |
| 30 | (2-acetamidopyridin-4-yl) | H | H | (4-methyl-2-oxopentyl) | H | H | 348.0 |
| 31 | (pyridin-4-yl) | H | H | (3-methylbutyl) | H | =S | 309.2 |
| 32 | (pyridin-4-yl) | H | H | (3-methyl-1-(2,2,2-trifluoroethoxy)butyl) | H | H | 375.0 |
| 33 | (2-acetamidopyridin-4-yl) | H | H | (1-amino-3-methylbutyl) | H | H | 349.2 |

TABLE 1-continued
| | | | | | | | |
|---|---|---|---|---|---|---|---|
| 34 | 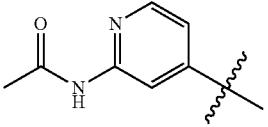 [SMILES: *c1ccnc(NC(C)=O)c1] | H | H | 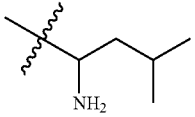 [SMILES: *C(N)CC(C)C] | H | H | 349.2 |
| 35 | 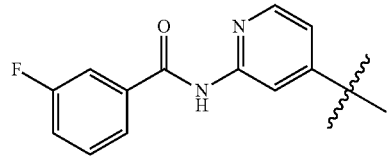 [SMILES: *c1ccnc(NC(=O)c2cccc(F)c2)c1] | H | H | 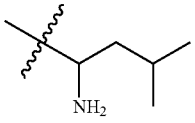 | H | H | 429.2 |
| 36 | 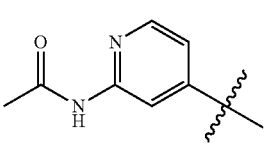 [SMILES: *c1ccnc(NC(C)=O)c1] | H | H | 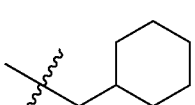 | H | H | 375.2 |
| 37 | 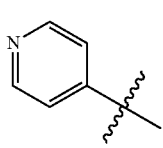 [SMILES: *c1ccncc1] | H | H | 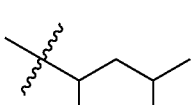 | H | 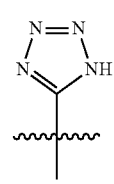 | 360.2 |
| 38 | 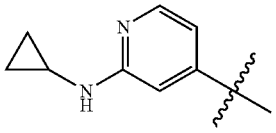 [SMILES: *c1ccnc(NC2CC2)c1] | H | H | 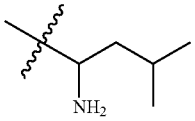 | H | H | 347.2 |
| 39 | 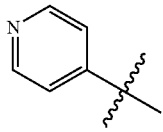 [SMILES: *c1ccncc1] | H | H | 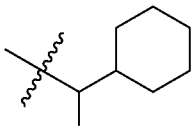 | H | CONH$_2$ | 361.0 |
| 40 | 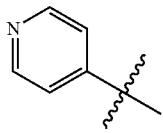 [SMILES: *c1ccncc1] | H | H | 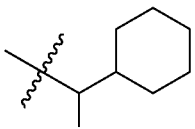 | H | CONH$_2$ | 361.2 |
| 41 | 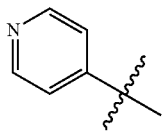 [SMILES: *c1ccncc1] | H | H | 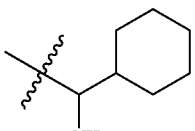 | H | CN | (M − H)$^-$: 341.2 |
| 42 | 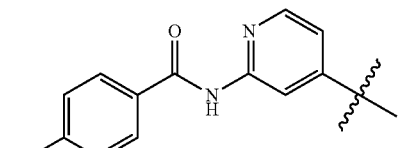 | H | H | 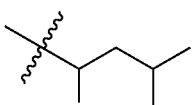 | H | H | 479.2 |
| 43 | 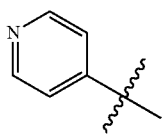 | H | H | 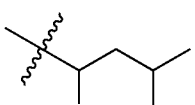 | H | Et | 320.2 |

TABLE 1-continued

| # | (structure) | | | (structure) | | | MW |
|---|---|---|---|---|---|---|---|
| 44 | 4-pyridyl-CH(CH3)- | H | F | -C(CH3)(NH2)CH2CH(CH3)2 | | H | CN | 335.2 |
| 45 | 2-(acetylamino)pyridin-4-yl-CH(CH3)- | H | H | -C(CH3)(OH)CH2CH(CH3)2 | | H | H | 350.2 |
| 46 | 2-(acetylamino)quinolin-4-yl-CH(CH3)- | H | H | -C(CH3)(NH2)CH2CH(CH3)2 | | H | H | 399.2 |
| 47 | 3-(acetylamino)quinolin-4-yl-CH(CH3)- | H | H | -C(CH3)(NH2)CH2CH(CH3)2 | | H | H | 399.2 |
| 48 | 2-aminoquinolin-4-yl-CH(CH3)- | H | H | -C(CH3)(NH2)CH2CH(CH3)2 | | H | H | 357.2 |
| 49 | 2-aminoquinolin-4-yl-CH(CH3)- | H | H | -C(CH3)(NH2)CH2CH(CH3)2 | | H | H | 357.2 |
| 50 | 2-cyclopropylpyridin-4-yl-CH(CH3)- | H | H | -C(CH3)(NH2)CH2CH(CH3)2 | | H | H | 332.2 |

DESCRIPTION OF THE SPECIFIC EMBODIMENTS

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ using at least one of the following methods. HPLC retention times were obtained using at least one of the following methods:

LC-MS methods:
LC/MS Method A=Column: PUROSPHER@star RP-18 (4×55 mm), 3 μm; Buffer: 20 mM NH$_4$OAc IN WATER; Mphase A: Buffer+ACN(90+10); Mphase B: Buffer+MeCN (10+90); Flow: 2.5 mL/min)
LC/MS Method B=Column: ZORBAX SB C18 (4.6×50 mm), 5 μm; Positive mode Mphase A: 10% MeOH-90% H$_2$O-0.1% TFA; Mphase B: 90% MeOH-10% H$_2$O-0.1% TFA; Flow: 5 mL/min)
LC/MS Method C=Column—Ascentis Express C8 (5×2.1 mm), 2.7 μm; Mphase A: 2% MeCN-98% H$_2$O-10 mM NH$_4$COOH; Mphase B: 98% ACN-2% H$_2$O-10 mM NH$_4$COOH; Flow: 1/min)
LC/MS Method D=Column—ACQUITY UPLC BEH C18 (2.1×50 mm), 1.7 μm; Mphase A: 0.1% TFA in water; Mphase B: ACN; Flow: 1 mL/min)
LC/MS Method E=Column—Ascentis Express C18 (5×2.1 mm), 2.7 μm; Mphase A: 2% MeCN-98% H$_2$O-10 mM NH$_4$COOH; Mphase B: 98% ACN-2% H$_2$O-10 mM NH$_4$COOH; Flow: 1 mL/min)

Chiral HPLC Methods:
Method A1: CHIRALCEL OJH (250×4.6) mm 5 micron
  Mob. phase: 0.2% DEA in n-hexane:ethanol (80:20)
Method A2: CHIRALCEL OJH (250×4.6) mm 5 micron
  Mob. phase: 0.2% DEA in n-hexane:ethanol (70:30)
Method B1: CHIRALCEL AD-H (250×4.6) mm 5 micron
  Mob. Phase: 0.2% DEA in n-hexane:ethanol (70:30)
Method B2: CHIRALCEL AD-H (250×4.6) mm 5 micron
  Mob. Phase: n-hexane:ethanol (50:50)
Method C1: CHIRALCEL—ASH (250×4.6) mm 5 micron
  Mob. Phase: 0.2% DEA in n-hexane:ethanol (70:30)
Method D1: CHIRALCEL IC (250×4.6) mm 5 micron
  Mob. Phase: 0.2% DEA in hexane:ethanol (70:30)

Chiral SFC Methods:
Method A1: Column: CHIRALCEL OD H; Co Solvent: 0.5% DEA in Methanol; Co Solvent %: 30; Total flow: 3 g/min; Column Temperature: 34.8; Back pressure: 100 bar; Instrument: THAR SFC
Method A2: Column: CHIRALCEL OD H; Co Solvent: 0.5% DEA in Methanol; Co Solvent %: 25; Total flow: 3 g/min; Back pressure: 100 bar; Instrument: THAR SFC
Method B1: Column: LUX-C4; Co Solvent: 0.5% DEA in Methanol; Co Solvent %: 40; Total flow: 3 g/min; Back pressure: 103 bar; Instrument: THAR SFC Analytical HPLC methods:
Method A: Waters analytical C18 sunfire column (4.6×150 mm, 3.5 μm); mobile phase: Buffer: 0.05% TFA in H$_2$O pH=2.5 adjusted with ammonia
A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.
Method B: Waters analytical phenyl Xbridge column (4.6×150 mm, 3.5 μm), mobile phase: Buffer: 0.05% TFA in H$_2$O pH=2.5 adjusted with ammonia
A=buffer and acetonitrile (95:5), B=acetonitrile and buffer (95:5); 0-15 min, 0% B→50% B; 15-18 min, 50% B→100% B; 18-23 min, 100% B; flow rate=1 mL/min; λ=254 nm and 220 nm; run time=28 min.
Method C: Waters analytical C18 sunfire column (4.6×150 mm, 3.5 μm); mobile phase: Buffer: 0.05% TFA in H$_2$O pH=2.5 adjusted with ammonia
A=buffer and acetonitrile (95:5), B=acetonitrile and buffer (95:5); 0-12 min, 10% B→100% B; 12-15 min, 100% B; flow rate=1 mL/min; λ=254 nm and 220 nm; run time=17 min.
Method D: Waters analytical phenyl Xbridge column (4.6×150 mm, 3.5 μm), mobile phase: Buffer: 0.05% TFA in H$_2$O pH=2.5 adjusted with ammonia
A=buffer and acetonitrile (95:5), B=acetonitrile and buffer (95:5); 0-12 min, 10% B→100% B; 12-15 min, B→100% B; flow rate=1 mL/min; λ=254 nm and 220 nm; run time=17 min.
Method E: ECLIPSE XDB C18 (4.6×150 mm, 3.5 μm); mobile phase
A=20 mM NH$_4$OAc in H$_2$O, B=acetonitrile; 0-12 min, 10% B→100% B; 12-15 min, 100% B; flow rate=1 mL/min; λ=254 nm and 220 nm; run time=18 min.
Method F: Waters analytical phenyl Xbridge C18 column (4.6×150 mm, 3.5 μm), mobile phase: A=20 mM NH$_4$OAc in H$_2$O, B=acetonitrile; 0-12 min, 10% B→100% B; 12-15 min, B→100% B; flow rate=1 mL/min; λ=254 nm and 220 nm; run time=20 min.

Example 1

2-Isopentyl-6-(pyridin-4-yl)quinolin-4-ol

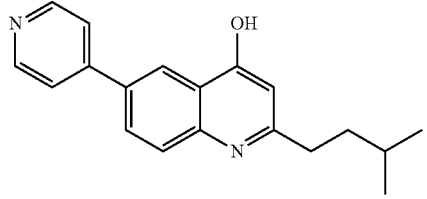

Part A. Methyl 6-methyl-3-oxoheptanoate

To a suspension of sodium hydride (3.37 g, 84 mmol) in THF (220 mL) at 0° C. was added methyl 3-oxobutanoate (8.9 g, 77 mmol) in THF (50 mL) via cannula. The reaction mixture was stirred at 0° C. for 15 min. n-BuLi (50.3 mL, 80 mmol) was then added dropwise via syringe over 15 min at 0° C. Stirring was continued at 0° C. for 15 min. 1-Iodo-2-methylpropane (14.81 g, 80 mmol) dissolved in THF (50 mL) was then added dropwise via cannula. The cooling bath was removed and the reaction mixture was allowed to warm to room temperature and was stirred for 4 h. The reaction was quenched by the addition of a 3 M HCl solution (aq.) (60 mL). The mixture was transferred to a separatory funnel and the aqueous layer was extracted with ether (1×300 mL followed by 2×150 mL). The combined organic layers were washed with water until neutral (5×150 mL) then brine (150 mL), dried over MgSO$_4$, filtered, and concentrated. The residue was purified by column chromatography on silica gel (15%→30% ethyl acetate in hexanes) to afford methyl 6-methyl-3-oxoheptanoate (4.65 g, 35% yield) as a pale yellow oil: ¹H NMR (400 MHz, CDCl₃) δ 3.76 (s, 3H), 3.48 (s, 2H), 2.52-2.59 (m, 2H), 1.47-1.62 (m, 3H), 0.91 (d, J=6.5 Hz, 6H).

Part B. (E)-Methyl 3-((4-bromophenyl)amino)-6-methylhept-2-enoate

To a solution of 4-bromoaniline (5.09 g, 29.6 mmol) and methyl 6-methyl-3-oxoheptanoate (5.10 g, 29.6 mmol) in toluene (30 mL) was added acetic acid (0.848 mL, 14.8 mmol) and 4 Å molecular sieves (5.0 g). The mixture was heated at 85° C. for 24 h. The mixture was cooled to room temperature and was concentrated. The residue was purified by column chromatography on silica gel (10%→50% ethyl acetate in hexanes) to afford (E)-methyl 3-((4-bromophenyl)amino)-6-methylhept-2-enoate (4.51 g, 47% yield) as a pale yellow solid: ¹H NMR (400 MHz, CDCl₃) δ 9.33 (br s, 1H), 7.43-7.51 (m, 4H), 7.23-7.28 (m, 2H), 6.57-6.63 (m, 2H), 5.32 (s, 1H), 3.59 (s, 3H), 3.51 (s, 3H), 2.56-2.64 (m, 2H), 1.49-1.64 (m, 3H), 0.93 (d, J=6.5 Hz, 6H)

Part C. 6-bromo-2-isopentylquinolin-4(1H)-one

A mixture of phenyl ether (40 mL) and methyl 3-(4-bromophenylamino)-6-methylhept-2-enoate (2.25 g, 6.90 mmol) in a 100 mL round bottom flask was heated at 250° C. for 1 h. The mixture was cooled down and was transferred to a larger flask containing hexanes (200 mL) preheated to 40° C. in a separate oil bath. The solid was collected on Buchner funnel and was washed with hexanes to give 6-bromo-2-isopentylquinolin-4(1H)-one (1.62 g, 80% yield) as a brown solid: ¹H NMR (400 MHz, DMSO-d₆) δ 11.66 (s, 1H), 8.12 (d, J=2.3 Hz, 1H), 7.77 (dd, J=8.9, 2.4 Hz, 1H), 7.52 (d, J=8.8 Hz, 1H), 5.99 (d, J=1.5 Hz, 1H), 2.57-2.64 (m, 2H), 1.52-1.65 (m, 3H), 0.94 (d, J=6.3 Hz, 6H); LCMS (ESI) m/e 294.0 [(M+H)⁺, calcd for C₁₄H₁₇BrNO 294.0].

Part D. 2-Isopentyl-6-(pyridin-4-yl)quinolin-4(1H)-one

To a solution of 6-bromo-2-isopentylquinolin-4(1H)-one (1.50 g, 5.10 mmol) in toluene (32 mL) and ethanol (8 mL) was added pyridin-4-ylboronic acid (0.940 g, 7.65 mmol) and 1 M aqueous sodium carbonate solution (6.12 mL, 6.12 mmol). The mixture was degassed by sonication for several minutes. Pd(PPh₃)₄ (0.589 g, 0.510 mmol) was then added and the mixture was heated at 95° C. for 3 h. The reaction mixture was diluted with 5% MeOH in CH₂Cl₂ and was transferred to a separatory funnel containing saturated aqueous NaHCO₃ solution (25 mL). The aqueous layer was extracted with 5% MeOH in CH₂Cl₂ (3×50 mL). After the first extraction, the solid that was present was collected on a Buchner funnel. The filtrate was poured into the separatory funnel and extracted 2 more times. The combined organic layers were washed with brine (25 mL), dried over MgSO₄, filtered and concentrated to give a brown solid. The solid that was collected on the Buchner funnel and the solid from concentration of the filtrate were purified separately by column chromatography on silica gel (4%→10% methanol in dichloromethane) to afford 820 mg and 270 mg, respectively of desired product. The products were combined to furnish 2-isopentyl-6-(pyridin-4-yl)quinolin-4-ol (1.15 g, 77% yield) as a pale-yellow solid: ¹H NMR (400 MHz, DMSO-d₆) δ 11.67 (s, 1H), 8.66 (dd, J=4.5, 1.5 Hz, 1H), 8.43 (d, J=2.0 Hz, 1H), 8.09 (dd, J=8.8, 2.3 Hz, 1H), 7.78 (dd, J=4.6, 1.6 Hz, 2H), 7.68 (d, J=8.5 Hz, 1H), 6.02 (s, 1H), 3.18 (d, J=5.3 Hz, 1H), 2.61-2.66 (m, 2H), 1.56-1.65 (m, 3H), 0.96 (d, J=6.3 Hz, 6H); LCMS (ESI) m/e 293.1 [(M+H)⁺, calcd for C₁₉H₂₁N₂O 293.2].

Example 2

2-Isopentyl-4-methoxy-6-(pyridin-4-yl)quinoline

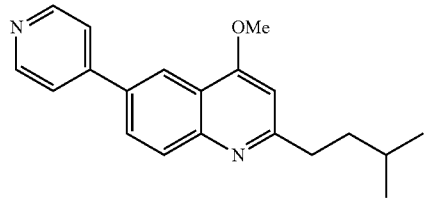 [SMILES: COc1cc(CCC(C)C)nc2ccc(-c3ccncc3)cc12]

To a solution of 2-isopentyl-6-(pyridin-4-yl)quinolin-4-ol (40 mg, 0.137 mmol), prepared as described Example 1, in DMF (1 mL) at room temperature was added sodium hydride (10.9 mg, 0.274 mmol). After stirring for 15 min, iodomethane (0.026 mL, 0.410 mmol) was added via syringe. The reaction mixture was stirred at room temperature for 45 min. The reaction mixture was quenched with saturated aqueous NaHCO₃ solution (1 mL) and was transferred to a reparatory funnel containing saturated aqueous NaHCO₃ solution (5 mL). The aqueous layer was extracted with 5% MeOH in CH₂Cl₂ (5×10 mL). The combined organic layers were washed with brine (10 mL), dried over MgSO₄, filtered, and concentrated. The residue was purified by column chromatography on silica gel (2%→7% methanol in CH₂Cl₂) to afford 2-isopentyl-4-methoxy-6-(pyridin-4-yl)quinoline (18.6 mg, 44% yield) as a yellow oil: ¹H NMR (400 MHz, CDCl₃) δ 8.69-8.74 (m, 2H), 8.46 (d, J=2.0 Hz, 1H), 8.14 (d, J=8.8 Hz, 1H), 7.97 (dd, J=8.8, 2.3 Hz, 1H), 7.65-7.70 (m, 2H), 6.72 (s, 1H), 4.12 (s, 3H), 2.94-3.00 (m, 2H), 1.70-1.78 (m, 3H), 1.02 (d, J=6.3 Hz, 6H); LCMS (ESI) m/e 307.2 [(M+H)⁺, calcd for C₂₀H₂₃N₂O 307.2].

Example 3

4-Bromo-2-isopentyl-6-(pyridin-4-yl)quinoline

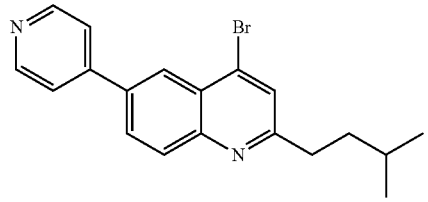 [SMILES: CC(C)CCc1cc(Br)c2cc(-c3ccncc3)ccc2n1]

To a suspension of 2-isopentyl-6-(pyridin-4-yl)quinolin-4-ol (250 mg, 0.855 mmol), prepared as described in Example 1, in DMF (2.5 mL) at room temperature was added phosphorous tribromide (0.097 mL, 1.026 mmol) via syringe. The reaction was exothermic. The reaction mixture was stirred at room temperature for 20 min. Ice water (10 mL) was added and the mixture was stirred at room temperature for 30 min. The pH of the mixture was adjusted to pH=8 by the addition of 1 N NaOH (aq.). The mixture was transferred to a reparatory funnel containing saturated aqueous NaHCO₃ solution (10 mL) and the aqueous layer was extracted with 10% methanol in dichloromethane (4×15 mL). The combined organic layers were washed with brine (10 mL), dried over MgSO$_4$, filtered, and concentrated. The residue was purified by column chromatography on silica gel (2%→7% methanol in CH$_2$Cl$_2$) to afford 4-bromo-2-isopentyl-6-(pyridin-4-yl)quinoline (181 mg, 60% yield) as an orange oil that solidified upon standing: $^1$H NMR (400 MHz, CDCl$_3$) δ 8.77 (br. s., 2H), 8.43 (d, J=1.8 Hz, 1H), 8.19 (d, J=8.8 Hz, 1H), 8.02 (dd, J=8.7, 2.1 Hz, 1H), 7.72 (d, J=6.0 Hz, 2H), 7.71 (s, 1H), 2.97-3.03 (m, 2H), 1.68-1.78 (m, 3H), 1.02 (d, J=6.5 Hz, 6H); LCMS (ESI) m/e 355.0 [(M+H)$^+$, calcd for C$_{19}$H$_{20}$BrN$_2$ 355.1].

Example 4

2-Isopentyl-6-(pyridin-4-yl)quinoline

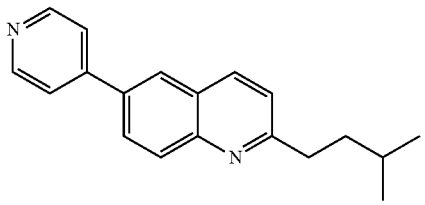 [SMILES: CC(C)CCc1ccc2cc(-c3ccncc3)ccc2n1]

4-Bromo-2-isopentyl-6-(pyridin-4-yl)quinoline (25 mg, 0.070 mmol), prepared as described in Example 3, was dissolved in ethanol (1 mL) and was treated with palladium on carbon (10%, Degussa type) (30.0 mg, 0.014 mmol). The mixture was placed under a hydrogen atmosphere at 1 atm for 2 h. The mixture was filtered through a pad of diatomaceous earth (Celite®) with methanol rinsing and the filtrate was concentrated. The residue was purified by column chromatography on silica gel (2%→4% methanol in CH$_2$Cl$_2$) to afford 2-isopentyl-6-(pyridin-4-yl)quinoline (5 mg, 24% yield) as a pale yellow oil: $^1$H NMR (400 MHz, CDCl$_3$) δ 8.74 (d, J=5.5 Hz, 2H), 8.17-8.23 (m, 2H), 8.08 (d, J=2.0 Hz, 1H), 7.99 (dd, J=8.8, 2.0 Hz, 1H), 7.66 (dd, J=4.5, 1.8 Hz, 2H), 7.41 (d, J=8.3 Hz, 1H), 3.05 (d, J=7.5 Hz, 2H), 1.70-1.78 (m, 3H), 1.02 (d, J=6.3 Hz, 6H); LCMS (ESI) m/e 277.1 [(M+H)$^+$, calcd for C$_{19}$H$_{21}$N$_2$ 277.2].

Example 5

2-Isopentyl-N,N-dimethyl-6-(pyridin-4-yl)quinolin-4-amine

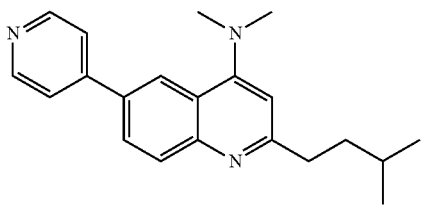 [SMILES: CC(C)CCc1cc(N(C)C)c2cc(-c3ccncc3)ccc2n1]

To a solution of 4-bromo-2-isopentyl-6-(pyridin-4-yl)quinoline (45 mg, 0.127 mmol), prepared as described in Example 3, in N-methyl-2-pyrrolidinone (1 mL) was added dimethylamine (2 M in THF) (0.317 mL, 0.633 mmol) and the mixture was heated at 100° C. for 14 h. The reaction mixture was transferred to a separatory funnel containing ether (20 mL). The organic layer was washed with water (3×5 mL). The combined organic layers were washed with brine (5 mL), dried over MgSO$_4$, filtered, and concentrated. The residue was purified by column chromatography on silica gel (4%→8% methanol in CH$_2$Cl$_2$) to afford 2-isopentyl-N,N-dimethyl-6-(pyridin-4-yl)quinolin-4-amine (5 mg, 12% yield) as a colorless oil. The product was purified further by reverse phase HPLC (5% MeCN:95% water→95% MeCN:5% water with 0.1% TFA). The organic solvent was removed under reduced pressure and the aqueous mixture was frozen and placed on the lyophilizer to afford 2-isopentyl-N,N-dimethyl-6-(pyridin-4-yl)quinolin-4-amine (5 mg, 12% yield) as a pale-yellow solid: $^1$H NMR (400 MHz, CD$_3$OD) δ 8.89 (d, J=6.5 Hz, 2H), 8.82 (d, J=1.8 Hz, 1H), 8.41 (dd, J=9.0, 2.0 Hz, 1H), 8.33 (d, J=6.5 Hz, 2H), 8.05 (d, J=8.8 Hz, 1H), 6.97 (s, 1H), 3.63 (s, 6H), 2.99 (dd, J=9.0, 7.0 Hz, 2H), 1.72-1.80 (m, 3H), 1.06 (d, J=6.5 Hz, 6H); LCMS (ESI) m/e 320.1 [(M+H)$^+$, calcd for C$_{21}$H$_{26}$N$_3$ 320.2].

Example 6

2-Isopentyl-6-(pyridin-4-yl)quinoline-4-carbonitrile

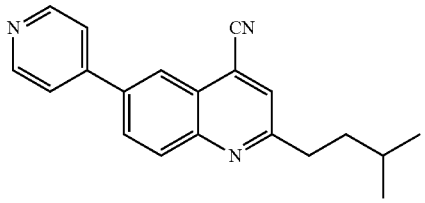 [SMILES: CC(C)CCc1cc(C#N)c2cc(-c3ccncc3)ccc2n1]

4-Bromo-2-isopentyl-6-(pyridin-4-yl)quinoline (180 mg, 0.507 mmol), prepared as described in Example 3, was dissolved in DMF (5 mL) and water (0.25 mL). The mixture was degassed by sonication for several minutes. Zinc cyanide (33.8 mL, 0.532 mmol), Pd$_2$(dba)$_3$ (23.20 mg, 0.025 mmol), and dppf (28.1 mg, 0.051 mmol) were added and the reaction mixture was heated at 120° C. under N$_2$ for 1.25 h. The mixture was cooled to room temperature and was transferred to a reparatory funnel containing ether (100 mL) and the organic layer was washed with water (5×15 mL) to remove any residual DMF. The combined organic layers were washed with brine (15 mL), dried over MgSO$_4$, filtered, and concentrated. The residue was purified by column chromatography on silica gel (1%→5% methanol in dichloromethane) to afford 2-isopentyl-6-(pyridin-4-yl)quinoline-4-carbonitrile (138 mg, 90% yield) as a red solid: $^1$H NMR (400 MHz, CDCl$_3$) δ 8.80 (d, J=5.5 Hz, 2H), 8.40 (d, J=1.8 Hz, 1H), 8.28 (d, J=8.8 Hz, 1H), 8.12 (dd, J=8.8, 2.0 Hz, 1H), 7.72-7.76 (m, 3H), 3.05-3.11 (m, 2H), 1.68-1.80 (m, 3H), 1.03 (d, J=6.3 Hz, 6H); LCMS (ESI) m/e 302.1 [(M+H)$^+$, calcd for C$_{20}$H$_{20}$N$_3$ 302.2].

Example 7

(−)-(R)-2-(1-Amino-3-methylbutyl)-6-(pyridin-4-yl)quinoline-4-carbonitrile

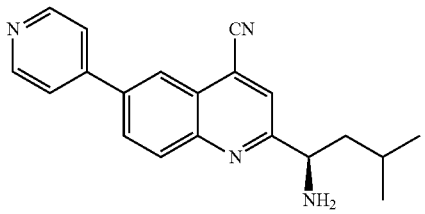 [SMILES: CC(C)C[C@@H](N)c1cc(C#N)c2cc(-c3ccncc3)ccc2n1]

Part A. 2-(1-Bromo-3-methylbutyl)-6-(pyridin-4-yl)quinoline-4-carbonitrile

To a solution of 2-isopentyl-6-(pyridin-4-yl)quinoline-4-carbonitrile (500 mg, 1.66 mmol) and AIBN (136 mg, 0.830 mmol) in carbon tetrachloride (6 mL) was added NBS (325 mg, 1.83 mmol). The reaction mixture was then heated at 75° C. for 3.5 h. Additional NBS (110 mg) and AIBN (60 mg) was added and stirring was continued for an additional 2.5 h. The mixture was cooled to room temperature and was transferred to a reparatory funnel containing saturated aqueous NaHCO$_3$ solution (10 mL). The aqueous layer was extracted with dichloromethane (3×20 mL). The combined organic layers were washed with brine (10 mL), dried over MgSO$_4$, filtered, and concentrated. The residue was purified by column chromatography on silica gel (2%→7% methanol in CH$_2$Cl$_2$) to afford 2-(1-bromo-3-methylbutyl)-6-(pyridin-4-yl)quinoline-4-carbonitrile (510 mg, 81% yield) as a brown solid: $^1$H NMR (400 MHz, CDCl$_3$) δ 8.81 (d, J=5.8 Hz, 2H), 8.42 (d, J=1.8 Hz, 1H), 8.31 (d, J=8.5 Hz, 1H), 8.15 (dd, J=8.8, 2.0 Hz, 1H), 8.03 (s, 1H), 7.73 (dd, J=4.5, 1.5 Hz, 2H), 5.28-5.34 (m, J=8.8, 6.8 Hz, 1H), 2.32-2.40 (m, 1H), 2.15 (dt, J=14.3, 7.2 Hz, 1H), 1.79-1.88 (m, 1H), 1.05 (d, J=6.5 Hz, 3H), 1.01 (d, J=6.5 Hz, 3H); LCMS (ESI) m/e 380.0 [(M+H)$^+$, calcd for C$_{20}$H$_{19}$BrN$_3$ 380.1]; LCMS (ESI) m/e 380.0 [(M+H)$^+$, calcd for C$_{20}$H$_{19}$BrN$_3$ 380.1].

Part B. 2-(1-Azido-3-methylbutyl)-6-(pyridin-4-yl)quinoline-4-carbonitrile

A solution of 2-(1-bromo-3-methylbutyl)-6-(pyridin-4-yl)quinoline-4-carbonitrile (700 mg, 1.841 mmol) in acetone (1 mL) in a conical vial was treated with sodium azide (1.20 g, 18.41 mmol). The mixture was heated at 70° C. for 3 h. The reaction mixture was transferred to a separatory funnel containing water (20 mL). The aqueous layer was extracted with dichloromethane (3×20 mL). The combined organic layers were washed with brine (20 mL), dried over MgSO$_4$, filtered, and concentrated. The residue was purified by column chromatography on silica gel (1%→3% methanol in CH$_2$Cl$_2$) to afford 2-(1-azido-3-methylbutyl)-6-(pyridin-4-yl)quinoline-4-carbonitrile (480 mg, 76% yield) as a brown oil: $^1$H NMR (400 MHz, CDCl$_3$) δ 8.80 (dd, J=4.5, 1.5 Hz, 2H), 8.43 (d, J=1.8 Hz, 1H), 8.33 (d, J=9.3 Hz, 1H), 8.16 (dd, J=8.8, 2.0 Hz, 1H), 7.89 (s, 1H), 7.70 (dd, J=4.5, 1.8 Hz, 2H), 4.82 (dd, J=9.0, 5.5 Hz, 1H), 1.91-2.00 (m, 1H), 1.75-1.85 (m, 2H), 1.06 (d, J=2.5 Hz, 3H), 1.04 (d, J=2.5 Hz, 3H); LCMS (ESI) m/e 343.1 [(M+H)$^+$, calcd for C$_{20}$H$_{19}$N$_6$ 343.2].

The enantiomers were separated by chiral chromatography (ChiralCel AD-H column, 30×250 mm, 5 μm, 15% methanol with 0.1% diethylamine/85% CO$_2$, 150 bar, 35° C., 70 mL/min, λ=260 nm):

Peak 1:
$^1$H NMR (400 MHz, CDCl$_3$) δ 8.80 (dd, J=4.5, 1.5 Hz, 2H), 8.43 (d, J=1.8 Hz, 1H), 8.33 (d, J=9.3 Hz, 1H), 8.16 (dd, J=8.8, 2.0 Hz, 1H), 7.89 (s, 1H), 7.70 (dd, J=4.5, 1.8 Hz, 2H), 4.82 (dd, J=9.0, 5.5 Hz, 1H), 1.91-2.00 (m, 1H), 1.75-1.85 (m, 2H), 1.06 (d, J=2.5 Hz, 3H), 1.04 (d, J=2.5 Hz, 3H);

Peak 2:
$^1$H NMR (400 MHz, CDCl$_3$) δ 8.80 (dd, J=4.5, 1.5 Hz, 2H), 8.43 (d, J=1.8 Hz, 1H), 8.33 (d, J=9.3 Hz, 1H), 8.16 (dd, J=8.8, 2.0 Hz, 1H), 7.89 (s, 1H), 7.70 (dd, J=4.5, 1.8 Hz, 2H), 4.82 (dd, J=9.0, 5.5 Hz, 1H), 1.91-2.00 (m, 1H), 1.75-1.85 (m, 2H), 1.06 (d, J=2.5 Hz, 3H), 1.04 (d, J=2.5 Hz, 3H);

Part C. 2-(1-Amino-3-methylbutyl)-6-(pyridin-4-yl)quinoline-4-carbonitrile

A solution of 2-(1-azido-3-methylbutyl)-6-(pyridin-4-yl)quinoline-4-carbonitrile (Peak 1 from Part B) (90 mg, 0.263 mmol) in THF (4 mL) was treated with triphenylphosphine (138 mg, 0.526 mmol). The mixture was stirred at room temperature for 3 h. Water (0.2 mL) was added and the mixture was heated at 50° C. for 24 h. The reaction mixture was concentrated and the product was purified by reverse phase HPLC (5% MeCN:95% water→95% MeCN:5% water with 0.1% TFA). The organic solvent was removed under reduced pressure and the aqueous mixture was frozen and placed on the lyophilizer to afford (−)-(R)-2-(1-amino-3-methylbutyl)-6-(pyridin-4-yl)quinoline-4-carbonitrile (75 mg, 52% yield) as a TFA salt: [α]$^{22}_D$-3.81 (c 0.105, MeOH); $^1$H NMR (400 MHz, DMSO-d$_6$) δ 8.84-8.87 (m, 2H), 8.59 (br s, 3H), 8.46-8.50 (m, 2H), 8.45 (s, 1H), 8.37 (d, J=8.8 Hz, 1H), 8.08-8.12 (m, 2H), 4.72-4.79 (m, 1H), 1.78-1.95 (m, 2H), 1.62 (dt, J=13.2, 6.6 Hz, 1H), 0.95 (dd, J=6.4, 4.4 Hz, 6H); LCMS (ESI) m/e 317.2 [(M+H)$^+$, calcd for C$_{20}$H$_{21}$N$_4$ 317.2]. The absolute stereochemistry was determined by X-ray crystallography.

Example 8

(+)-(S)-2-(1-Amino-3-methylbutyl)-6-(pyridin-4-yl)quinoline-4-carbonitrile

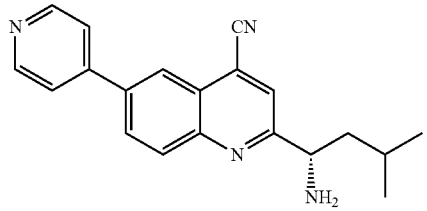 [SMILES: CC(C)C[C@H](N)c1cc(C#N)c2cc(-c3ccncc3)ccc2n1]

A solution of 2-(1-azido-3-methylbutyl)-6-(pyridin-4-yl)quinoline-4-carbonitrile (Peak 2 from Example 7 Part B) (80 mg, 0.234 mmol) in THF (4 mL) was treated with triphenylphosphine (123 mg, 0.467 mmol). The mixture was stirred at room temperature for 3 h. Water (0.2 mL) was added and the mixture was heated at 50° C. for 24 h. The reaction mixture was concentrated and the product was purified by reverse phase HPLC (5% MeCN:95% water→95% MeCN:5% water with 0.1% TFA). The organic solvent was removed under reduced pressure and the aqueous mixture was frozen and placed on the lyophilizer to afford (+)-(S)-2-(1-amino-3-methylbutyl)-6-(pyridin-4-yl)quinoline-4-carbonitrile (61 mg, 48% yield) as a TFA salt: $[\alpha]^{22}_D$ 3.64 (c 0.055, MeOH); $^1$H NMR (400 MHz, DMSO-$d_6$) δ 8.84-8.87 (m, 2H), 8.59 (br s, 3H), 8.46-8.50 (m, 2H), 8.45 (s, 1H), 8.37 (d, J=8.8 Hz, 1H), 8.08-8.12 (m, 2H), 4.72-4.79 (m, 1H), 1.78-1.95 (m, 2H), 1.62 (dt, J=13.2, 6.6 Hz, 1H), 0.95 (dd, J=6.4, 4.4 Hz, 6H); LCMS (ESI) m/e 317.2 [(M+H)$^+$, calcd for $C_{20}H_{21}N_4$ 317.2]. The absolute stereochemistry was determined by X-ray crystallography.

Example 9

2-Isopentyl-7-methoxy-6-(oxazol-5-yl)quinolin-4-ol

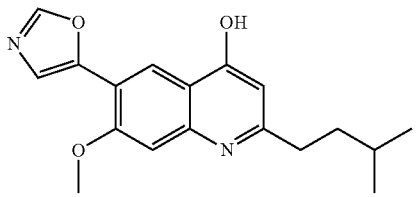 [SMILES: COc1cc2nc(CCC(C)C)cc(O)c2cc1-c1cnco1]

Part A. 5-(2-Methoxy-4-nitrophenyl)oxazole

To a solution of 2-methoxy-4-nitrobenzaldehyde (700 mg, 3.86 mmol) and TosMIC (754 mg, 3.86 mmol) in MeOH (7 mL) was added potassium carbonate (561 mg, 4.06 mmol). The reaction mixture was heated at reflux for 3 h. The reaction mixture was cooled to room temperature and was transferred to a reparatory funnel containing saturated aqueous NaHCO$_3$ solution (25 mL). The aqueous layer was extracted with ethyl acetate (3×50 mL). The combined organic layers were washed with brine (25 mL), dried over MgSO$_4$, filtered and concentrated. The residue was purified by column chromatography on silica gel (30%→40% ethyl acetate in hexanes) to afford 5-(2-methoxy-4-nitrophenyl)oxazole (732 mg, 86% yield) as a yellow solid: $^1$H NMR (400 MHz, CDCl$_3$) δ 7.98 (s, 1H), 7.93 (d, J=1.8 Hz, 1H), 7.92 (s, 1H), 7.84 (d, J=1.8 Hz, 1H), 7.75 (s, 1H), 4.08 (s, 3H); LC/MS (ESI) m/e 221.3 [(M+H)$^+$, calcd for $C_{10}H_9N_2O_4$ 221.1].

Part B. 3-Methoxy-4-(oxazol-5-yl)aniline 5-(2-Methoxy-4-nitrophenyl)oxazole (700 mg, 3.18 mmol) was dissolved in EtOH (30 mL) and CHCl$_3$ (15 mL) in a Parr bottle. 10% Palladium on carbon (677 mg, 0.318 mmol, Degussa type) was added and the mixture was placed on the Parr shaker under H$_2$ at 40 psi for 1.5 h. The catalyst was removed by filtration through a pad of diatomaceous earth (Celite®) and the filtrate was concentrated. The product was crystallized from ethyl acetate/ethanol to afford 3-methoxy-4-(oxazol-5-yl)aniline (496 mg, 82% yield) as a gray solid: $^1$H NMR (400 MHz, DMSO-$d_6$) δ 8.34 (s, 1H), 7.55 (d, J=8.3 Hz, 1H), 7.37 (s, 1H), 6.70 (s, 1H), 6.63 (d, J=8.1 Hz, 1H), 3.89 (s, 3H); LC (ESI) m/e 191.3 [(M+H)$^+$, calcd for $C_{10}H_{11}N_2O_2$ 191.1].

Part C. (E)-Methyl 3-(3-methoxy-4-(oxazol-5-yl)phenylamino)-6-methylhept-2-enoate To a solution of 3-methoxy-4-(oxazol-5-yl)aniline (2.65 g, 13.94 mmol) and methyl 6-methyl-3-oxoheptanoate (2.40 g, 13.94 mmol) in toluene (15 mL) was added acetic acid (0.798 mL, 13.94 mmol) and 4 Å molecular sieves (3.5 g). The mixture was heated at 85° C. for 24 h. (After heating for 2 h, ethanol (3.0 mL) was added due to the poor solubility of the starting material in toluene.) The mixture was cooled to room temperature, filtered through a pad of diatomaceous earth (Celite®), and the filtrate was concentrated. The residue was purified by column chromatography on silica gel (20%→80% ethyl acetate in hexanes) to afford (E)-methyl 3-(3-methoxy-4-(oxazol-5-yl)phenylamino)-6-methylhept-2-enoate (1.57 g, 33% yield) as a pale yellow oil: $^1$H NMR (400 MHz, CDCl$_3$) δ 10.45 (br s, 1H), 7.92 (s, 1H), 7.71-7.75 (m, 1H), 7.54 (s, 1H), 6.81 (dd, J=8.3, 2.0 Hz, 1H), 6.70 (d, J=2.0 Hz, 1H), 4.80 (br s, 1H), 3.97 (s, 3H), 3.72 (s, 3H), 2.37-2.45 (m, 2H), 1.54 (dt, J=13.3, 6.7 Hz, 1H), 1.35-1.43 (m, 2H), 0.84 (d, J=6.8 Hz, 6H).

Part D. 2-Isopentyl-7-methoxy-6-(oxazol-5-yl)quinolin-4-ol

A mixture of phenyl ether (25 mL) and methyl (E)-methyl 3-(3-methoxy-4-(oxazol-5-yl)phenylamino)-6-methylhept-2-enoate (1.34 g, 3.89 mmol) in a 25 mL round bottom flask was heated at 250° C. for 45 min. The reaction was monitored by LCMS. The mixture was cooled down to 40° C. in a separate oil bath and was transferred to a flask containing hexanes (110 mL) at 40° C. The solid was collected on Buchner funnel and was washed with hexanes to give 2-isopentyl-7-methoxy-6-(oxazol-5-yl)quinolin-4-ol (1.01 g, 79% yield) as a brown solid: $^1$H NMR (400 MHz, DMSO-$d_6$) δ 11.49 (s, 1H), 8.48 (s, 1H), 8.35 (s, 1H), 7.58 (s, 1H), 7.10 (s, 1H), 5.90 (d, J=1.5 Hz, 1H), 4.04 (s, 3H), 2.55-2.63 (m, 2H), 1.53-1.64 (m, 3H), 0.95 (d, J=6.3 Hz, 6H); LCMS (ESI) m/e 313.1 [(M+H)$^+$, calcd for $C_{18}H_{21}N_2O_3$ 313.2].

Example 10

5-(4-Bromo-2-isopentyl-7-methoxyquinolin-6-yl)oxazole

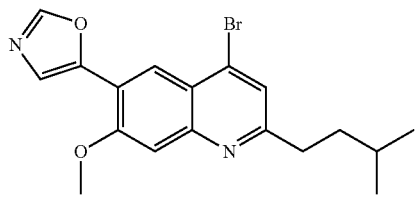 [SMILES: COc1cc2nc(CCC(C)C)cc(Br)c2cc1-c1cnco1]

To a suspension of 2-Isopentyl-7-methoxy-6-(oxazol-5-yl)quinolin-4-ol (2.14 g, 2.60 mmol), prepared as described in Example 9, in dichloroethane (25 mL) at room temperature was added phosphorous oxybromide (7.46 g, 26.0 mmol) followed by DMF (0.202 mL, 2.60 mmol). The mixture was heated at 65° C. for 23 h. The mixture was cooled to room temperature and was transferred to a reparatory funnel containing saturated aqueous NaHCO$_3$ solution (50 mL). The aqueous layer was extracted with 5% methanol in dichloromethane (4×100 mL). The combined organic layers were washed with brine (50 mL), dried over MgSO$_4$, filtered, and concentrated. The residue was purified by column chromatography on silica gel (2%→7% methanol in dichloromethane) to afford 5-(4-bromo-2-isopentyl-7-methoxyquinolin-6-yl)oxazole (414 mg, 42% yield) as a tan solid: $^1$H NMR (400 MHz, CDCl$_3$) δ 8.52 (s, 1H), 8.04 (s, 1H), 7.74 (s, 1H), 7.54 (s, 1H), 7.50 (br. s., 1H), 4.14 (s, 3H), 2.95 (br. s., 2H), 1.63-1.77 (m, 3H), 1.01 (d, J=6.3 Hz, 6H); LCMS (ESI) m/e 375.0 [(M+H)$^+$, calcd for C$_{18}$H$_{20}$BrN$_2$O$_2$ 375.1].

Example 11

2-Isopentyl-7-methoxy-6-(oxazol-5-yl)quinoline-4-carbonitrile

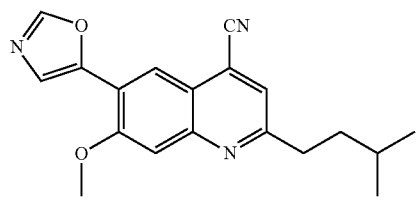 [SMILES: COc1cc2nc(CCC(C)C)cc(C#N)c2cc1-c1cnco1]

5-(4-Bromo-2-isopentyl-7-methoxyquinolin-6-yl)oxazole (425 mg, 1.133 mmol), prepared as described in Example 10, was dissolved in DMF (10 mL) and water (0.5 mL). The mixture was degassed by sonication for several minutes. Zinc cyanide (140 mg, 1.189 mmol), Pd$_2$(dba)$_3$ (51.9 mg, 0.057 mmol), and dppf (62.8 mg, 0.113 mmol) were added and the reaction mixture was heated at 120° C. under N$_2$ for 45 min. The mixture was cooled to room temperature and was transferred to a reparatory funnel containing ether (250 mL) and the organic layer was washed with water (5×25 mL) to remove any residual DMF. The combined organic layers were washed with brine (25 mL), dried over MgSO$_4$, filtered, and concentrated. The residue was purified by column chromatography on silica gel (1%→4% methanol in dichloromethane) to afford 2-isopentyl-7-methoxy-6-(oxazol-5-yl)quinoline-4-carbonitrile (340 mg, 92% yield) as a tan solid: $^1$H NMR (400 MHz, CDCl$_3$) δ 8.51 (s, 1H), 8.06 (s, 1H), 7.79 (s, 1H), 7.59 (br s, 1H), 7.56 (s, 1H), 4.16 (s, 3H), 3.00-3.06 (m, 2H), 1.68-1.77 (m, 3H), 1.02 (d, J=6.3 Hz, 6H); LCMS (ESI) m/e 322.1 [(M+H)$^+$, calcd for C$_{19}$H$_{20}$N$_3$O$_2$ 322.2].

Example 12 and Example 13

(−)-2-(1-Amino-3-methylbutyl)-7-methoxy-6-(oxazol-5-yl)quinoline-4-carbonitrile (Example 12)

(+)-2-(1-Amino-3-methylbutyl)-7-methoxy-6-(oxazol-5-yl)quinoline-4-carbonitrile (Example 13)

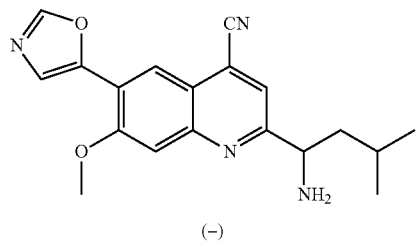

(−)

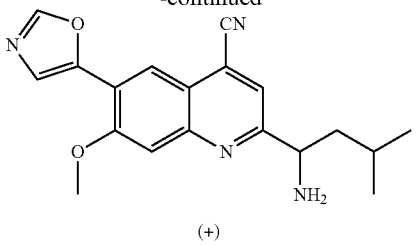

(+)

Part A. 2-(1-Bromo-3-methylbutyl)-7-methoxy-6-(oxazol-5-yl)quinoline-4-carbonitrile To a solution of 2-isopentyl-7-methoxy-6-(oxazol-5-yl)quinoline-4-carbonitrile (268 mg, 0.834 mmol), prepared as described in Example 11, in carbon tetrachloride (8 mL) was added N-bromosuccinimide (163 mg, 0.917 mmol) and AIBN (27.4 mg, 0.167 mmol). The reaction mixture was then heated at 75° C. for 1.5 h. The mixture was cooled to room temperature and was transferred to a separatory funnel containing saturated aqueous NaHCO$_3$ solution (10 mL). The aqueous layer was extracted with dichloromethane (3×20 mL). The combined organic layers were washed with brine (10 mL), dried over MgSO$_4$, filtered, and concentrated. The residue was purified by column chromatography on silica gel (1%→3% methanol in dichloromethane) to give 2-(1-bromo-3-methylbutyl)-7-methoxy-6-(oxazol-5-yl)quinoline-4-carbonitrile (318 mg, 86% yield) as a yellow solid: $^1$H NMR (400 MHz, CDCl$_3$) δ 8.54 (s, 1H), 8.08 (s, 1H), 7.83 (s, 1H), 7.82 (s, 1H), 7.60 (s, 1H), 5.26 (dd, J=9.0, 6.8 Hz, 1H), 4.18 (s, 3H), 2.30-2.39 (m, 1H), 2.06-2.17 (m, 1H), 1.79-1.88 (m, 1H), 1.04 (d, J=6.5 Hz, 3H), 1.01 (d, J=6.5 Hz, 3H); LCMS (ESI) m/e 400.0 [(M+H)$^+$, calcd for C$_{19}$H$_{19}$BrN$_3$O$_2$ 400.1].

Part B. 2-(1-Azido-3-methylbutyl)-7-methoxy-6-(oxazol-5-yl)quinoline-4-carbonitrile A solution of 2-(1-bromo-3-methylbutyl)-7-methoxy-6-(oxazol-5-yl)quinoline-4-carbonitrile (282 mg, 0.705 mmol) in acetone (7 mL) was treated with sodium azide (458 mg, 7.05 mmol). The mixture was heated at 70° C. for 2 h. The reaction mixture was transferred to a separatory funnel containing water (25 mL). The aqueous layer was extracted with dichloromethane (3×50 mL). The combined organic layers were washed with brine (20 mL), dried over MgSO$_4$, filtered, and concentrated. The residue was purified by column chromatography on silica gel (1%→3% methanol in dichloromethane) to afford 2-(1-azido-3-methylbutyl)-7-methoxy-6-(oxazol-5-yl)quinoline-4-carbonitrile (189 mg, 71% yield) as a yellow solid: $^1$H NMR (400 MHz, CDCl$_3$) δ 8.55 (s, 1H), 8.08 (s, 1H), 7.82 (s, 1H), 7.69 (s, 1H), 7.61 (s, 1H), 4.75 (dd, J=9.2, 5.4 Hz, 1H), 4.19 (s, 3H), 1.89-1.99 (m, 1H), 1.75-1.87 (m, 2H), 1.05 (d, J=2.8 Hz, 3H), 1.03 (d, J=2.8 Hz, 3H); LCMS (ESI) m/e 363.1 [(M+H)$^+$, calcd for C$_{19}$H$_{19}$N$_6$O$_2$ 363.2].

Part C. 2-(1-Amino-3-methylbutyl)-7-methoxy-6-(oxazol-5-yl)quinoline-4-carbonitrile A solution of 2-(1-azido-3-methylbutyl)-7-methoxy-6-(oxazol-5-yl)quinoline-4-carbonitrile (114 mg, 0.315 mmol) in THF (5.0 mL) was treated with triphenylphosphine (165 mg, 0.629 mmol). The mixture was stirred at room temperature for 3 h. Water (0.25 mL) was added and the mixture was heated at 50° C. for 24 h. The reaction mixture was cooled to room temperature and was concentrated. The product was purified by reverse phase HPLC (5% MeCN:95% water→95% MeCN:5% water with 0.1% TFA). The organic solvent was removed under reduced pressure and the aqueous mixture was frozen and placed on the lyophilizer to afford 2-(1-amino-3-methylbutyl)-7-methoxy-6-(oxazol-5-yl)quinoline-4-carbonitrile (96 mg, 68% yield) as a TFA salt: $^1$H NMR (500 MHz, DMSO-$d_6$) δ 8.67 (s, 1H), 8.51 (br s, 3H), 8.39 (s, 1H), 8.22 (s, 1H), 7.93 (s, 1H), 7.67 (s, 1H), 4.64-4.70 (m, 1H), 4.19 (s, 3H), 1.85-1.93 (m, 1H), 1.77-1.84 (m, 1H), 1.54-1.63 (m, 1H), 0.96 (d, J=6.1 Hz, 3H), 0.93 (d, J=6.4 Hz, 3H); LCMS (ESI) m/e 337.1 [(M+H)$^+$, calcd for $C_{19}H_{21}N_4O_2$ 337.2].

The enantiomers were separated by chiral chromatography (ChiralCel OJ-H column, 30×250 mm, 5 μm, 10% methanol with 0.1% diethylamine/90% $CO_2$, 120 bar, 35° C., 70 mL/min, λ=270 nm):

Example 12 (Peak 1)

$[α]^{22}_D$ −0.54 (c 1.63, MeOH); $^1$H NMR (400 MHz, CDCl$_3$) δ 8.52 (s, 1H), 8.06 (s, 1H), 7.79 (s, 1H), 7.73 (s, 1H), 7.59 (s, 1H), 4.27 (t, J=7.2 Hz, 1H), 4.17 (s, 3H), 1.78-1.70 (m, 1H), 1.70-1.64 (m, 2H), 1.02 (d, J=4.3 Hz, 3H), 1.00 (d, J=4.0 Hz, 3H); LCMS (ESI) m/e 337.1 [(M+H)$^+$, calcd for $C_{19}H_{21}N_4O_2$ 337.2].

Example 13 (Peak 2)

$[α]^{22}_D$ 1.19 (c 1.63, MeOH); $^1$H NMR (400 MHz, CDCl$_3$) δ 8.52 (s, 1H), 8.06 (s, 1H), 7.80 (s, 1H), 7.73 (s, 1H), 7.59 (s, 1H), 4.27 (t, J=7.2 Hz, 1H), 4.17 (s, 3H), 1.79-1.70 (m, 1H), 1.69-1.64 (m, 2H), 1.02 (d, J=4.0 Hz, 3H), 1.00 (d, J=4.0 Hz, 3H); LCMS (ESI) m/e 337.1 [(M+H)$^+$, calcd for $C_{19}H_{21}N_4O_2$ 337.2].

Example 14

3-Isobutyl-2-methyl-6-(pyridin-4-yl)quinolin-4-ol

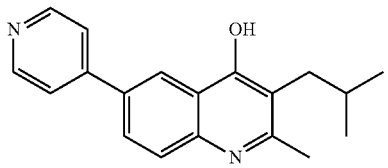 [SMILES: Cc1nc2ccc(-c3ccncc3)cc2c(O)c1CC(C)C]

Part A.
6-Bromo-3-isobutyl-2-methylquinolin-4(1H)-one

A mixture of 2-amino-5-bromobenzoic acid (4.00 g, 18.52 mmol) and 5-methylhexan-2-one (3.17 g, 27.8 mmol) in phosphorus oxychloride (15.0 mL, 161 mmol) was heated at 100° C. for 2 h. The mixture was cooled to room temperature and was concentrated. The residue was transferred to a beaker and was treated with ice and solid NaHCO$_3$ until pH=7-8. The mixture was diluted with water (100 mL) and was transferred to a separatory funnel. The aqueous layer was extracted with ethyl acetate (3×100 mL). The combined organic layers were washed with brine (100 mL), dried over MgSO$_4$, filtered, and concentrated. The residue was purified by column chromatography on silica gel (2%→4%→6% MeOH in CH$_2$Cl$_2$) to afford 6-bromo-2-isopentylquinolin-4(1H)-one (1.015 g) as a yellow solid. At the top of the aqueous layer from the extractions was a flocculent mixture. After removal of most of the aqueous layer, the flocculent mixture was poured into a separate flask and a yellow solid was collected, washed with water followed by minimal ethyl acetate, and dried under vacuum to give a yellow solid (45 mg). $^1$H NMR and LCMS indicated that the products isolated by column chromatography and by filtration were identical. The total amount of 6-bromo-2-isopentylquinolin-4(1H)-one obtained was (1.06 g, 19% yield): $^1$H NMR (400 MHz, DMSO-$d_6$) δ 11.53 (s, 1H), 8.13 (d, J=2.5 Hz, 1H), 7.72 (dd, J=8.9, 2.4 Hz, 1H), 7.46 (d, J=8.8 Hz, 1H), 2.40 (s, 3H), 2.40 (d, J=5.3 Hz, 2H), 1.87 (dt, J=13.6, 6.9 Hz, 1H), 0.87 (d, J=6.8 Hz, 6H); LCMS (ESI) m/e 294.0 [(M+H)$^+$, calcd for $C_{14}H_{17}BrNO$ 294.0].

Part B. 3-Isobutyl-2-methyl-6-(pyridin-4-yl)quinolin-4-ol

To a solution of 6-bromo-3-isobutyl-2-methylquinolin-4 (1H)-one (200 mg, 0.680 mmol) in toluene (4 mL) and ethanol (1 mL) was added pyridin-4-ylboronic acid (84 mg, 0.680 mmol) and a 1 M aqueous solution of sodium carbonate (0.816 mL, 0.816 mmol). The solution was degassed with N$_2$ for several minutes. Pd(PPh$_3$)$_4$ (79 mg, 0.068 mmol) was then added and the mixture was heated at 95° C. for 12 h. The reaction mixture was diluted with CH$_2$Cl$_2$ along with some methanol (to dissolve the solids) and was transferred to a separatory funnel containing saturated aqueous NaHCO$_3$ solution (15 mL). The aqueous layer was extracted with CH$_2$Cl$_2$ (3×20 mL). The combined organic layers were washed with brine (15 mL), dried over MgSO$_4$, filtered and concentrated. The residue was purified by column chromatography on silica gel (3%→8% methanol in CH$_2$Cl$_2$) to afford 3-isobutyl-2-methyl-6-(pyridin-4-yl)quinolin-4-ol (55 mg, 26% yield) as a colorless solid: $^1$H NMR (400 MHz, DMSO-$d_6$) δ 8.66 (d, J=6.0 Hz, 2H), 8.44 (d, J=2.0 Hz, 1H), 8.05 (dd, J=8.7, 2.1 Hz, 1H), 7.75-7.83 (m, 2H), 7.62 (d, J=8.8 Hz, 1H), 3.33 (s, 2H), 2.42 (s, 3H), 1.85-1.96 (m, 1H), 0.89 (d, J=6.5 Hz, 7H); LCMS (ESI) m/e 293.0 [(M+H)$^+$, calcd for $C_{19}H_{21}N_2O$ 293.2].

Example 15

3-Isobutyl-6-(pyridin-4-yl)quinolin-4-ol

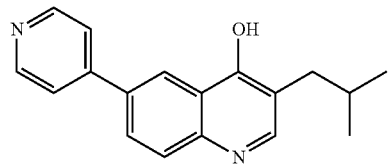 [SMILES: CC(C)Cc1cnc2ccc(-c3ccncc3)cc2c1O]

Part A. Methyl 2-formyl-4-methylpentanoate

To a solution of diisopropylamine (2.85 mL, 19.97 mmol) in THF (65 mL) at −78° C. was added n-butyllithium (12.48 mL, 19.97 mmol) via syringe. The reaction mixture was warmed up to 0° C. for 15 min. The reaction mixture was then cooled to −78° C. and methyl 4-methylpentanoate (2.00 g, 15.36 mmol) dissolved in THF (15 mL) was added via cannula. The reaction mixture was stirred for 30 min at −78° C. Ethyl formate (1.479 g, 19.97 mmol) dissolved in THF (5 mL) was then added via cannula. The reaction mixture was stirred for an additional 4 h while allowing the mixture to warm up to room temperature. The reaction was quenched by the addition of water (50 mL). The reaction mixture was transferred to a separatory funnel containing water (50 mL). The aqueous layer was washed with hexanes (2×125 mL) to remove impurities. The aqueous layer was acidified with 10% HCl (15 mL). The aqueous layer was extracted with CH$_2$Cl$_2$ (3×100 mL). The combined organic layers were washed with brine (50 mL), dried over MgSO$_4$, filtered, and concentrated. The residue was purified by column chromatography on silica gel (5%→20% ethyl acetate in hexanes) to afford methyl 2-formyl-4-methylpentanoate (1.24 g, 51% yield) as a colorless oil: LCMS (ESI) m/e 159.0 [(M+H)$^+$, calcd for C$_8$H$_{15}$O$_3$ 159.1].

Part B. (E)-Methyl 2-(((4-bromophenyl)amino)methylene)-4-methylpentanoate

A mixture of 4-bromoaniline (544 mg, 3.16 mmol) and methyl 2-formyl-4-methylpentanoate (500 mg, 3.16 mmol) in ethanol (9 mL) was heated at 75° C. for 14 h. The mixture was cooled to room temperature and was concentrated. The residue was purified by column chromatography on silica gel (10%→20% ethyl acetate in hexanes) to afford (E)-methyl 2-((4-bromophenylamino)methylene)-4-methylpentanoate (763 mg, 77% yield) as a colorless oil: $^1$H NMR (400 MHz, CDCl$_3$) δ 7.91 (d, J=13.6 Hz, 1H), 7.41 (d, J=8.8 Hz, 2H), 6.85 (d, J=8.8 Hz, 2H), 6.16 (d, J=13.3 Hz, 1H), 3.75 (s, 3H), 2.18 (d, J=7.3 Hz, 2H), 1.86 (dt, J=13.4, 6.8 Hz, 1H), 0.96 (d, J=6.5 Hz, 6H); LCMS (ESI) m/e 312.0 [(M+H)$^+$, calcd for C$_{14}$H$_{19}$BrNO$_2$ 312.1].

Part C. 6-Bromo-3-isobutylquinolin-4(1H)-one

A mixture of diphenyl ether (4 mL) and (E)-methyl 2-((4-bromophenylamino)methylene)-4-methylpentanoate (250 mg, 0.801 mmol) was heated at 240° C. for 1 h. The mixture was cooled to 40° C. in a separate oil bath and hexanes (20 mL) was added. The solid was collected on Buchner funnel and was washed with warm hexanes to give 6-bromo-3-isobutylquinolin-4(1H)-one (120 mg, 54% yield) as an off-white solid: $^1$H NMR (400 MHz, DMSO-d$_6$) δ 11.81 (br. s., 1H), 8.19 (d, J=2.3 Hz, 1H), 7.86 (s, 1H), 7.75 (dd, J=8.9, 2.4 Hz, 1H), 7.51 (d, J=9.0 Hz, 1H), 2.31 (d, J=7.0 Hz, 2H), 1.92 (dt, J=13.6, 6.8 Hz, 1H), 0.86 (d, J=6.5 Hz, 6H); LCMS (ESI) m/e 280.0 [(M+H)$^+$, calcd for C$_{13}$H$_{15}$BrNO 280.0].

Part D. 3-Isobutyl-6-(pyridin-4-yl)quinolin-4-ol

To a solution of 6-bromo-3-isobutylquinolin-4(1H)-one (115 mg, 0.410 mmol) in toluene (2 mL) and ethanol (0.5 mL) was added pyridin-4-ylboronic acid (50.5 mg, 0.410 mmol) and 1M aqueous sodium carbonate solution (0.493 mL, 0.493 mmol). The solution was degassed with N$_2$ for several minutes. Pd(PPh$_3$)$_4$ (47.4 mg, 0.041 mmol) was then added and the mixture was heated at 95° C. for 14 h. The reaction mixture was diluted with 5% MeOH in CH$_2$Cl$_2$ and was transferred to a separatory funnel containing saturated aqueous NaHCO$_3$ solution (15 mL). The aqueous layer was extracted with 5% MeOH in CH$_2$Cl$_2$ (3×15 mL). The combined organic layers were washed with brine (15 mL), dried over MgSO$_4$, filtered and concentrated. The solids that formed in the aqueous layer from the above extraction were collected on a Buchner funnel and were suspended in a mixture of warm methanol and CH$_2$Cl$_2$. The suspension was filtered and the filtrate was combined with the crude product from the organic layer. The residue was purified by column chromatography on silica gel (4%→8% methanol in CH$_2$Cl$_2$) to afford 3-isobutyl-6-(pyridin-4-yl)quinolin-4-ol (38 mg, 32% yield) as a colorless solid: $^1$H NMR (400 MHz, DMSO-d$_6$) δ 8.66 (dd, J=4.5, 1.5 Hz, 2H), 8.49 (d, J=2.0 Hz, 1H), 8.07 (dd, J=8.8, 2.3 Hz, 1H), 7.86 (s, 1H), 7.76-7.80 (m, 2H), 7.66 (d, J=8.8 Hz, 1H), 5.77 (s, 1H), 2.34 (d, J=7.0 Hz, 2H), 1.96 (dt, J=13.6, 6.8 Hz, 1H), 0.88 (d, J=6.5 Hz, 6H); LCMS (ESI) m/e 279.2 [(M+H)$^+$, calcd for C$_{18}$H$_{19}$N$_2$O 279.1].

Example 16

3-Bromo-2-isopentyl-6-(pyridin-4-yl)quinolin-4-ol

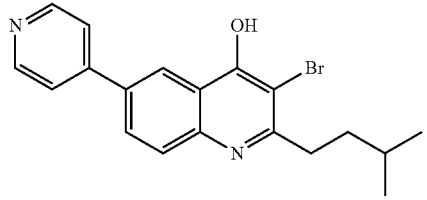 [SMILES: CC(C)CCc1nc2ccc(-c3ccncc3)cc2c(O)c1Br]

To solution of 2-isopentyl-6-(pyridin-4-yl)quinolin-4 (1H)-one (175 mg, 0.599 mmol), prepared as described in Example 1, in acetic acid (4 mL) at room temperature was added bromine (0.034 mL, 0.658 mmol). The reaction mixture was stirred at room temperature for 1 h. The mixture was diluted with water (12 mL) and the solid was collected on a Buchner funnel followed by washing with water then ether. The solid was placed under vacuum to give 3-bromo-2-isopentyl-6-(pyridin-4-yl)quinolin-4-ol (222 mg, 84% yield) as a yellow solid: $^1$H NMR (400 MHz, DMSO-d$_6$) δ 12.40 (s, 1H), 8.94 (d, J=6.8 Hz, 2H), 8.68 (d, J=2.0 Hz, 1H), 8.41 (d, J=6.5 Hz, 2H), 8.32 (dd, J=8.8, 2.3 Hz, 1H), 7.81 (d, J=8.8 Hz, 1H), 2.89-2.95 (m, 2H), 1.67-1.75 (m, 1H), 1.58-1.65 (m, 2H), 1.00 (d, J=6.5 Hz, 6H); LCMS (ESI) m/e 371.1 [(M+H)$^+$, calcd for C$_{19}$H$_{20}$BrN$_2$O 371.1].

Example 17

2-Isopentyl-6-(pyridin-4-yl)quinoline-3-carboxamide

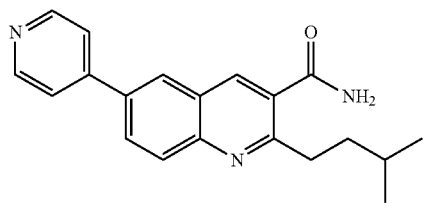 [SMILES: CC(C)CCc1nc2ccc(-c3ccncc3)cc2cc1C(N)=O]

Part A. Methyl 6-bromo-2-isopentylquinoline-3-carboxylate

To a solution of DMF (0.339 mL, 4.38 mmol) in DCE (10 mL) at 0° C. was added phosphorus oxychloride (0.429 mL, 4.60 mmol) dropwise via syringe. The cooling bath was removed and the reaction mixture was stirred at room temperature for 30 min. A solution of (E)-methyl 3-(4-bromophenylamino)-6-methylhept-2-enoate (1.43 g, 4.38 mmol), prepared as described in Example 1 Parts A-B, in DCE (8 mL) was added via cannula and the reaction mixture was heated at reflux for 3.5 h. The reaction mixture was cooled to room temperature and was transferred to a reparatory funnel containing saturated aqueous NaHCO$_3$ solution (25 mL). The aqueous layer was extracted with dichloromethane (3×25 mL). The combined organic layers were washed with brine (25 mL), dried over MgSO$_4$, filtered, and concentrated. The residue was purified by column chromatography on silica gel (5%→20% ethyl acetate in hexanes) to afford methyl 6-bromo-2-isopentylquinoline-3-carboxylate (701 mg, 48% yield) as a colorless solid: $^1$H NMR (400 MHz, CDCl$_3$) δ 8.61 (s, 1H), 8.02 (d, J=2.3 Hz, 1H), 7.92-7.98 (m, J=9.0 Hz, 1H), 7.83-7.87 (m, J=9.0, 2.3 Hz, 1H), 4.01 (s, 3H), 3.28-3.35 (m, 2H), 1.75 (ddd, J=13.2, 6.5, 6.4 Hz, 1H), 1.62-1.69 (m, 2H), 1.01 (d, J=6.3 Hz, 6H); LCMS (ESI) m/e 336.1 [(M+H)$^+$, calcd for C$_{16}$H$_{19}$BrNO$_2$ 336.1].

Part B. 6-Bromo-2-isopentylquinoline-3-carboxylic acid

To a suspension of methyl 6-bromo-2-isopentylquinoline-3-carboxylate (740 mg, 2.201 mmol) in ethanol (8 mL) was added sodium hydroxide (10% aqueous) (2.7 mL, 2.201 mmol). The reaction mixture was heated at reflux for 30 min. The mixture was cooled to room temperature and the ethanol was removed under reduced pressure. The resulting solution was cooled to 0° C. and acidified to pH=2 with 2 M HCl (4 mL) resulting in the formation of a solid. The solution was diluted with additional water during the addition. The solid was collected on a Buchner funnel and dried under vacuum to give 6-bromo-2-isopentylquinoline-3-carboxylic acid (672 mg, 95% yield) as a colorless solid, which was used directly in the next step: $^1$H NMR (400 MHz, DMSO-d$_6$) δ 13.53 (br. s., 1H), 8.80 (s, 1H), 8.40 (s, 1H), 7.91-7.97 (m, 2H), 3.19-3.28 (m, 2H), 1.56-1.67 (m, 3H), 0.94 (d, J=6.3 Hz, 6H); LCMS (ESI) m/e 322.0 [(M+H)$^+$, calcd for C$_{15}$H$_{17}$BrNO$_2$ 322.0].

Part C. 6-Bromo-2-isopentylquinoline-3-carboxamide

To a suspension of 6-bromo-2-isopentylquinoline-3-carboxylic acid (605 mg, 1.878 mmol) in CH$_2$Cl$_2$ (15 mL) was added oxalyl chloride (0.362 mL, 4.13 mmol) and a catalytic amount of DMF (0.029 mL, 0.376 mmol). The reaction mixture was stirred at room temperature for 1 h. The mixture was concentrated and the residue was taken up in CH$_2$Cl$_2$ (10 mL). The mixture was treated with 30% ammonium hydroxide solution (3.6 mL) and the reaction mixture was stirred for 30 min. The mixture was cooled to 0° C. and the solid was collected on a Buchner funnel and was washed with water. The product was dissolved in 10% MeOH in CH$_2$Cl$_2$ (100 mL) and was transferred to a separatory funnel and was washed with 50% saturated aqueous NaHCO$_3$ solution/50% water (50 mL). The aqueous layer was extracted with 10% MeOH in CH$_2$Cl$_2$ (2×50 mL). The combined organic layers were washed with brine (50 mL), dried over MgSO$_4$, filtered, and concentrated. The product was dried under vacuum to give 6-bromo-2-isopentylquinoline-3-carboxamide (505 mg, 1.572 mmol, 84% yield) as a colorless solid, which was used directly in the next step: $^1$H NMR (400 MHz, DMSO-d$_6$) δ 8.28-8.32 (m, 2H), 8.12 (s, 1H), 7.90-7.94 (m, J=8.8 Hz, 1H), 7.86-7.90 (m, J=9.0, 2.3 Hz, 1H), 7.74 (s, 1H), 3.02-3.09 (m, 2H), 1.55-1.67 (m, 3H), 0.93 (d, J=6.5 Hz, 6H); LCMS (ESI) m/e 321.1 [(M+H)$^+$, calcd for C$_{15}$H$_{18}$BrN$_2$O 321.1].

Part D. 2-Isopentyl-6-(pyridin-4-yl)quinoline-3-carboxamide

To a solution of 6-bromo-2-isopentylquinoline-3-carboxamide (65 mg, 0.202 mmol) in dioxane (1.5 mL) and water (0.25 mL) was added pyridin-4-ylboronic acid (37.3 mg, 0.304 mmol) and cesium carbonate (132 mg, 0.405 mmol). The solution was degassed by sonication under N$_2$ for 5 min. Pd(PPh$_3$)$_4$ (23.38 mg, 0.020 mmol) was then added and the mixture was heated at 95° C. for 2.5 h. The reaction mixture was cooled to room temperature and was diluted with CH$_2$Cl$_2$ and was transferred to a separatory funnel containing saturated aqueous NaHCO$_3$ solution (20 mL). The aqueous layer was extracted with CH$_2$Cl$_2$ (3×25 mL). The combined organic layers were washed with brine (20 mL), dried over MgSO$_4$, filtered and concentrated. The residue was purified by column chromatography on silica gel (4%→10% methanol in CH$_2$Cl$_2$) to afford 2-isopentyl-6-(pyridin-4-yl)quinoline-3-carboxamide (42.4 mg, 63% yield) as a colorless solid: $^1$H NMR (400 MHz, DMSO-d$_6$) δ 8.72 (dd, J=4.6, 1.6 Hz, 2H), 8.51 (d, J=2.0 Hz, 1H), 8.41 (s, 1H), 8.22 (dd, J=8.8, 2.3 Hz, 1H), 8.15 (s, 1H), 8.10 (d, J=8.8 Hz, 1H), 7.88 (dd, J=4.5, 1.8 Hz, 2H), 7.73 (s, 1H), 3.07-3.14 (m, 2H), 1.58-1.71 (m, 3H), 0.95 (d, J=6.3 Hz, 6H); LCMS (ESI) m/e 320.1 [(M+H)$^+$, calcd for C$_{20}$H$_{22}$N$_3$O 320.2].

Example 18

2-Isopentyl-6-(pyridin-4-yl)quinoline-3-carbonitrile

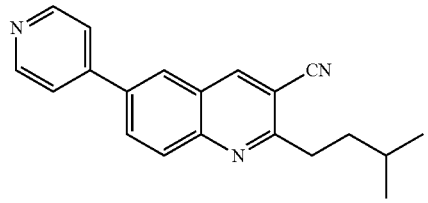 [SMILES: CC(C)CCc1nc2ccc(-c3ccncc3)cc2cc1C#N]

Part A. 6-Bromo-2-isopentylquinoline-3-carbonitrile

To a suspension of 6-bromo-2-isopentylquinoline-3-carboxamide (403 mg, 1.255 mmol), prepared as described in Example 17 Parts A-C, in CH$_2$Cl$_2$ (10 mL) at 0° C. was added triethylamine (0.525 mL, 3.76 mmol) followed by trifluoroacetic anhydride (0.222 mL, 1.568 mmol). The mixture was stirred at 0° C. for 30 min. The mixture was transferred to a separatory funnel containing saturated aqueous NaHCO$_3$ solution (25 mL). The aqueous layer was extracted with methylene chloride (3×50 mL). The combined organic layers were washed with brine (25 mL), dried over MgSO$_4$, filtered, and concentrated. The residue was purified by column chromatography on silica gel (CH$_2$Cl$_2$) to afford 6-bromo-2-isopentylquinoline-3-carbonitrile (336 mg, 88% yield) as a colorless solid: $^1$H NMR (400 MHz, CDCl$_3$) δ 8.41 (s, 1H), 8.02 (d, J=2.0 Hz, 1H), 7.96-7.99 (m, J=9.0 Hz, 1H), 7.90-7.94 (m, J=9.0, 2.0 Hz, 1H), 3.16-3.23

(m, 2H), 1.70-1.81 (m, 3H), 1.04 (d, J=6.3 Hz, 6H); LCMS (ESI) m/e 303.0 [(M+H)+, calcd for $C_{15}H_{16}BrN_2$ 303.0].

Part B. 2-Isopentyl-6-(pyridin-4-yl)quinoline-3-carbonitrile

To a solution of 6-bromo-2-isopentylquinoline-3-carbonitrile (324 mg, 1.069 mmol) in dioxane (8 mL) and water (1 mL) was added pyridin-4-ylboronic acid (197 mg, 1.603 mmol) and cesium carbonate (696 mg, 2.137 mmol). The solution was degassed by sonication under $N_2$ for 5 min. $Pd(PPh_3)_4$ (123 mg, 0.107 mmol) was then added and the mixture was heated at 95° C. for 2.5 h. The reaction mixture was cooled to room temperature and was diluted with $CH_2Cl_2$ and was transferred to a reparatory funnel containing saturated aqueous $NaHCO_3$ solution (20 mL). The aqueous layer was extracted with $CH_2Cl_2$ (3×25 mL). The combined organic layers were washed with brine (20 mL), dried over $MgSO_4$, filtered and concentrated. The residue was purified by column chromatography on silica gel (2%→5% methanol in $CH_2Cl_2$) to afford 2-isopentyl-6-(pyridin-4-yl)quinoline-3-carbonitrile (246 mg, 76% yield) as a colorless solid: $^1$H NMR (400 MHz, $CDCl_3$) δ 8.74-8.81 (m, 2H), 8.58 (s, 1H), 8.20-8.25 (m, J=8.5 Hz, 1H), 8.09-8.15 (m, 2H), 7.65 (dd, J=4.5, 1.8 Hz, 2H), 3.20-3.28 (m, 2H), 1.75-1.85 (m, 3H), 1.05 (d, J=6.3 Hz, 6H); LCMS (ESI) m/e 302.1 [(M+H)+, calcd for $C_{20}H_{20}N_3$ 302.2].

Example 19

3-methyl-1-(6-(pyridin-4-yl)quinolin-2-yl)butan-1-one

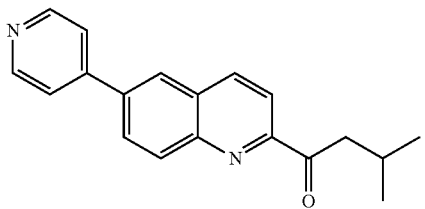 [SMILES: CC(C)CC(=O)c1ccc2cc(-c3ccncc3)ccc2n1]

Part A.
6-bromo-N-methoxy-N-methylquinoline-2-carboxamide

A solution of 6-bromoquinoline-2-carboxylic acid (308 mg, 1.222 mmol), N,O-dimethylhydroxylamine hydrochloride (143 mg, 1.466 mmol), 2-(1H-benzo[d][1,2,3]triazol-1-yl)-1,1,3,3-tetramethyluronium hexafluorophosphate(V) (602 mg, 1.588 mmol) and DIEA (512 μL, 2.93 mmol) in DMF (Volume: 2.44 mL) was stirred at room temperature for 3 h. The reaction mixture was quenched with saturated aqueous sodium bicarbonate and extracted with ethyl acetate (3×10 mL). The combined organics and washed with brine (1×10 mL), dried (MgSO4), filtered and concentrated under reduced pressure. The residue was purified via silica gel chromatography (15%-20% EtOAc in hexanes) to afford 6-bromo-N-methoxy-N-methylquinoline-2-carboxamide (347 mg, 1.15 mmol, 94% yield) as a pale yellow oil: $^1$H NMR (400 MHz, CHLOROFORM-d) δ 8.18 (d, J=8.5 Hz, 1H), 8.05 (d, J=2.3 Hz, 1H), 8.02 (d, J=9.0 Hz, 1H), 7.84 (dd, J=9.0, 2.3 Hz, 1H), 7.72 (br. s., 1H), 3.79 (br. s., 3H), 3.47 (br. s., 3H); LCMS (ESI) m/e 295.0, 297.0 Br pattern [(M+H)+, calcd for $C_{12}H_{12}BrN_2O_2$ 295.0].

Part B.
1-(6-bromoquinolin-2-yl)-3-methylbutan-1-one

To a solution of 6-bromo-N-methoxy-N-methylquinoline-2-carboxamide (163 mg, 0.552 mmol) in THF (Volume: 3.81 mL) cooled to 0° C. was added isobutylmagnesium chloride (2M in THF) (318 μL, 0.635 mmol) dropwise. The solution was stirred at 0° C. for 2 h. The reaction mixture was quenched with aqueous ammonium chloride and extracted with EtOAc (3×10 mL). The combined organics and washed with brine (1×10 mL), dried ($MgSO_4$), filtered and concentrated under reduced pressure. The residue was purified via silica gel chromatography (15%-25% EtOAc in hexanes) to afford 1-(6-bromoquinolin-2-yl)-3-methylbutan-1-one (20 mg, 0.065 mmol, 12% yield) as a colorless solid: LCMS (ESI) m/e 292.1, 294.1 Br pattern [(M+H)+, calcd for $C_{14}H_{15}BrNO$ 292.0].

Part C. 3-methyl-1-(6-(pyridin-4-yl)quinolin-2-yl)butan-1-one

To a vial was added 4-(4,4,5,5-tetramethyl-1,3,2-dioxaborolan-2-yl)pyridine (126 mg, 0.616 mmol), potassium carbonate (213 mg, 1.540 mmol) and tetrakis(triphenylphosphine)palladium(0) (29.7 mg, 0.026 mmol). The vial was sealed and purged with $N_2$ for 5 min. A solution of 1-(6-bromoquinolin-2-yl)-3-methylbutan-1-one (150 mg, 0.513 mmol) in dioxane (2580 μL) and water (430 μL) was added and the vial degassed and purged with N2 for 5 min. The reaction mixture was then heated to 100° C. overnight. The reaction mixture was cooled to room temperature and concentrated under reduced pressure. The residue was purified via silica gel chromatography (10%-60% EtOAc in hexanes) to afford 3-methyl-1-(6-(pyridin-4-yl)quinolin-2-yl)butan-1-one (100 mg, 0.327 mmol, 64% yield) as a pale yellow solid: $^1$H NMR (400 MHz, MeOD) δ ppm 8.92 (d, J=6.8 Hz, 2H), 8.63 (d, J=1.8 Hz, 1H), 8.60 (d, J=8.5 Hz, 1H), 8.47 (d, J=6.8 Hz, 2H), 8.39 (d, J=9.0 Hz, 1H), 8.34 (dd, J=8.8, 2.0 Hz, 1H), 8.18 (d, J=8.5 Hz, 1H), 3.27 (d, J=6.8 Hz, 2H), 2.26-2.46 (sept, J=6.8 Hz, 1H), 1.05 (d, J=6.8 Hz, 6H); LCMS (ESI) m/e 291.1 [(M+H)+, calcd for $C_{19}H_{19}N_2O$ 291.2].

Example 20 and Example 21

(−)-3-methyl-1-(6-(pyridin-4-yl)quinolin-2-yl)butan-1-amine (Example 20)

(+)-3-methyl-1-(6-(pyridin-4-yl)quinolin-2-yl)butan-1-amine (Example 21)

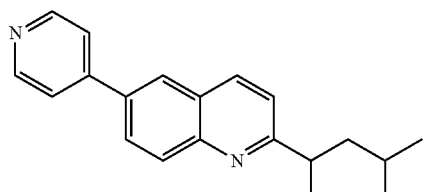

(−)

-continued

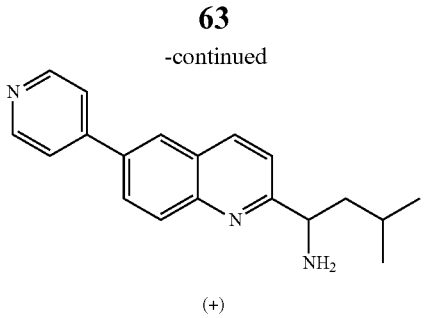

(+)

Part A.
1-(6-bromoquinolin-2-yl)-3-methylbutan-1-ol

A solution of 1-(6-bromoquinolin-2-yl)-3-methylbutan-1-one (120 mg, 0.411 mmol) and sodium borohydride (10.88 mg, 0.288 mmol) in methanol (1.11 mL) was stirred at room temperature for 12 h. The reaction mixture was concentrated under reduced pressure and the residue was purified by reverse phase HPLC (20%-100% MeOH/H$_2$O/0.1% TFA). The concentrated fractions were free based by quenching with saturated aqueous sodium bicarbonate and extracting with ethyl acetate (3×5 mL). The combined organics were washed with saturated aqueous sodium bicarbonate (2×5 mL) and brine (1×5 mL), dried (MgSO$_4$), filtered, and concentrated under reduced pressure. Obtained 1-(6-bromo-quinolin-2-yl)-3-methylbutan-1-ol (65 mg, 0.217 mmol, 53% yield) as a yellow oil. LCMS (ESI) m/e 294.1, 296.1 Br pattern [(M+H)$^+$, calcd for C$_{14}$H$_{17}$BrNO 294.1].

Part B. 2-(1-(6-bromoquinolin-2-yl)-3-methylbutyl)isoindoline-1,3-dione

To a solution of 1-(6-bromoquinolin-2-yl)-3-methylbutan-1-ol (130 mg, 0.442 mmol) in dry tetrahydrofuran (3.84 mL) at 0° C. was added phthalimide (195 mg, 1.326 mmol), triphenylphosphine (174 mg, 0.663 mmol) and DIAD (129 μl, 0.663 mmol). The reaction was stirred at room temperature for 1 h. The mixture was quenched with saturated aqueous sodium bicarbonate and extracted with ethyl acetate (3×5 mL). The combined organics were washed with brine (1×5 mL), dried (MgSO$_4$), filtered, and concentrated under reduced pressure. The residue was purified via silica gel chromatography (10%-100% EtOAc in hexanes) to obtain 2-(1-(6-bromoquinolin-2-yl)-3-methylbutyl)isoindoline-1,3-dione (185 mg, 0.415 mmol, 94% yield) as a pale yellow amorphous solid. LCMS (ESI) m/e 423.0, 425.0 Br pattern [(M+H)$^+$, calcd for C$_{22}$H$_{20}$BrN$_2$O$_2$ 423.1].

Part C. 2-(3-methyl-1-(6-(pyridin-4-yl)quinolin-2-yl)butyl)isoindoline-1,3-dione To a microwave vial was added 2-(1-(6-bromoquinolin-2-yl)-3-methylbutyl)isoindoline-1,3-dione (176 mg, 0.415 mmol), 4-(4,4,5,5-tetramethyl-1,3,2-dioxaborolan-2-yl)pyridine (102 mg, 0.498 mmol), potassium carbonate (172 mg, 1.245 mmol) and tetrakis(triphenylphosphine)palladium(0) (23.98 mg, 0.021 mmol). The vial was sealed and purged with N2 for 5 min. Dioxane (2.58 mL) and water (0.43 mL) was added and the mixture was purged with N2 for 5 min. The mixture was then heated to 100° C. in a microwave for 16 h. The residue was purified via silica gel chromatography (10%-60% EtOAc in hexanes) to afford 2-(3-methyl-1-(6-(pyridin-4-yl)quinolin-2-yl)butyl)isoindo-line-1,3-dione (111 mg, 0.250 mmol, 60% yield) as a yellow oil. LCMS (ESI) m/e 422.2 [(M+H)$^+$, calcd for C$_{27}$H$_{24}$N$_3$O$_2$ 422.2].

Part D. 2-(3-methyl-1-(6-(pyridin-4-yl)quinolin-2-yl)butyl)isoindoline-1,3-dione To a solution of 2-(3-methyl-1-(6-(pyridin-4-yl)quinolin-2-yl)butyl)isoindoline-1,3-dione (0.111 g, 0.263 mmol) in EtOH (2 mL) at room temperature was added hydrazine (0.012 mL, 0.395 mmol). The reaction mixture was stirred at room temperature for 14 h. The reaction mixture was concentrated under reduced pressure and the residue purified by reverse phase preparative HPLC (water/Methanol/0.1% TFA). Obtained 3-methyl-1-(6-(pyridin-4-yl)quinolin-2-yl)butan-1-amine (0.0549 g, 0.185 mmol, 70% yield) as a racemic mixture. The mixture was separated by chiral SCF (column: ChiralCel AD-H (4.6×250 mm, 5 μm); mobile phase: 15% MeOH (w/0.1% DEA)/85% CO$_2$; 150 bar, 35° C., 25 mL/min, λ=254 nm). Obtained two peaks; the absolute stereochemistry of each isomer was not determined:

Example 20 (Peak 1)

[α]$^{22}_D$ −1.90 (c 17.85, MeOH); $^1$H NMR (400 MHz, METHANOL-d$_4$) δ 8.99-8.93 (m, 2H), 8.70 (d, J=1.3 Hz, 1H), 8.63-8.54 (m, 3H), 8.39-8.33 (m, 2H), 7.70 (d, J=8.5 Hz, 1H), 4.77 (t, J=7.3 Hz, 1H), 2.05-1.85 (m, 2H), 1.70 (dquin, J=13.5, 6.7 Hz, 1H), 1.06 (d, J=6.5 Hz, 3H), 1.03 (d, J=6.5 Hz, 3H); LCMS (ESI) m/e 292.2 [(M+H)$^+$, calcd for C$_{19}$H$_{22}$N$_3$ 292.2].

Example 21 (Peak 2)

[α]$^{22}_D$ +4.05 (c 4.65, MeOH); $^1$H NMR (400 MHz, METHANOL-d$_4$) δ 8.99-8.93 (m, 2H), 8.70 (d, J=1.3 Hz, 1H), 8.63-8.54 (m, 3H), 8.39-8.33 (m, 2H), 7.70 (d, J=8.5 Hz, 1H), 4.77 (t, J=7.3 Hz, 1H), 2.05-1.85 (m, 2H), 1.70 (dquin, J=13.5, 6.7 Hz, 1H), 1.06 (d, J=6.5 Hz, 3H), 1.03 (d, J=6.5 Hz, 3H); LCMS (ESI) m/e 292.2 [(M+H)$^+$, calcd for C$_{19}$H$_{22}$N$_3$ 292.2].

Example 22 and Example 23

(+)-1-(6-(3-methoxypyridin-4-yl)quinolin-2-yl)-3-methylbutan-1-amine (Example 22)

(−)-1-(6-(3-methoxypyridin-4-yl)quinolin-2-yl)-3-methylbutan-1-amine (Example 23)

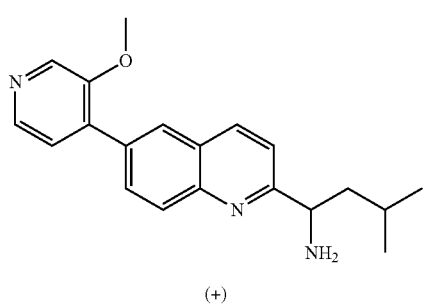

(+)

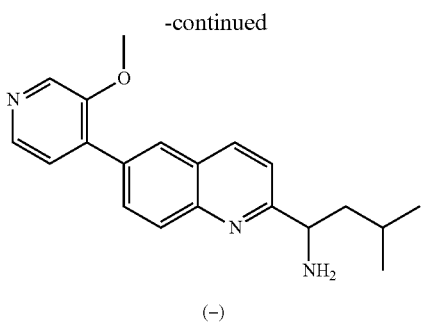

(−)

Part A. 2-(1-(6-(3-methoxypyridin-4-yl)quinolin-2-yl)-3-methylbutyl)isoindoline-1,3-dione To a microwave vial was added 3-methoxypyridin-4-ylboronic acid (82 mg, 0.539 mmol), 2-(1-(6-bromoquinolin-2-yl)-3-methylbutyl)isoindoline-1,3-dione (190 mg, 0.449 mmol) (prepared as in Example 20 and 21, Part B), tetrakis(triphenylphosphine)palladium(0) (25.9 mg, 0.022 mmol) and potassium carbonate (186 mg, 1.347 mmol). The vial was sealed and purged with N2 for 5 min. Dioxane (3.85 mL) and water (641 μL) were added and the vial degassed and purged with N2 for 5 min. The mixture was then heated to 100° C. overnight. The residue was purified via silica gel chromatography (10%-100% EtOAc in hexanes). Obtained 2-(1-(6-(3-methoxypyridin-4-yl)quinolin-2-yl)-3-methylbutyl)isoindoline-1,3-dione (85 mg, 0.179 mmol, 40% yield) as a pale yellow amorphous solid. LCMS (ESI) m/e 452.2 [(M+H)$^+$, calcd for $C_{28}H_{26}N_3O_3$ 452.2].

Part B. 2-(1-(6-(3-methoxypyridin-4-yl)quinolin-2-yl)-3-methylbutyl)isoindoline-1,3-dione A solution of 2-(1-(6-(3-methoxypyridin-4-yl)quinolin-2-yl)-3-methylbutyl)isoindoline-1,3-dione (85 mg, 0.188 mmol) and hydrazine (68.9 μL, 2.194 mmol) in ethanol (1.88 mL) was heated to 40° C. for 2 h. The residue via silica gel chromatography (10%-60% EtOAc in hexanes) to afford 1-(6-(3-methoxypyridin-4-yl)quinolin-2-yl)-3-methylbutan-1-amine (14 mg, 0.043 mmol, 23% yield) as a racemic mixture of a brown oil. The mixture was separated by chiral SCF (column: ChiralCel AD-H (30×250 mm, 5 μm); mobile phase: 15% EtOH (w/0.1% DEA)/85% CO$_2$; 150 bar, 35° C., 70 mL/min, λ=254 nm). Obtained two peaks; the absolute stereochemistry of each isomer was not determined:

Example 22 (Peak 1)

[α]$^{22}_D$ +1.90 (c 2.95, MeOH); $^1$H NMR (400 MHz, CHLOROFORM-d) δ ppm 8.43 (s, 1H), 8.37 (d, J=4.8 Hz, 1H), 8.16 (d, J=8.5 Hz, 1H), 8.12 (d, J=8.8 Hz, 1H), 7.99 (d, J=2.0 Hz, 1H), 7.90 (dd, J=8.7, 1.9 Hz, 1H), 7.47 (d, J=8.5 Hz, 1H), 7.34 (d, J=4.8 Hz, 1H), 4.39 (t, J=7.0 Hz, 1H), 4.21 (br. s., 2H), 3.95 (s, 3H), 1.62-1.85 (m, 3H), 0.99 (d, J=6.0 Hz, 3H), 0.97 (d, J=6.3 Hz, 3H); LCMS (ESI) m/e 322.2 [(M+H)$^+$, calcd for $C_{20}H_{24}N_3O$ 322.2].

Example 23 (Peak 2)

[α]$^{22}_D$ −0.94 (c 2.55, MeOH); $^1$H NMR (400 MHz, CHLOROFORM-d) δ ppm 8.43 (s, 1H), 8.37 (d, J=4.8 Hz, 1H), 8.16 (d, J=8.5 Hz, 1H), 8.12 (d, J=8.8 Hz, 1H), 7.99 (d, J=2.0 Hz, 1H), 7.90 (dd, J=8.7, 1.9 Hz, 1H), 7.47 (d, J=8.5 Hz, 1H), 7.34 (d, J=4.8 Hz, 1H), 4.39 (t, J=7.0 Hz, 1H), 4.21 (br. s., 2H), 3.95 (s, 3H), 1.62-1.85 (m, 3H), 0.99 (d, J=6.0 Hz, 3H), 0.97 (d, J=6.3 Hz, 3H); LCMS (ESI) m/e 322.2 [(M+H)$^+$, calcd for $C_{20}H_{24}N_{30}$ 322.2].

Example 24

1-(6-(3-methoxypyridin-4-yl)quinolin-2-yl)-3-methylbutan-1-amine

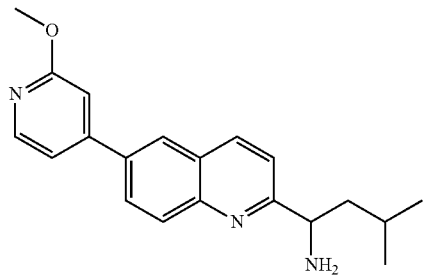 [SMILES: COc1cc(-c2ccc3nc(C(N)CC(C)C)ccc3c2)ccn1]

The title compound was prepared as described in Example 20 and 21 using 2-methoxypyridin-4-ylboronic acid (21.68 mg, 0.142 mmol) in part C. Obtained 1-(6-(2-methoxypyridin-4-yl)quinolin-2-yl)-3-methylbutan-1-amine (10 mg, 0.030 mmol, 38% yield for final step) as a brown amorphous solid. $^1$H NMR (400 MHz, CHLOROFORM-d) δ ppm 8.28 (1H, d, J=6.0 Hz), 8.19 (1H, d, J=8.5 Hz), 8.15 (1H, d, J=8.8 Hz), 8.05 (1H, d, J=2.0 Hz), 7.95 (1H, dd, J=8.7, 2.1 Hz), 7.48 (1H, d, J=8.5 Hz), 7.24 (1H, dd, J=5.4, 1.6 Hz), 7.09 (1H, s), 4.27 (1H, br. s.), 4.02 (3H, s), 2.09-2.30 (2H, m), 1.62-1.81 (3H, m), 0.99 (6H, t, J=5.8 Hz); LCMS (ESI) m/e 322.1 [(M+H)$^+$, calcd for $C_{20}H_{24}N_{30}$ 322.2].

Example 25

1-(6-(1H-pyrrolo[2,3-b]pyridin-4-yl)quinolin-2-yl)-3-methylbutan-1-amine

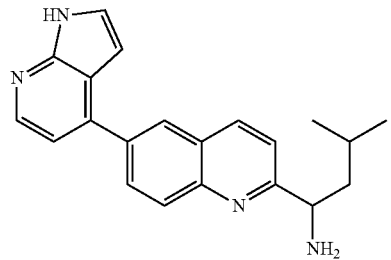 [SMILES: CC(C)CC(N)c1ccc2cc(-c3ccnc4[nH]ccc34)ccc2n1]

Part A. 6-bromoquinoline-2-carbaldehyde

To a solution of 6-bromo-2-methylquinoline (10 g, 45.0 mmol) in 1,4-dioxane (100 mL) at room temperature under nitrogen was added selenium dioxide (6.00 g, 54.0 mmol). The reaction mixture was heated to 75° C. for 5 h. The reaction mixture was filtered through diatomaceous earth (Celite®) and washed with ethyl acetate. The filtrate was concentrated and the residue was triturated with hexanes to crash out the product. The solid was collected via vacuum filtration the dried under high vacuum overnight to obtain 6-bromoquinoline-2-carbaldehyde (8.86 g, 37.5 mmol, 83% yield) as an off-white solid. $^1$H NMR (400 MHz, DMSO-$d_6$) δ 10.11 (d, J=1.0 Hz, 1H), 8.56 (d, J=8.5 Hz, 1H), 8.43 (d, J=2.3 Hz, 1H), 8.14 (d, J=9.0 Hz, 1H), 8.05-8.02 (m, 1H), 8.02-8.00 (m, 1H); LCMS (ESI) m/e 235.9, 237.9 Br pattern [(M+H)$^+$, calcd for $C_{10}H_7BrNO$ 236.0].

Part B. N-((6-bromoquinolin-2-yl)methylene)-2-methylpropane-2-sulfinamide

To a solution of 6-bromoquinoline-2-carbaldehyde (8.86 g, 37.5 mmol) in THF (175 ml) at room temperature under nitrogen was added ethyl orthotitanate (7.73 ml, 37.5 mmol). The reaction mixture was stirred at room temperature for 10 min then 2-methylpropane-2-sulfinamide (4.55 g, 37.5 mmol) was added. The reaction mixture was heated to reflux for 3 h. The reaction mixture was cooled to room temperature and quenched with brine. The reaction mixture was filtered through diatomaceous earth (Celite®) and the filtrate extracted with ethyl acetate (4×200 mL). The combined organic layers were washed with water (1×200 mL), brine (1×200 mL), dried (MgSO4), filtered and concentrated under reduced pressure to obtain N-((6-bromoquinolin-2-yl)methylene)-2-methylpropane-2-sulfinamide (11.98 g, 35.3 mmol, 94% yield) as yellow solid. The product was used as such without further purification. $^1$H NMR (400 MHz, CHLOROFORM-d) δ 8.83 (s, 1H), 8.15 (s, 2H), 8.08-7.99 (m, 2H), 7.82 (dd, J=9.0, 2.3 Hz, 1H), 1.30 (s, 9H); LCMS (ESI) m/e 339.0, 341.0 Br pattern [(M+H)$^+$, calcd for $C_{14}H_{16}BrN_2OS$ 339.0].

Part C. N-(1-(6-bromoquinolin-2-yl)-3-methylbutyl)-2-methylpropane-2-sulfinamide To a stirred solution of N-((6-bromoquinolin-2-yl)methylene)-2-methylpropane-2-sulfinamide (11.98 g, 35.3 mmol) in THF (240 ml) at −45° C. under nitrogen was added isobutylmagnesium chloride (17.66 ml, 35.3 mmol) dropwise. The reaction mixture was stirred at −45° C. for 3 h. The reaction mixture was quenched by addition of saturated ammonium chloride at −45° C., the extracted with ethyl acetate (4×200 mL). The combined organic layers were washed with water (1×200 mL), brine (1×200 mL), dried (MgSO4), filtered and concentrated under reduced pressure to obtain N-(1-(6-bromoquinolin-2-yl)-3-methylbutyl)-2-methylpropane-2-sulfinamide (8.5 g, 21.39 mmol, 61% yield) and thick oil. $^1$H NMR (400 MHz, CHLOROFORM-d) δ 7.98 (d, J=8.5 Hz, 1H), 7.92-7.85 (m, 2H), 7.71 (dd, J=8.9, 2.1 Hz, 1H), 7.35 (d, J=8.5 Hz, 1H), 5.32 (d, J=5.0 Hz, 1H), 4.61 (ddd, J=9.2, 7.3, 4.9 Hz, 1H), 1.90-1.67 (m, 2H), 1.65-1.54 (m, 1H), 1.30 (s, 9H), 0.99 (d, J=6.3 Hz, 3H), 0.92 (d, J=6.8 Hz, 3H); LCMS (ESI) m/e 397.0, 399.0 Br pattern [(M+H)$^+$, calcd for $C_{18}H_{26}BrN_2OS$ 397.1].

Part D. 2-methyl-N-(3-methyl-1-(6-(trimethylstannyl)quinolin-2-yl)butyl)propane-2-sulfinamide To a stirred solution of N-(1-(6-bromoquinolin-2-yl)-3-methylbutyl)-2-methylpropane-2-sulfinamide (8.5 g, 21.39 mmol) in Dioxane (250 ml) at room temperature under nitrogen was added hexamethylditin (6.65 ml, 32.1 mmol), bis(triphenylphosphine)palladium(II) chloride (1.501 g, 2.139 mmol). The reaction mixture was degassed for 5 minutes and then heated to 100° C. for 14 h. The reaction mixture was diluted with ethyl acetate (500 mL) and water (300 mL). The layers were separated and the aqueous layer was extracted with ethyl acetate (3×400 mL). The combined organic layers were washed with water (1×300 mL), brine (1×300 mL), dried (MgSO4), filtered and concentrated under reduced pressure. The residue was purified by silica gel chromatography (EtOAc in hexanes) to obtain 2-methyl-N-(3-methyl-1-(6-(trimethylstannyl)quinolin-2-yl)butyl) propane-2-sulfinamide (4.3 g, 8.93 mmol, 42% yield) as oil. $^1$H NMR (400 MHz, CHLOROFORM-d) δ 8.08 (d, J=8.5 Hz, 1H), 7.99 (d, J=8.3 Hz, 1H), 7.90 (s, 1H), 7.79 (dd, J=8.2, 1.1 Hz, 1H), 7.34 (d, J=8.5 Hz, 1H), 5.47 (d, J=6.8 Hz, 1H), 4.63 (ddd, J=8.9, 6.9, 5.0 Hz, 1H), 1.90-1.71 (m, 2H), 1.68-1.57 (m, 1H), 1.30 (s, 9H), 1.00 (d, J=6.5 Hz, 3H), 0.92 (d, J=6.5 Hz, 3H), 0.36 (s, 9H); LCMS (ESI) m/e 483.0 [(M+H)$^+$, calcd for $C_{21}H_{35}N_2OSSn$ 483.2].

Part E. N-(1-(6-(1H-pyrrolo[2,3-b]pyridin-4-yl)quinolin-2-yl)-3-methylbutyl)-2-methylpropane-2-sulfinamide To the solution of 2-methyl-N-(3-methyl-1-(6-(trimethylstannyl)quinolin-2-yl)butyl)propane-2-sulfinamide (0.05 g, 0.104 mmol) in DMF (2 mL) in a pressure tube were added 4-bromo-1H-pyrrolo[2,3-b]pyridine (0.020 g, 0.104 mmol), bis-triphenylphosphine dichloropalladium (7.29 mg, 10.39 μmol), potassium carbonate (0.043 g, 0.312 mmol) and tetrabutylammonium bromide (0.067 g, 0.208 mmol). The reaction mixture was purged with nitrogen gas for 5 min and capped. The reaction mixture was heated at 95° C. for 16 h. The reaction mixture was cooled to ambient temperature and quenched with water (15 mL). The solution was extracted with ethyl acetate (2×10 mL). The combined organic layers were washed with water (1×10 mL), brine (1×10 mL), dried (sodium sulfate), filtered and concentrated under reduced pressure. The residue was purified by reverse phase preparative HPLC (water/methanol/0.1% TFA) to obtain N-(1-(6-(1H-pyrrolo[2,3-b]pyridin-4-yl)quinolin-2-yl)-3-methylbutyl)-2-methylpropane-2-sulfinamide (0.031 g, 0.071 mmol, 69% yield). LCMS (ESI) m/e 435.1 [(M+H)$^+$, calcd for $C_{25}H_{31}N_4OS$ 435.2].

Part F. 1-(6-(1H-pyrrolo[2,3-b]pyridin-4-yl)quinolin-2-yl)-3-methylbutan-1-amine To a solution of N-(1-(6-(1H-pyrrolo[2,3-b]pyridin-4-yl)quinolin-2-yl)-3-methylbutyl)-2-methylpropane-2-sulfinamide (0.031 g, 0.071 mmol) in methanol (10 mL) at room temperature under nitrogen was added HCl (1.25M in methanol) (0.571 mL, 0.713 mmol). The reaction mixture was stirred at room temperature for 14 h. The reaction mixture was concentrated and purified by reverse phase preparative HPLC (water/methanol/0.1% TFA) to obtain 1-(6-(1H-pyrrolo[2,3-b]pyridin-4-yl)quinolin-2-yl)-3-methylbutan-1-amine, 2 TFA (0.0162 g, 0.028 mmol, 39% yield) as a colorless film. $^1$H NMR (400 MHz, METHANOL-$d_4$) δ 8.59 (d, J=8.5 Hz, 1H), 8.55-8.46 (m, 2H), 8.38-8.32 (m, 1H), 8.32-8.25 (m, 1H), 7.79-7.71 (m, 2H), 7.68 (d, J=8.5 Hz, 1H), 7.04 (d, J=3.8 Hz, 1H), 4.76 (t, J=7.3 Hz, 1H), 2.06-1.85 (m, 2H), 1.71 (dquin, J=13.4, 6.6 Hz, 1H), 1.05 (dd, J=11.0, 6.5 Hz, 6H); LCMS (ESI) m/e 331.0 [(M+H)$^+$, calcd for $C_{21}H_{23}N_4$ 331.2].

Example 26

1-([4,6'-biquinolin]-2'-yl)-3-methylbutan-1-amine

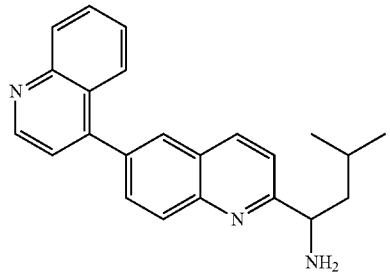 [SMILES: CC(C)CC(N)c1ccc2cc(-c3ccnc4ccccc34)ccc2n1]

The title compound was prepared as described in Example 25 using 4-bromoquinoline (0.022 g, 0.104 mmol) in part E to afford 1-([4,6'-biquinolin]-2'-yl)-3-methylbutan-1-amine, 2 TFA (0.0182 g, 0.031 mmol, 30% yield for two steps) as a colorless film. $^1$H NMR (400 MHz, METHANOL-$d_4$) δ 9.27 (d, J=5.5 Hz, 1H), 8.59 (d, J=8.3 Hz, 1H), 8.44-8.34 (m, 3H), 8.27 (d, J=8.5 Hz, 1H), 8.21 (ddd, J=8.6, 7.1, 1.1 Hz, 1H), 8.15-8.06 (m, 2H), 7.96 (ddd, J=8.4, 7.2, 1.0 Hz, 1H), 7.73 (d, J=8.5 Hz, 1H), 4.79 (t, J=7.3 Hz, 1H), 2.06-1.87 (m, 2H), 1.72 (dquin, J=13.5, 6.7 Hz, 1H), 1.10-1.00 (m, 6H); LCMS (ESI) m/e 342.0 [(M+H)$^+$, calcd for $C_{23}H_{24}N_3$ 342.2].

Example 27

1-(6-(isoquinolin-6-yl)quinolin-2-yl)-3-methylbutan-1-amine

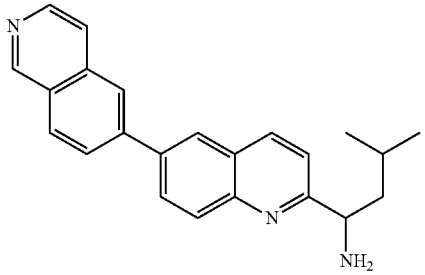 [SMILES: CC(C)CC(N)c1ccc2cc(-c3ccc4cnccc4c3)ccc2n1]

The title compound was prepared as described in Example 25 using 6-bromoisoquinoline (0.022 g, 0.104 mmol) in part E to afford 1-(6-(isoquinolin-6-yl)quinolin-2-yl)-3-methylbutan-1-amine, 2 TFA (0.0256 g, 0.044 mmol, 42% yield for two steps) as a pale yellow film. $^1$H NMR (400 MHz, METHANOL-$d_4$) δ 9.81 (s, 1H), 8.75 (d, J=0.5 Hz, 1H), 8.68-8.61 (m, 2H), 8.61-8.53 (m, 4H), 8.41-8.36 (m, 1H), 8.35-8.30 (m, 1H), 7.67 (d, J=8.5 Hz, 1H), 4.76 (t, J=7.3 Hz, 1H), 2.04-1.86 (m, 2H), 1.71 (dquin, J=13.5, 6.7 Hz, 1H), 1.06 (dd, J=11.8, 6.5 Hz, 6H); LCMS (ESI) m/e 342.0 [(M+H)$^+$, calcd for $C_{23}H_{24}N_3$ 342.2].

Example 28

4-(2-(1-amino-3-methylbutyl)quinolin-6-yl)-N,N-dimethylpyrimidin-2-amine

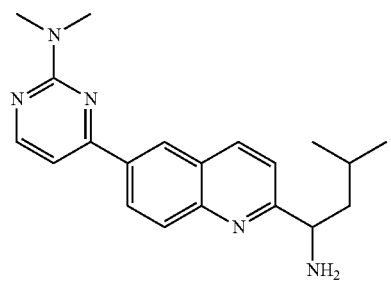 [SMILES: CC(C)CC(N)c1ccc2cc(-c3ccnc(N(C)C)n3)ccc2n1]

The title compound was prepared as described in Example 25 using 4-bromo-N,N-dimethylpyrimidin-2-amine (0.021 g, 0.104 mmol) in part E to afford 4-(2-(1-amino-3-methylbutyl)quinolin-6-yl)-N,N-dimethylpyrimidin-2-amine, 2 TFA (0.016 g, 0.028 mmol, 28% yield for two steps) as a yellow oil. $^1$H NMR (400 MHz, METHANOL-$d_4$) δ 8.91 (d, J=2.0 Hz, 1H), 8.65 (dd, J=9.0, 2.0 Hz, 1H), 8.59 (d, J=8.3 Hz, 1H), 8.42 (d, J=6.0 Hz, 1H), 8.27 (d, J=8.8 Hz, 1H), 7.67 (d, J=8.5 Hz, 1H), 7.61 (d, J=6.3 Hz, 1H), 4.75 (t, J=7.3 Hz, 1H), 3.42 (s, 6H), 2.03-1.84 (m, 2H), 1.70 (dquin, J=13.5, 6.7 Hz, 1H), 1.05 (dd, J=10.2, 6.7 Hz, 6H); LCMS (ESI) m/e 336.0 [(M+H)$^+$, calcd for $C_{20}H_{26}N_5$ 336.2].

Example 29

4-(2-(1-amino-3-methylbutyl)quinolin-6-yl)pyridin-2-amine

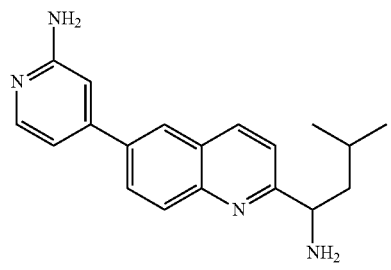 [SMILES: CC(C)CC(N)c1ccc2cc(-c3ccnc(N)c3)ccc2n1]

Part A. N-(1-(6-(2-aminopyridin-4-yl)quinolin-2-yl)-3-methylbutyl)-2-methylpropane-2-sulfinamide To a solution of 2-methyl-N-(3-methyl-1-(6-(trimethylstannyl)quinolin-2-yl)butyl)propane-2-sulfinamide (0.05 g, 0.104 mmol) in DMF (2 mL) in a pressure tube were added 4-bromopyridin-2-amine (0.018 g, 0.104 mmol), bis-triphenylphosphine dichloropalladium (7.29 mg, 10.39 μmol), potassium carbonate (0.043 g, 0.312 mmol) and tetrabutylammonium bromide (0.067 g, 0.208 mmol). The reaction mixture was purged with nitrogen gas for 5 min and screwcapped. The reaction mixture was heated at 95° C. for 16 h. The reaction mixture was cooled to ambient temperature and quenched with water (15 mL). The mixture was extracted with ethyl acetate (2×10 mL). The combined organic layers were washed with water (1×10 mL), brine (1×10 mL), dried (sodium sulfate), filtered and concentrated under reduced pressure. The residue was purified by reverse phase preparative HPLC (water/methanol/0.1% TFA) to afford N-(1-(6-(2-aminopyridin-4-yl)quinolin-2-yl)-3-methylbutyl)-2-methylpropane-2-sulfinamide (0.031 g, 0.076 mmol, 73% yield). LCMS (ESI) m/e 411.1 [(M+H)+, calcd for $C_{23}H_{31}N_4OS$ 411.2].

Part B. 4-(2-(1-amino-3-methylbutyl)quinolin-6-yl)pyridin-2-amine, 2 TFA (0.0224 g, 0.041 mmol, 54% yield)

To a solution of N-(1-(6-(2-aminopyridin-4-yl)quinolin-2-yl)-3-methylbutyl)-2-methylpropane-2-sulfinamide (0.031 g, 0.076 mmol) in methanol (10 mL) at room temperature under nitrogen was added HCl (methanol) (0.604 mL, 0.755 mmol) (1.25M). The reaction mixture was stirred at room temperature overnight. The reaction mixture was concentrated and the residue purified by reverse phase preparative HPLC (water/methanol/0.1% TFA) to obtain 4-(2-(1-amino-3-methylbutyl)quinolin-6-yl)pyridin-2-amine, 2 TFA (0.0224 g, 0.041 mmol, 54% yield) as a pale yellow solid. $^1$H NMR (400 MHz, METHANOL-d$_4$) δ 8.55 (d, J=8.3 Hz, 1H), 8.46 (d, J=2.0 Hz, 1H), 8.29 (d, J=9.0 Hz, 1H), 8.18 (dd, J=8.9, 2.1 Hz, 1H), 7.97 (dd, J=6.8, 0.8 Hz, 1H), 7.67 (d, J=8.5 Hz, 1H), 7.42-7.35 (m, 2H), 4.75 (t, J=7.3 Hz, 1H), 2.02-1.84 (m, 2H), 1.69 (dquin, J=13.5, 6.7 Hz, 1H), 1.04 (dd, J=10.5, 6.5 Hz, 6H); LCMS (ESI) m/e 307.0 [(M+H)+, calcd for $C_{19}H_{23}N_4$ 307.2].

Example 30

N-(4-(2-(3-methylbutanoyl)quinolin-6-yl)pyridin-2-yl)acetamide

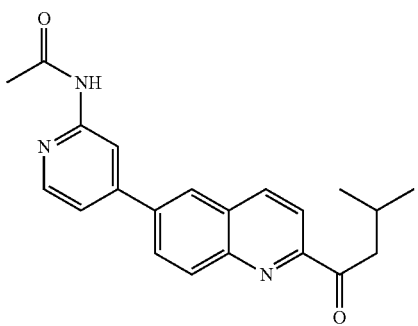 [SMILES: CC(=O)Nc1cc(-c2ccc3nc(C(=O)CC(C)C)ccc3c2)ccn1]

To a solution of N-(1-(6-(2-aminopyridin-4-yl)quinolin-2-yl)-3-methylbutyl)-2-methylpropane-2-sulfinamide (0.059 g, 0.144 mmol) (prepared as in Example 29, Part A) in CH$_2$Cl$_2$ (10 mL) at room temperature under nitrogen was added acetyl chloride (10.22 µL, 0.144 mmol) and DIEA (0.063 mL, 0.359 mmol). The reaction mixture was stirred at room temperature overnight. The reaction mixture was concentrated and purified by reverse phase preparative HPLC (water/methanol/0.1% TFA) to afford N-(4-(2-(3-methylbutanoyl)quinolin-6-yl)pyridin-2-yl)acetamide (0.017 g, 0.048 mmol, 33% yield) as a brown film. $^1$H NMR (400 MHz, METHANOL-d$_4$) δ 8.55 (d, J=8.3 Hz, 1H), 8.47-8.40 (m, 2H), 8.33 (d, J=8.8 Hz, 1H), 8.23-8.12 (m, 2H), 8.07 (d, J=1.3 Hz, 1H), 7.86 (dd, J=6.0, 1.8 Hz, 1H), 3.26 (d, J=6.8 Hz, 2H), 2.42-2.26 (m, 4H), 1.05 (d, J=6.8 Hz, 6H); LCMS (ESI) m/e 348.0 [(M+H)+, calcd for $C_{21}H_{22}N_3O_2$ 348.2].

Example 31

2-isopentyl-6-(pyridin-4-yl)quinoline-4(1H)-thione

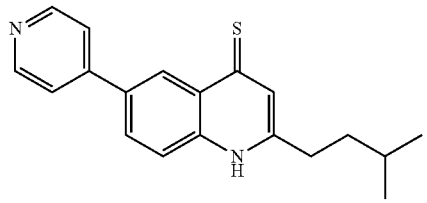 [SMILES: CC(C)CCc1cc(=S)c2cc(-c3ccncc3)ccc2[nH]1]

Part A. Ethyl 6-methyl-3-oxoheptanoate

A solution of sodium hydride (5.4 g, 225 mmol) in dry THF (500 mL) was slowly flushed with nitrogen then cooled in an ice bath. Ethyl-3-oxobutanoate (13 g, 100 mmol) was added dropwise and the colorless solution was stirred at 0° C. for 10 min. n-BuLi, 1.6M in hexanes (65.6 mL, 105 mmol) was added dropwise and the orange solution was stirred at 0° C. for 10 min. To the reaction mixture was added a solution of isobutyl iodide (12.73 mL, 110 mmol) in dry THF (20 mL) and the reaction mixture was stirred at room temperature for 15 min. The color of the dianion faded immediately on addition of the isobutyl iodide. The reaction mixture was quenched with concentrated HCl (20 mL), water (50 mL) and diluted with diethyl ether (150 mL). The organic phase was washed with water until the aqueous extracts showed neutral pH. The organic layer was dried over Na$_2$SO$_4$, filtered and concentrated under reduced pressure. The crude product was purified by column chromatography on silica gel (15-30% ethyl acetate in hexanes) to afford ethyl 6-methyl-3-oxoheptanoate (13.2 g, 0.035 mmol, 35% yield) as a pale yellow oil. $^1$H NMR (400 MHz, DMSO-d$_6$) δ ppm 4.04-4.16 (m, 2H), 3.58 (s, 2H), 2.51-2.55 (m, 2H), 1.35-1.54 (m, 3H), 1.15-1.25 (m, 3H), 0.8-0.98 (m, 6H).

Part B. (E)-ethyl 3-(4-bromophenylamino)-6-methylhept-2-enoate

To a solution of 4-bromoaniline (9.8 g, 57.0 mmol) and ethyl 6-methyl-3-oxoheptanoate (10.61 g, 57.0 mmol) in toluene (60 mL) was added acetic acid (1.631 mL, 28.5 mmol) and 4 Å molecular sieves (2 g). The mixture was heated at 85° C. for 24 h. The mixture was then cooled to room temperature and concentrated under reduced pressure. The crude product was purified by column chromatography on silica gel (10%-50% ethyl acetate in hexanes) to afford (E)-ethyl 3-((4-bromophenyl)amino)-6-methylhept-2-enoate (7 g, 18.93 mmol, 28% yield) as a pale yellow solid. LCMS (ESI) m/e 340.0 [(M+H)+, calcd for $C_{16}H_{23}BrNO_2$, 340.08]; LC/MS retention time (method A): $t_R$=2.73 min.

Part C. 6-bromo-2-isopentylquinolin-4(1H)-one

A mixture of diphenyl ether (100 mL, 629 mmol) and (E)-ethyl 3-((4-bromophenyl)amino)-6-methylhept-2-enoate (5.00 g, 14.69 mmol) in a 100 mL round bottom flask was heated at 250° C. for 1 h. The mixture was cooled to room temperature and transferred to a larger flask containing hexanes (200 mL) preheated to 40° C. The solid obtained was filtered and washed with hexane (200 mL) to afford 6-bromo-2-isopentylquinolin-4(1H)-one (3.48 g, 11.61 mmol, 79% yield) as a brown solid. $^1$H NMR (400 MHz, CD$_3$OD) δ ppm 8.34 (d, J=6.4 Hz, 1H), 7.81 (dd, J=8.8, 6.4 Hz, 1H), 7.54 (d, J=8.8 Hz, 1H), 6.25 (s, 1H), 2.72-2.76 (m, 2H), 1.63-1.71 (m, 3H), 1.01 (d, J=6.4 Hz, 6H).

Part D. 2-isopentyl-6-(pyridin-4-yl)quinolin-4(1H)-one

To a solution of 6-bromo-2-isopentylquinolin-4(1H)-one (3.8 g, 12.92 mmol) in toluene (81.6 mL) and ethanol (21 mL), was added pyridine-4-boronic acid (2.38 g, 19.38 mmol) followed by 1M aqueous Na$_2$CO$_3$ (15.5 mL, 15.5 mmol). Nitrogen gas was bubbled through the stirred suspension for 5 min. Pd(PPh$_3$)$_4$ (1.49 g, 1.29 mmol) was added and nitrogen gas was again bubbled through the stirred suspension for 5 min. The reaction mixture was then heated at 95° C. for 3 h. The reaction mixture was cooled to room temperature and diluted with aqueous sodium bicarbonate solution (50 mL). The aqueous solution was extracted with ethyl acetate (2×50 mL). The combined organic layers were washed with brine (10 mL), dried over Na$_2$SO$_4$, filtered and concentrated under reduced pressure to afford 2-isopentyl-6-(pyridin-4-yl)quinolin-4(1H)-one (2.78 g, 0.17 9.49 mmol, 73% yield) as pale brown solid. LCMS (ESI) m/e 293.2 [(M+H)$^+$, calcd for C$_{19}$H$_{21}$N$_2$O, 293.16]; LC/MS retention time (method A): t$_R$=1.44 min.

Part E. 2-isopentyl-6-(pyridin-4-yl)quinoline-4(1H)-thione

To a solution of 2-isopentyl-6-(pyridin-4-yl)quinolin-4 (1H)-one (51 mg, 0.17 mmol) in pyridine (0.5 mL), was added phosphorous pentasulfide (51 mg, 0.23 mmol) and the resultant mixture refluxed for 1 h. The reaction mixture was cooled to room temperature and water (0.05 mL) was added. The mixture was then stirred at room temperature for 2 h. The solvents were removed under reduced pressure, and saturated ammonium chloride (2 mL) was added. The aqueous layer was extracted with ethyl acetate (3×10 mL). the combined organic layers were washed with brine (10 mL), dried over Na$_2$SO$_4$, filtered and concentrated under reduced pressure. The crude product was purified by preparative HPLC (0.1% TFA in water and acetonitrile) to afford 2-isopentyl-6-(pyridin-4-yl)quinoline-4(1H)-thione, TFA (17 mg, 0.055 mmol, 32% yield) which was isolated as pale brown solid. $^1$H NMR (400 MHz, CD$_3$OD) δ ppm 9.36 (s, 1H), 8.84 (d, J=6.4 Hz, 2H), 8.34 (d, J=6.0 Hz, 2H), 8.28 (dd, J=8.8, 2.0 Hz, 1H), 7.86 (d, J=8.8 Hz, 1H), 7.52 (s, 1H), 2.76-2.81 (m, 2H), 1.69-1.72 (m, 3H), 1.04 (d, J=6.0 Hz, 6H); LCMS (ESI) m/e 309.2 [(M+H)$^+$, calcd for C$_{19}$H$_{21}$N$_2$S, 309.1]; LC/MS retention time (method B): t$_R$=1.51 min; HPLC retention time (method E): t$_R$=8.78 min.

Example 32

2-(3-methyl-1-(2,2,2-trifluoroethoxy)butyl)-6-(pyridin-4-yl)quinoline

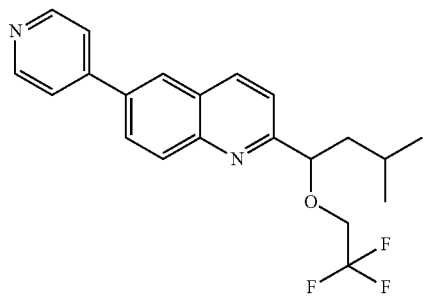 [SMILES: CC(C)CC(OCC(F)(F)F)c1ccc2cc(-c3ccncc3)ccc2n1]

Part A. 6-bromo-2-methylquinoline

To a solution of 4-bromoaniline (1.5 g, 8.72 mmol) in toluene (15 mL) was added conc. HCl (15 mL). The solution was heated to 100° C., then crotonaldehyde (1.44 mL, 17.44 mmol) was added dropwise and the mixture was stirred at 100° C. for 3 h. The reaction mixture was then cooled to room temperature and basified with saturated aqueous NaOH until the pH was neutral. The aqueous layer was extracted with ethyl acetate (3×50 mL). The combined organic layers were washed with brine (50 mL), dried over Na$_2$SO$_4$, filtered and concentrated under reduced pressure. The crude product was purified by column chromatography using a gradient of petroleum ether:Ethyl acetate to afford 6-bromo-2-methylquinoline (1.0 g, 4.5 mmol, 51% yield) as a pale brown solid. $^1$H NMR (400 MHz, CD$_3$OD) δ ppm 8.18 (d, J=8.4 Hz, 1H), 8.09 (d, J=2.0 Hz, 1H), 7.80-7.87 (m, 2H), 7.46 (d, J=8.4 Hz, 1H), 2.72 (s, 3H).

Part B. 2-methyl-6-(pyridin-4-yl)quinoline

To a solution of 6-bromo-2-methylquinoline (1 g, 4.50 mmol) in dioxane (2 mL) and water (2 mL), was added pyridine-4-boronic acid (0.83 g, 6.75 mmol) followed by Cs$_2$CO$_3$ (5.85 g, 18.01 mmol). Nitrogen gas was bubbled through the stirred suspension for 5 min then Pd(PPh$_3$)$_4$ (0.260 g, 0.22 mmol) was added. Nitrogen gas was again bubbled through the stirred suspension for 5 min and the reaction mixture was heated at 95° C. for 6 h. The reaction mixture was then cooled to room temperature and diluted with water (30 mL). The aqueous layer was extracted with ethyl acetate (3×100 mL). The combined organic layers were washed with brine (50 mL), dried over Na$_2$SO$_4$, filtered and concentrated under reduced pressure. The crude product was purified by column chromatography using petroleum ether:ethyl/acetate mobile phase to afford 2-methyl-6-(pyridin-4-yl)quinoline (500 mg, 2.26 mmol, 50% yield) as a brown solid. LCMS (ESI) m/e 221.2 [(M+H)$^+$, calcd for C$_{15}$H$_{13}$N$_2$, 221.10]; LC/MS retention time (method A): t$_R$=1.46 min.

Part C. 6-(pyridin-4-yl)quinoline-2-carbaldehyde

To the solution of 2-methyl-6-(pyridin-4-yl)quinoline (1 g, 4.50 mmol) in dioxane (20 mL) was added selenium dioxide (0.59 g, 6.75 mmol) and the reaction mixture was heated at 70° C. overnight. The reaction mixture was then cooled to room temperature, concentrated under reduced pressure and triturated with petroleum ether (20 mL) to afford 6-(pyridin-4-yl)quinoline-2-carbaldehyde (800 mg, 3.41 mmol, 76% yield) as a brown gum. LCMS (ESI) m/e 235.2 [(M+H)$^+$, calcd for $C_{15}H_{11}N_2O$, 235.1]; LC/MS retention time (method A): $t_R$=1.55 min.

Part D. 3-methyl-1-(6-(pyridin-4-yl)quinolin-2-yl)butan-1-ol

To a solution of 6-(pyridin-4-yl)quinoline-2-carbaldehyde (1.4 g, 5.98 mmol) in THF at −78° C. (20 mL) was added isobutyl magnesium bromide 2 M in THF (5.98 mL, 11.96 mmol) and the reaction mixture was stirred at −78° C. for 3 h. The reaction mixture was then quenched with aqueous NH$_4$Cl (20 mL). The mixture was extracted with ethyl acetate (3×50 mL). The combined organic layers were washed with brine (50 mL), dried over Na$_2$SO$_4$, filtered and concentrated under reduced pressure. The crude product was purified by column chromatography eluting with petroleum ether:Ethyl acetate to afford 3-methyl-1-(6-(pyridin-4-yl)quinolin-2-yl)butan-1-ol (1.0 g, 3.42 mmol, 57% yield). LCMS (ESI) m/e 293.2 [(M+H)$^+$, calcd for $C_{19}H_{21}N_2O$, 293.2]; LC/MS retention time (method A): $t_R$=1.74 min.

Part E. 2-(3-methyl-1-(2,2,2-trifluoroethoxy)butyl)-6-(pyridin-4-yl)quinoline

To a stirred solution of 3-methyl-1-(6-(pyridin-4-yl)quinolin-2-yl)butan-1-ol (50 mg, 0.17 mmol) in THF (2 mL) cooled to 0° C. was added NaH (26 mg, 0.68 mmol) followed by addition of 2,2,2-trifluoroethyl trifluoromethanesulfonate (78.9 mg, 0.34 mmol). The reaction mixture was allowed to warm to R.T. and stir at R.T. overnight. The reaction mixture was quenched with ice. The mixture was extracted with ethyl acetate (3×20 mL). The combined organic layers were washed with brine (50 mL), dried over Na$_2$SO$_4$, filtered and concentrated under reduced pressure. The crude product was purified by preparative HPLC (0.1% TFA in water and acetonitrile) to afford 2-(3-methyl-1-(2,2,2-trifluoroethoxy)butyl)-6-(pyridin-4-yl)quinoline, TFA (12 mg, 0.032 mmol, 19% yield) as a yellow solid. $^1$H NMR (400 MHz, CDCl$_3$) δ ppm 8.90 (s, 2H), 8.36 (d, J=8.4 Hz, 1H), 8.29 (d, J=8.8 Hz, 1H), 8.22 (s, 1H), 8.05 (d, J=8.4 Hz, 3H), 7.71 (d, J=8.4 Hz, 1H), 4.84-4.86 (m, 1H), 3.76-3.84 (m, 2H), 1.89-1.95 (m, 2H), 1.61-1.65 (m, 1H), 1.00-1.03 (m, 6H); LCMS (ESI) m/e 375.0 [(M+H)$^+$, calcd for $C_{21}H_{22}F_3N_2O$, 375.2]; LC/MS retention time (method C): $t_R$=2.14 min; HPLC retention time (method D): $t_R$=8.90 min; HPLC retention time (method C): $t_R$=8.02 min.

Example 33

N-(4-(2-(1-amino-3-methylbutyl)quinolin-6-yl)pyridin-2-yl)acetamide

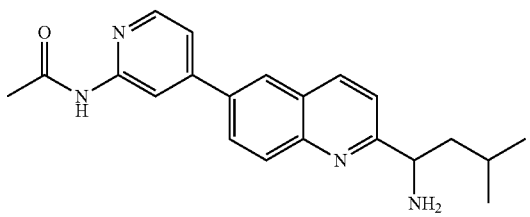 [SMILES: CC(=O)Nc1cc(-c2ccc3nc(C(N)CC(C)C)ccc3c2)ccn1]

Part A. N-(4-bromopyridin-2-yl)acetamide

To a solution of 4-bromopyridin-2-amine (4 g, 23.12 mmol) in DCM (40 mL), cooled to 0° C. was added pyridine (2.80 mL, 34.7 mmol) dropwise over a period of 10 min. The reaction mixture was stirred for 10 min at 0° C., then acetyl chloride (2.137 mL, 30.1 mmol) was added slowly. The reaction mixture was stirred at 0° C. for 1 h and brought to room temperature. After stirring at room temperature for 4 h the reaction mixture was diluted with water (20 mL) and extracted with DCM (2×20 mL). The combined organic layers were concentrated under reduced pressure to afford N-(4-bromopyridin-2-yl)acetamide (3.6 g, 16.74 mmol, 72.4% yield) as a light brown solid. LCMS (ESI) m/e 215.0, 217.0 Br pattern [(M+H)$^+$, calcd for $C_7H_8BrN_2O$, 215.0]; LC/MS retention time (method E): $t_R$=1.55 min.

Part B. N-(4-(2-methylquinolin-6-yl)pyridin-2-yl)acetamide

To a solution of 2-methyl-6-(4,4,5,5-tetramethyl-1,3,2-dioxaborolan-2-yl)quinoline (2.5 g, 9.29 mmol) in a solvent mixture of 1,4-dioxane (25 mL) and water (14 mL), was added Cs$_2$CO$_3$ (9.08 g, 27.9 mmol) followed by N-(4-bromopyridin-2-yl)acetamide (2.54 g, 11.15 mmol). Nitrogen gas was bubbled through the stirred suspension for 10 min and Pd(PPh$_3$)$_4$ (0.859 g, 0.743 mmol) was added and again nitrogen gas was bubbled through the stirred suspension for another 10 min. The reaction mixture was then heated at 100° C. for 12 h. The reaction mixture was cooled to room temperature and diluted with water (15 mL). The mixture was extracted with ethyl acetate (3×150 mL). The combined organic layers were washed with brine (50 mL), dried over Na$_2$SO$_4$, filtered and concentrated under reduced pressure. The crude product was purified by flash column chromatography (Mobile phase: ethyl acetate in petroleum ether) to afford N-(4-(2-methylquinolin-6-yl)pyridin-2-yl)acetamide (1.7 g, 6.13 mmol, 66% yield). LCMS (ESI) m/e 278.2 [(M+H)$^+$, calcd for $C_{17}H_{16}N_3O$, 278.1]; LC/MS retention time (method E): $t_R$=1.68 min.

Part C. N-(4-(2-formylquinolin-6-yl)pyridin-2-yl)acetamide

To a solution of N-(4-(2-methylquinolin-6-yl)pyridin-2-yl)acetamide (1.8 g, 6.49 mmol) in 1,4-dioxane (36 mL), was added selenium dioxide (0.864 g, 7.79 mmol) and the reaction mixture was heated at 75° C. for 4 h. The reaction mixture was then cooled to room temperature and filtered through diatomaceous earth (Celite®). The bed was washed with ethyl acetate. The combined organic layers were concentrated under reduced pressure to afford a solid which was washed with hexane (15 mL) to afford N-(4-(2-formylquinolin-6-yl)pyridin-2-yl)acetamide (1.2 g, 4.12 mmol, 64% yield). LCMS (ESI) m/e 292.2 [(M+H)$^+$, calcd for $C_{17}H_{14}N_3O_2$, 292.10]; LC/MS retention time (method E): $t_R$=1.67 min.

Part D. (E)-N-(4-(2-((tert-butylsulfinylimino)methyl)quinolin-6-yl)pyridin-2-yl)acetamide To a solution of N-(4-(2-formylquinolin-6-yl)pyridin-2-yl)acetamide (1.2 g, 4.12 mmol) in tetrahydrofuran (24 mL) was added ethyl orthotitanate (2.55 mL, 12.36 mmol). After stirring for 10 min at room temperature the reaction mixture was treated with (R)-(+) tert-butansulfinamide (0.599 g, 4.94 mmol) and heated at 75° C. for 4 h. The reaction mixture was then cooled to room temperature and diluted with brine (20 mL). The resultant mixture was passed through a diatomaceous earth) (Celite®) bed, eluting with ethyl acetate. The organic layer was separated, dried with sodium sulfate and concentrated under reduced pressure. The crude product was purified by flash column chromatography using a gradient of ethyl acetate in hexanes to afford (E)-N-(4-(2-(((tert-butyl-sulfinyl)imino)methyl)quinolin-6-yl)pyridin-2-yl)acetamide (950 mg, 2.408 mmol, 59% yield). LCMS (ESI) m/e 395.2 [(M+H)$^+$, calcd for $C_{21}H_{23}N_4O_2S$, 395.2]; LC/MS retention time (method E): $t_R$=1.79 min.

Part E. N-(4-(2-(1-(1,1-dimethylethylsulfinamido)-3-methylbutyl)quinolin-6-yl)pyridin-2-yl)acetamide (E)-N-(4-(2-(((tert-butylsulfinyl)imino)methyl)quinolin-6-yl)pyridin-2-yl)acetamide (660 mg, 1.673 mmol) was taken up in tetrahydrofuran (13 mL), cooled to −78° C. and stirred for 10 min. Isobutylmagnesium bromide (2M in diethyl ether, 1.673 mL, 3.35 mmol) was then added dropwise. The reaction mixture was stirred at −78° C. for 2 h, then the mixture was allowed to warm to room temperature and stirred for 2 h. The reaction mixture was quenched with saturated NH$_4$Cl (15 mL) and extracted with ethyl acetate (2×10 mL). The combined organic layers were dried with sodium sulfate, filtered and concentrated under reduced pressure to afford crude title compound (560 mg, 1.24 mmol, 74% yield) as a diastereomeric mixture. LCMS (ESI) m/e 453.2 [(M+H)$^+$, calcd for $C_{25}H_{33}N_4O_2S$, 453.22]; LC/MS retention time (method E): $t_R$=1.78 min and 1.91 min. The diastereomers were separated by preparative HPLC (10 mM ammonium acetate in water and acetonitrile) to afford two diastereomers: Isomer 1: N-(4-(2-(1-(1,1-dimethylethylsulfinamido)-3-methylbutyl)quinolin-6-yl)pyridin-2-yl)acetamide (isomer-1) (10 mg, 0.022 mmol) and Isomer 2: N-(4-(2-(1-(1,1-dimethylethylsulfinamido)-3-methylbutyl)quinolin-6-yl)pyridin-2-yl)acetamide (isomer-2) (20 mg, 0.044 mmol).

Part F. N-(4-(2-(1-amino-3-methylbutyl)quinolin-6-yl)pyridin-2-yl)acetamide

N-(4-(2-(1-(1,1-dimethylethylsulfinamido)-3-methylbutyl)quinolin-6-yl)pyridin-2-yl)acetamide (Isomer-1) (10 mg, 0.022 mmol) was taken in DCM (1 mL) and cooled to 0° C. then stirred for 10 min. To the solution was slowly added hydrochloric acid (2 M in diethyl ether, 10 uL, 0.022 mmol) and the reaction mixture was stirred at 0° C. for 10 min. The ice bath was removed and the reaction was brought to room temperature and stirred for 2 h. The mixture was concentrated under reduced pressure and the residue was purified by preparative HPLC (0.1% TFA in water and acetonitrile) to afford N-(4-(2-(1-amino-3-methylbutyl)quinolin-6-yl)pyridin-2-yl)acetamide, TFA (6 mg, 0.017 mmol, 78% yield) as a brown solid. $^1$H NMR (400 MHz, CD$_3$OD) δ ppm 8.57 (d, J=8.4 Hz, 1H), 8.44-8.48 (m, 2H), 8.30 (d, J=8.8 Hz, 1H), 8.21-8.25 (m, 2H), 7.8 (d, J=6.0 Hz, 1H), 7.67 (d, J=8.4 Hz, 1H), 4.75 (t, J=7.2 Hz, 1H), 2.32 (s, 3H), 1.89-2.01 (m, 2H), 1.70-1.74 (m, 1H), 1.04-1.09 (m, 6H); LCMS (ESI) m/e 349.2 [(M+H)$^+$, calcd for $C_{21}H_{25}N_4O$, 349.2]; LC/MS retention time (method A): $t_R$=1.39 min; HPLC retention time (method B): $t_R$=10.42 min; HPLC retention time (method A): $t_R$=9.76 min; Chiral SFC (method A1): $t_R$=4.21 min.

Example 34

N-(4-(2-(1-amino-3-methylbutyl)quinolin-6-yl)pyridin-2-yl)acetamide

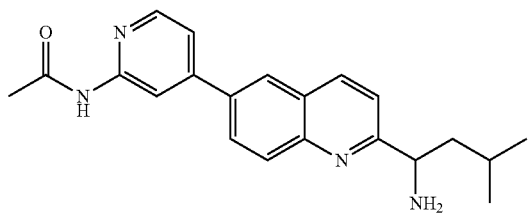 [SMILES: CC(=O)Nc1cc(-c2ccc3nc(C(N)CC(C)C)ccc3c2)ccn1]

Prepared in a similar fashion as described above in Example 33, Part F using N-(4-(2-(1-(1,1-dimethylethylsulfinamido)-3-methylbutyl)quinolin-6-yl)pyridin-2-yl)acetamide (Isomer-2) (20 mg, 0.044 mmol) to afford N-(4-(2-(1-amino-3-methylbutyl)quinolin-6-yl)pyridin-2-yl)acetamide, HCl (6 mg, 0.017 mmol, 39% yield) as an off-white solid. $^1$H NMR (400 MHz, CD$_3$OD) δ ppm 8.63 (s, 2H) 8.47 (d, J=5.2 Hz, 1H), 8.27-8.36 (m, 2H), 8.09 (d, J=5.2 Hz, 1H), 7.88 (s, 1H), 7.72 (d, J=8.0 Hz, 1H), 4.76-4.79 (m, 1H), 2.41 (s, 3H), 1.90-2.02 (m, 2H), 1.68-1.75 (m, 1H), 1.05-1.07 (m, 6H); LCMS (ESI) m/e 349.2 [(M+H)$^+$, calcd for $C_{21}H_{25}N_4O$, 349.2]; LC/MS retention time (method A): $t_R$=1.28 min; HPLC retention time (method A): $t_R$=9.57 min; HPLC retention time (method B): $t_R$=10.14 min; Chiral SFC (method A2): $t_R$=3.84 min.

Example 35

N-(4-(2-(1-amino-3-methylbutyl)quinolin-6-yl)pyridin-2-yl)-3-fluorobenzamide

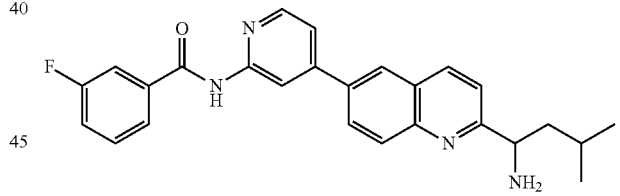

Part A. N-(4-bromopyridin-2-yl)-3-fluorobenzamide

A solution of 3-fluorobenzoic acid (100 mg, 0.714 mmol) in sulfurous dichloride (255 mg, 2.141 mmol) was heated at 65° C. for 1 h, then concentrated under reduced pressure in a N$_2$ atmosphere to afford 3-fluorobenzoyl chloride as an oil, which was kept under N$_2$ until needed. In separate single neck round bottom flask 4-bromopyridin-2-amine (149 mg, 0.864 mmol) was taken up in DCM (4 mL). To this stirred solution at room temperature, was added DIEA (0.125 mL, 0.714 mmol). The solution was then cooled to 0° C. and a solution of the 3-fluorobenzoyl chloride in DCM (1 mL) was added dropwise. The reaction mixture was then allowed to stir at room temperature for 7 h. The reaction mixture was quenched with ice water (10 mL) and extracted with ethyl acetate (3×3 mL). The combined organic layers were washed with water (10 mL), dried over Na$_2$SO$_4$ and evaporated under reduced pressure to afford N-(3-bromophenyl)-

3-fluorobenzamide (30 mg, 0.078 mmol, 11% yield). The crude product was taken into the next step without purification. LCMS (ESI) m/e 295.0 [(M+H)⁺, calcd for $C_{12}H_9BrFN_2O$, 294.98]; LC/MS retention time (method E): $t_R$=1.94 min.

Part B. N-(4-(2-(1-(1,1-dimethylethylsulfinamido)-3-methylbutyl)quinolin-6-yl)pyridin-2-yl)-3-fluorobenzamide Prepared in a similar fashion as described in Example 25, Part E using 2-methyl-N-(3-methyl-1-(6-(trimethylstannyl)quinolin-2-yl)butyl)propane-2-sulfinamide (Preparation described in Example 25, Part D) (100 mg, 0.208 mmol) and N-(4-bromopyridin-2-yl)-3-fluorobenzamide (73.6 mg, 0.249 mmol) to afford N-(4-(2-(1-(1,1-dimethylethylsulfinamido)-3-methylbutyl)quinolin-6-yl)pyridin-2-yl)-3-fluorobenzamide (120 mg, 0.034 mmol, 16% yield). The crude product was taken into the next without purification. LCMS (ESI) m/e 533.2 [(M+H)⁺, calcd for $C_{30}H_{34}FN_4O_2S$, 533.23]; LC/MS retention time (method E): $t_R$=2.25 min.

Part C. N-(4-(2-(1-amino-3-methylbutyl)quinolin-6-yl)pyridin-2-yl)-3-fluorobenzamide Prepared in a similar fashion as described in Example 25, Part E using N-(4-(2-(1-(1,1-dimethylethylsulfinamido)-3-methylbutyl)quinolin-6-yl)pyridin-2-yl)-3-fluorobenzamide (120 mg, 0.225 mmol). The crude product was purified by preparative HPLC (0.1% TFA in water and acetonitrile) to afford N-(4-(2-(1-amino-3-methylbutyl)quinolin-6-yl)pyridin-2-yl)-3-fluorobenzamide, TFA (10 mg, 0.022 mmol, 10% yield). ¹H NMR (400 MHz, DMSO-d₆) δ ppm 7.89 (s, 1H), 7.70-7.76 (m, 2H), 7.64 (s, 1H), 7.42-7.50 (m, 2H), 7.08 (d, J=7.2 Hz, 1H), 6.98-7.00 (m, 1H), 6.79-6.88 (m, 3H), 6.58-6.61 (m, 1H), 3.92-3.96 (m, 1H), 1.09-1.23 (m, 2H), 0.89-1.93 (m, 1H), 0.23-0.28 (m, 6H); LCMS (ESI) m/e 429.2 [(M+H)⁺, calcd for $C_{26}H_{26}FN_4O$, 429.20]; LC/MS retention time (method C): $t_R$=1.85 min; HPLC retention time (method D): $t_R$=8.04 min; HPLC retention time (method C): $t_R$=6.68 min.

Example 36

4-(2-(amino(cyclohexyl)methyl)quinolin-6-yl)-N-(prop-1-en-2-yl)pyridin-2-amine

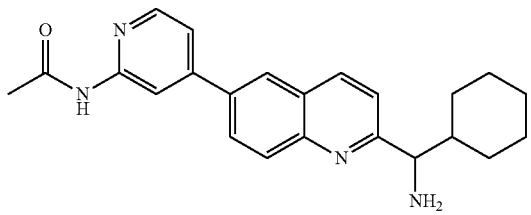 [SMILES: CC(=O)Nc1cc(-c2ccc3nc(C(N)C4CCCCC4)ccc3c2)ccn1]

Part A. N-(4-(2-(cyclohexyl(1,1-dimethylethylsulfinamido)methyl)quinolin-6-yl)pyridin-2-yl)-N-methylacetamide Prepared as described in Example 33, Parts E and F to afford 4-(2-(amino(cyclohexyl)methyl)quinolin-6-yl)-N-(prop-1-en-2-yl)pyridin-2-amine, TFA (160 mg, 0.334 mmol, 5% yield over two steps) as a pale light yellow solid.

¹H NMR (400 MHz, CD₃OD) δ ppm 8.44-8.54 (m, 3H) 8.27-8.31 (m, 2H) 8.22 (dd, J=8.8, 2.0 Hz, 1H) 7.79 (d, J=4.4 Hz, 1H) 7.63 (d, J=8.4 Hz, 1H) 4.51 (d, J=6.4 Hz, 1H) 2.32 (s, 3H) 2.07-2.11 (m, 1H) 1.63-1.87 (m, 5H) 1.13-1.41 (m, 5H); LCMS (ESI) m/e 375.2 [(M+H)⁺, calcd for $C_{23}H_{27}N_4O$, 375.2]; LC/MS retention time (method B): $t_R$=1.59 min; HPLC retention time (method B): $t_R$=11.70 min; HPLC retention time (method A): $t_R$=10.83 min.

Example 37

3-methyl-1-(6-(pyridin-4-yl)-4-(1H-tetrazol-5-yl)quinolin-2-yl)butan-1-amine

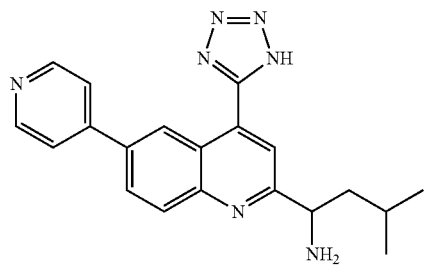 [SMILES: CC(C)CC(N)c1cc(-c2nnn[nH]2)c2cc(-c3ccncc3)ccc2n1]

Part A.
4-bromo-2-isopentyl-6-(pyridin-4-yl)quinoline

To a suspension of 2-isopentyl-6-(pyridin-4-yl)quinolin-4(1H)-one (2.2 g, 7.52 mmol) (prepared as described in Example 31, Part D) in DMF (40 mL) at room temperature was carefully added PBr₃ (0.710 mL, 7.52 mmol) dropwise, at such a rate as to keep the reaction from foaming over. After complete addition, the reaction mixture was stirred at room temperature for 20 min then quenched with ice water. The resultant mixture was stirred at room temperature for 30 min. The pH of the mixture was adjusted to pH=8 by the addition of 1N NaOH. The mixture was transferred to a separatory funnel containing saturated aqueous NaHCO₃ (45 mL) and the aqueous layer was extracted with CH₂Cl₂ containing 10% MeOH (2×50 mL). The combined organic layers were washed with brine (50 mL), dried over MgSO₄, filtered, and concentrated under reduced pressure. The residue was purified by column chromatography on silica gel (2%→7% methanol in CH₂Cl₂) to afford 4-bromo-2-isopentyl-6-(pyridin-4-yl)quinoline (1.87 g, 4.48 mmol, 60% yield) as an orange oil that solidified upon standing. LCMS (ESI) m/e 355.0 [(M+H)⁺, calcd for $C_{19}H_{20}BrN_2$, 355.07]; LC/MS retention time (method E): $t_R$=2.34 min.

Part B. 4-bromo-2-(1-bromo-3-methylbutyl)-6-(pyridin-4-yl)quinoline

To a solution of 4-bromo-2-isopentyl-6-(pyridin-4-yl)quinoline (0.567 g, 1.596 mmol) and AIBN (0.052 g, 0.318 mmol) in CCl₄ (15 mL) was added NBS (0.312 g, 1.754 mmol). The reaction mixture was then heated at 75° C. for 3.5 h. Additional NBS (340 mg) and AIBN (99 mg) were added and stirring was continued for an additional 2.5 h. The mixture was then cooled to room temperature and transferred to a separatory funnel containing saturated aqueous NaHCO₃. The aqueous layer was extracted with DCM (15 mL). The combined organic layers were washed with brine (10 mL), dried over Na₂SO₄, filtered, and concentrated under reduced pressure. The residue was purified by column chromatography on silica gel (2%→7% methanol in $CH_2Cl_2$; 12 g column) to afford 4-bromo-2-(1-bromo-3-methylbutyl)-6-(pyridin-4-yl)quinoline (0.277 g, 0.268 mmol, 17% yield) as a brown solid. LCMS (ESI) m/e 433.0, 435.0 di-bromo pattern [(M+H)$^+$, calcd for $C_{19}H_{19}Br_2N_2$, 433.0]; LC/MS retention time (method E): $t_R$=2.44 min.

Part C. 2-(1-azido-3-methylbutyl)-4-bromo-6-(pyridin-4-yl)quinoline

A solution of 4-bromo-2-(1-bromo-3-methylbutyl)-6-(pyridin-4-yl)quinoline (0.277 g, 0.638 mmol) in acetone (2.5 mL) was treated with sodium azide (0.166 g, 2.55 mmol). The mixture was heated at 70° C. for 2.75 h. The reaction mixture was cooled to room temperature and transferred to a separatory funnel containing water. The aqueous layer was extracted with $CH_2Cl_2$ (2×10 mL) and the combined organic extracts were washed with brine, dried over $Na_2SO_4$, filtered, and concentrated under reduced pressure to afford 2-(1-azido-3-methylbutyl)-4-bromo-6-(pyridin-4-yl)quinoline (0.130 g, 0.233 mmol, 37% yield) as an oil. The crude material was carried on without further purification. LCMS (ESI) m/e 396.0, 398.0 Br pattern [(M+H)$^+$, calcd for $C_{19}H_{19}BrN_5$, 396.1]; LC/MS retention time (method E): $t_R$=2.39 min.

Part D. 1-(4-bromo-6-(pyridin-4-yl)quinolin-2-yl)-3-methylbutan-1-amine

To a solution of 2-(1-azido-3-methylbutyl)-4-bromo-6-(pyridin-4-yl)quinoline (0.130 g, 0.328 mmol) in THF (2 mL) was added triphenylphosphine (0.172 g, 0.656 mmol). The mixture was stirred at room temperature for 3 h. Water (0.1 mL, 5.55 mmol) was added and the mixture was heated at 50° C. for 24 h. The reaction mixture was then cooled to room temperature and concentrated under reduced pressure to afford 1-(4-bromo-6-(pyridin-4-yl)quinolin-2-yl)-3-methylbutan-1-amine (0.15 g, 0.158 mmol, 48% yield). The crude product was taken into the next step without purification. LCMS (ESI) m/e 370.0, 372.0 Br pattern [(M+H)$^+$, calcd for $C_{19}H_{21}BrN_3$, 370.1]; LC/MS retention time (method E): $t_R$=1.78 min.

Part E. tert-butyl 1-(4-bromo-6-(pyridin-4-yl)quinolin-2-yl)-3-methylbutylcarbamate A solution of 1-(4-bromo-6-(pyridin-4-yl)quinolin-2-yl)-3-methylbutan-1-amine (0.150 g, 0.405 mmol) in tetrahydrofuran (5 mL) was cooled to 0° C. and treated with DIEA (0.354 mL, 2.025 mmol). The reaction mixture was stirred for 10 min and then treated with (BOC)$_2$O (0.103 mL, 0.446 mmol). The resultant solution was stirred at room temperature under nitrogen for 14 h. The reaction mixture was then diluted with water and extracted with dichloromethane (2×10 mL). The combined organic layers were washed with water, brine, dried over $Na_2SO_4$ and concentrated under reduced pressure to afford tert-butyl (1-(4-bromo-6-(pyridin-4-yl)quinolin-2-yl)-3-methylbutyl)carbamate (0.171 g, 0.364 mmol, 90% yield). The crude product was taken to next step without purification. LCMS (ESI) m/e 470.2, 472.2 Br pattern [(M+H)$^+$, calcd for $C_{24}H_{29}BrN_3O_2$, 470.1]; LC/MS retention time (method E): $t_R$=2.25 min.

Part F. tert-butyl 1-(4-cyano-6-(pyridin-4-yl)quinolin-2-yl)-3-methylbutylcarbamate Tert-butyl (1-(4-bromo-6-(pyridin-4-yl)quinolin-2-yl)-3-methylbutyl)carbamate (0.15 g, 0.319 mmol) was dissolved in DMF (5 mL) and water (0.25 mL, 13.88 mmol). The mixture was degassed by sonication for 5 min. The resultant solution was treated sequentially with zinc cyanide (0.039 g, 0.332 mmol), trisdibenzylideneacetone (0.330 g, 0.319 mmol) and DPPF (0.177 g, 0.319 mmol) and the reaction mixture was heated at 120° C. under $N_2$ for 1.25 h. The reaction mixture was cooled to room temperature and transferred to a reparatory funnel containing diethyl ether (10 mL). The organic layer was separated and washed with water (10 mL). The combined organic layers were washed with brine (10 mL), dried over $Na_2SO_4$, filtered, and concentrated under reduced pressure. The residue was purified by preparative TLC on silica gel using 5% methanol in $CH_2Cl_2$ mobile phase to afford tert-butyl (1-(4-cyano-6-(pyridin-4-yl)quinolin-2-yl)-3-methylbutyl)carbamate (0.080 g, 0.192 mmol, 60% yield). LCMS (ESI) m/e 417.2 [(M+H)$^+$, calcd for $C_{25}H_{29}N_4O_2$, 417.2]; LC/MS retention time (method E): $t_R$=2.10 min.

Part G. tert-butyl 3-methyl-1-(6-(pyridin-4-yl)-4-(2H-tetrazol-5-yl)quinolin-2-yl)butylcarbamate To a solution of tert-butyl (1-(4-cyano-6-(pyridin-4-yl)quinolin-2-yl)-3-methylbutyl)carbamate (0.080 g, 0.192 mmol) in DMF (1 mL) was added ammonium chloride (0.062 g, 1.152 mmol) and sodium azide (0.075 g, 1.152 mmol). The reaction mixture was heated at 100° C. for 2 h. The reaction mixture was cooled to room temperature and diluted with water (10 mL). The aqueous layer was washed with ethyl acetate (2×10 mL), then the aqueous layer was concentrated under reduced pressure to afford a solid. The solid was dissolved in methanol, dried over sodium sulfate, filtered and concentrated under reduced pressure to afford tert-butyl (3-methyl-1-(6-(pyridin-4-yl)-4-(2H-tetrazol-5-yl)quinolin-2-yl)butyl)carbamate (0.045 g, 0.098 mmol, 51% yield). The crude product was taken into the next step without further purification. LCMS (ESI) m/e 460.2 [(M+H)$^+$, calcd for $C_{25}H_{30}N_7O_2$, 460.2]; LC/MS retention time (method E): $t_R$=1.65 min.

Part H. 3-methyl-1-(6-(pyridin-4-yl)-4-(1H-tetrazol-5-yl)quinolin-2-yl)butan-1-amine A solution of tert-butyl (3-methyl-1-(6-(pyridin-4-yl)-4-(2H-tetrazol-5-yl)quinolin-2-yl)butyl)carbamate (0.04 g, 0.087 mmol) in methanol (1 mL) was cooled to 0° C. under nitrogen and stirred for 10 min. Hydrogen chloride, 2M solution in diethyl ether (5 ml, 0.00 mmol) was then added dropwise. The solution was warmed to room temperature and stirred for 2 h. The reaction mixture was concentrated under reduced pressure. Water (10 mL) was added to the residue and the resultant solution was washed with diethyl ether (5 mL) ethyl acetate (5 mL). The aqueous layer was concentrated under reduced pressure and the residue was purified by preparative HPLC (0.1% TFA in water/AcCN) to afford a 3-methyl-1-(6-(pyridin-4-yl)-4-(2H-tetrazol-5-yl) quinolin-2-yl)butan-1-amine, TFA (0.006 g, 0.017 mmol, 19% yield) as a reddish solid. $^1$H NMR (400 MHz, CD$_3$OD) δ ppm 9.57 (d, J=1.6 Hz, 1H), 8.85 (d, J=6.4 Hz, 2H), 8.36-8.44 (m, 2H), 8.31 (d, J=6.0 Hz, 2H), 8.22 (s, 1H), 4.80-4.82 (m, 1H), 1.92-2.10 (m, 2H), 1.73-1.80 (m, 1H), 1.07-1.11 (m, 6H); LCMS (ESI) m/e 360.2 [(M+H)$^+$, calcd for $C_{22}H_{22}N_7$, 360.19]; LC/MS retention time (method E): $t_R$=1.46 min; HPLC retention time (method B): $t_R$=8.11 min; HPLC retention time (method A): $t_R$=7.90 min.

Example 38

4-(2-(1-amino-3-methylbutyl)quinolin-6-yl)-N-cyclopropylpyridin-2-amine

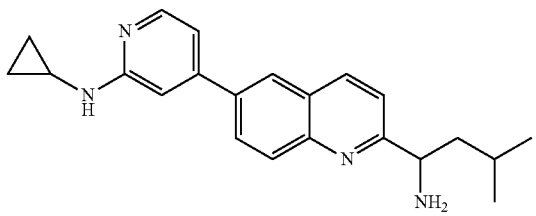 [SMILES: CC(C)CC(N)c1ccc2cc(-c3ccnc(NC4CC4)c3)ccc2n1]

Part A. 4-bromo-N-cyclopropylpyridin-2-amine

To a solution of 4-bromo-2-fluoropyridine (100 mg, 0.568 mmol) in DMF (2 mL) was added cesium carbonate (185 mg, 0.568 mmol) followed by cyclopropanamine (97 mg, 1.705 mmol). The reaction mixture was heated at 100° C. for 8 h. The reaction mixture was cooled to room temperature, quenched with water (5 mL), and extracted with ethyl acetate (3×5 mL). The combined organic layers were washed with water (10 mL), then with brine (10 mL) dried over $Na_2SO_4$ and evaporated under reduced pressure to afford 4-bromo-N-cyclopropylpyridin-2-amine (10 mg, 10.33 μmol, 2% yield). LCMS (ESI) m/e 213.0, 215.0 Bromide pattern [(M+H)$^+$, calcd for $C_8H_{10}BrN_2$, 213.0]; LC/MS retention time (method B): $t_R$=0.84 min.

Part B. N-(1-(6-(2-(cyclopropylamino)pyridin-4-yl)quinolin-2-yl)-3-methylbutyl)-2-methylpropane-2-sulfinamide Prepared in a similar fashion as described in Example 25, Part E using 2-methyl-N-(3-methyl-1-(6-(trimethylstannyl)quinolin-2-yl)butyl)propane-2-sulfinamide (90 mg, 0.19 mmol) and 4-bromo-N-cyclopropylpyridin-2-amine (47.8 mg, 0.22 mmol) to afford N-(1-(6-(2-(cyclopropylamino)pyridin-4-yl)quinolin-2-yl)-3-methylbutyl)-2-methylpropane-2-sulfinamide (15 mg, 0.019 mmol, 10% yield). LCMS (ESI) m/e 451.2 [(M+H)$^+$, calcd for $C_{26}H_{35}N_4OS$, 451.2]; LC/MS retention time (method C): $t_R$=2.06 min.

Part C. 4-(2-(1-amino-3-methylbutyl)quinolin-6-yl)-N-cyclopropylpyridin-2-amine Prepared in a similar fashion as described in Example 25, Part F using N-(1-(6-(2-(cyclopropylamino)pyridin-4-yl)quinolin-2-yl)-3-methylbutyl)-2-methylpropane-2-sulfinamide (75 mg, 0.166 mmol). The crude product was purified by preparative HPLC (0.1% TFA in water and acetonitrile) to afford 4-(2-(1-amino-3-methylbutyl)quinolin-6-yl)-N-cyclopropylpyridin-2-amine, TFA (13 mg, 0.036 mmol, 22% yield) as a pale yellow oil. $^1$H NMR (400 MHz, CD$_3$OD) δ ppm 8.55-8.60 (m, 1H), 8.47 (d, J=2.0 Hz, 1H), 8.30 (d, J=8.8 Hz, 1H), 8.19 (dd, J=8.8, 2.4 Hz, 1H), 8.05 (dd, J=6.8.0.4 Hz, 1H), 7.68 (d, J=8.8 Hz, 1H), 7.42-7.46 (m, 2H), 4.75 (t, J=7.2 Hz, 1H), 2.78-2.80 (m, 1H), 1.90-1.98 (m, 2H), 1.70-1.72 (m, 1H), 1.03-1.10 (m, 8H), 0.79-0.82 (m, 2H); LCMS (ESI) m/e 347.2 [(M+H)$^+$, calcd for $C_{22}H_{27}N_4$, 347.2]; LC/MS retention time (method B): $t_R$=1.40 min; HPLC retention time (method A): $t_R$=9.11 min; HPLC retention time (method B): $t_R$=10.31 min; Chiral HPLC (method B1): $t_R$=10.93 min.

Example 39

2-(amino(cyclohexyl)methyl)-6-(pyridin-4-yl)quinoline-4-carboxamide

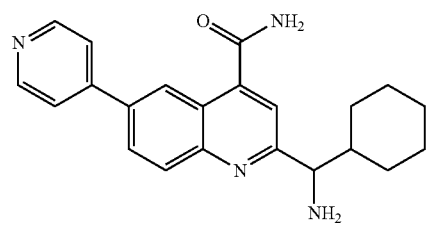 [SMILES: NC(=O)c1cc(C(N)C2CCCCC2)nc2ccc(-c3ccncc3)cc12]

Part A. 6-bromo-2-methylquinoline-4-carboxylic acid

To 5-bromoindoline-2,3-dione (800 mg, 3.54 mmol) in a round bottom flask was added KOH (1589 mg, 28.3 mmol) in water (3.2 mL) and the resultant solution was stirred for 10 min. To this solution acetone (5.98 mL, 81 mmol) was added and the reaction mixture was heated at 75° C. for 5 h. The reaction mixture was then cooled to room temperature, neutralized to pH 5-6 using 10% HCl. The precipitate that formed was collected by vacuum filtration and dried under vacuum to afford 6-bromo-2-methylquinoline-4-carboxylic acid (500 mg, 1.879 mmol, 53% yield). $^1$H NMR (400 MHz, DMSO-d$_6$) δ ppm 14.04 (s, 1H) 8.93 (s, 1H) 7.95 (d, J=8.8 Hz, 3H) 2.72 (s, 3H).

Part B. 6-bromo-2-methylquinoline-4-carboxamide

To a solution of 6-bromo-2-methylquinoline-4-carboxylic acid (9.7 g, 36.5 mmol) in DMF (2 mL) at 0° C. was added EDC (10.48 g, 54.7 mmol), HOBT (11.16 g, 72.9 mmol) and ammonium chloride (4.87 g, 91 mmol) and the mixture was stirred for 10 min. DIEA (19.10 mL, 109 mmol) was then added and the solution stirred at room temperature for 12 h. The reaction mixture was quenched with ice and the solid collected by vacuum filtration to afford 6-bromo-2-methylquinoline-4-carboxamide (8.1 g, 30.6 mmol, 84% yield) as a solid. LCMS (ESI) m/e 265.0, 267.0 Br pattern [(M+H)$^+$, calcd for $C_{11}H_{10}BrN_2O$, 265.0]; LC/MS retention time (method A): $t_R$=1.21 min.

Part C. 2-methyl-6-(pyridin-4-yl)quinoline-4-carboxamide

To a solution of 6-bromo-2-methylquinoline-4-carboxamide (2 g, 7.54 mmol) in 1,4-dioxane (20 mL) and water (10 mL), was added 4-pyridylboronic acid (1.855 g, 15.09 mmol) and cesium carbonate (7.37 g, 22.63 mmol). Nitrogen gas was bubbled through the stirred suspension for 10 min. Pd(PPh$_3$)$_4$ (0.697 g, 0.604 mmol) was added and again nitrogen gas was bubbled through the stirred suspension for 10 min. The reaction mixture was then heated at 95° C. for 12 h. The reaction mixture was quenched with ice and stirred for 10 min. The solid obtained was collected by vacuum filtration and washed with petroleum ether (20 mL) and ethyl acetate (20 mL) then dried under vacuum to afford 2-methyl-6-(pyridin-4-yl)quinoline-4-carboxamide (1.6 g, 6.08 mmol, 81% yield). LCMS (ESI) m/e 262.0 [(M–H)⁻, calcd for C₁₆H₁₂N₃O, 262.1]; LC/MS retention time (method A): t_R=1.03 min.

Part D.
2-formyl-6-(pyridin-4-yl)quinoline-4-carboxamide

To a solution of 2-methyl-6-(pyridin-4-yl)quinoline-4-carboxamide (1.6 g, 6.08 mmol) in 1,4-dioxane (32 mL) was added selenium dioxide (0.809 g, 7.29 mmol) and the mixture was heated to 75° C. and stirred for 12 h. The reaction mixture was filtered through a diatomaceous earth (Celite®) bed, washing the bed with DCM (30 mL) and methanol (20 mL). The combined organic layers were concentrated under reduced pressure to afford 2-formyl-6-(pyridin-4-yl)quinoline-4-carboxamide (1.4 g, 5.05 mmol, 83% yield). LCMS (ESI) m/e 276.0 [(M–H)⁻, calcd for C₁₆H₁₀N₃O₂, 276.09]; LC/MS retention time (method A): t_R=1.12 min.

Part E. (E)-2-((tert-butylsulfinylimino)methyl)-6-(pyridin-4-yl)quinoline-4-carboxamide Prepared in a similar fashion as described in Example 33, Part D using 2-formyl-6-(pyridin-4-yl)quinoline-4-carboxamide (1.4 g, 5.05 mmol) to afford (E)-2-((tert-butylsulfinylimino)methyl)-6-(pyridin-4-yl)quinoline-4-carboxamide (1.5 g, 3.94 mmol, 78% yield). The crude product was taken into the next step without purification. LCMS (ESI) m/e 381.0 [(M+H)⁺, calcd for C₂₀H₂₁N₄O₂S, 381.1]; LC/MS retention time (method A): t_R=1.32 min.

Part F. 2-(cyclohexyl(1,1-dimethylethylsulfinamido)methyl)-6-(pyridin-4-yl)quinoline-4-carboxamide Prepared in a similar fashion as described in Example 36, Part A using (E)-2-(((tert-butylsulfinyl)imino)methyl)-6-(pyridin-4-yl)quinoline-4-carboxamide (1 g, 2.63 mmol). LCMS (ESI) m/e 465.0 [(M+H)⁺, calcd for C₂₆H₃₃N₄O₂S, 465.22]; LC/MS retention time (method A): t_R=1.48 min, 1.75 min (two diastereomers). The diastereomers were separated via preparative HPLC (10 mM ammonium acetate in water and acetonitrile) to afford isomer 1: 2-(cyclohexyl(1,1-dimethylethylsulfinamido)methyl)-6-(pyridin-4-yl)quinoline-4-carboxamide (30 mg, 0.065 mmol, 2% yield) and isomer 2: 2-(cyclohexyl(1,1-dimethylethylsulfinamido)methyl)-6-(pyridin-4-yl)quinoline-4-carboxamide (300 mg, 0.646 mmol, 25% yield).

Part G. 2-(amino(cyclohexyl)methyl)-6-(pyridin-4-yl)quinoline-4-carboxamide

Prepared in a similar fashion as described in Example 33, Part F using 2-(cyclohexyl(1,1-dimethylethylsulfinamido)methyl)-6-(pyridin-4-yl)quinoline-4-carboxamide (isomer-1) (30 mg, 0.065 mmol). The crude product was purified by preparative HPLC (0.1% TFA in water and acetonitrile) to afford optically pure 2-(amino(cyclohexyl)methyl)-6-(pyridin-4-yl)quinoline-4-carboxamide, TFA (12 mg, 0.033 mmol, 51.6% yield) as a yellow solid. ¹H NMR (400 MHz, CD₃OD) δ ppm 8.95 (d, J=6.8 Hz, 2H), 8.88 (d, J=1.2 Hz, 1H), 8.49 (d, J=6.8, Hz, 2H), 8.38-8.43 (m, 2H), 7.79 (s, 1H), 4.59 (d, J=6.4 Hz, 1H), 2.14-2.17 (m, 1H), 1.70-1.88 (m, 5H), 1.19-1.37 (m, 5H); LCMS (ESI) m/e 361.0 [(M+H)⁺, calcd for C₂₂H₂₅N₄O, 361.2]; LC/MS retention time (method A): t_R=1.18 min; HPLC retention time (method A): t_R=7.27 min; HPLC retention time (method B): t_R=8.11 min; Chiral SFC (method B1): t_R=6.59 min. The absolute stereochemistry of the isomer was not determined.

Example 40

2-(amino(cyclohexyl)methyl)-6-(pyridin-4-yl)quinoline-4-carboxamide

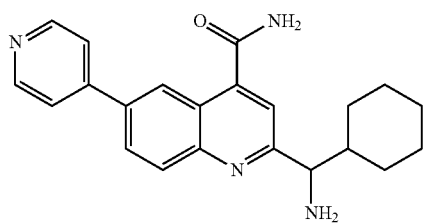 [SMILES: NC(=O)c1cc(C(N)C2CCCCC2)nc2ccc(-c3ccncc3)cc12]

Prepared in a similar fashion as described in Example 33, Part F using 2-(cyclohexyl(1,1-dimethylethylsulfinamido)methyl)-6-(pyridin-4-yl)quinoline-4-carboxamide (isomer-2, prepared as described in Example 39. Part F) (30 mg, 0.065 mmol) to afford optically pure 2-(amino(cyclohexyl)methyl)-6-(pyridin-4-yl)quinoline-4-carboxamide, TFA (12 mg, 0.033 mmol, 52% yield) as a yellow solid. ¹H NMR (400 MHz, CD₃OD) δ ppm 8.96 (d, J=6.8 Hz, 2H), 8.90 (s, 1H), 8.53 (d, J=6.8, Hz, 2H), 8.41 (d, J=2.0 Hz, 2H), 7.80 (s, 1H), 4.60 (d, J=6.4 Hz, 1H), 2.15-2.19 (m, 1H), 1.80-1.87 (m, 3H), 1.70-1.72 (m, 2H), 1.19-1.36 (m, 5H); LCMS (ESI) m/e 361.2 [(M+H)⁺, calcd for C₂₂H₂₅N₄O, 361.2]; LC/MS retention time (method B): t_R=1.09 min; HPLC retention time (method A): t_R=7.14 min; HPLC retention time (method B): t_R=8.04 min; Chiral SFC (method B1): t_R=4.83 min. The absolute stereochemistry of the isomer was not determined.

Example 41

2-(amino(cyclohexyl)methyl)-6-(pyridin-4-yl)quinoline-4-carbonitrile

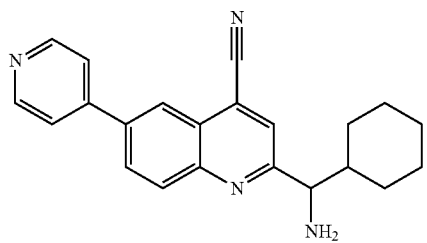 [SMILES: N#Cc1cc(C(N)C2CCCCC2)nc2ccc(-c3ccncc3)cc12]

Part A. 2-(amino(cyclohexyl)methyl)-6-(pyridin-4-yl)quinoline-4-carbonitrile 2-(Cyclohexyl(1,1-dimethylethylsulfinamido)methyl)-6-(pyridin-4-yl)quinoline-4-carboxamide (20 mg, 0.043 mmol) (prepared racemically as described in Example 39, Part F) was taken up in methylene dichloride (1 mL) and cooled to 0° C. To this was added 2M HCl in diethyl ether (0.1 mL, 0.2 mmol) and the reaction mixture was stirred at that temperature for 10 min. The reaction mixture was allowed to warm to rt and stirring was continued for 2 h. The mixture was concentrated under reduced pressure and the residue was purified by preparative HPLC (0.1% TFA in water and acetonitrile) to afford 2-(amino(cyclohexyl)methyl)-6-(pyridin-4-yl)quinoline-4-carbonitrile, TFA (8 mg, 0.023 mmol, 54% yield) as a pale yellow solid. $^1$H NMR (400 MHz, CD$_3$OD) δ ppm 8.91 (d, J=6.4 Hz, 2H), 8.67 (d, J=1.6 Hz, 1H), 8.55-8.58 (m, 2H), 8.35-8.50 (m, 1H), 8.34 (d, J=6.4 Hz, 2H), 4.10-4.15 (m, 1H), 2.02-2.04 (m, 2H), 1.90-1.93 (m, 2H), 1.81-1.84 (m, 1H), 1.48-1.62 (m, 4H), 1.30-1.40 (m, 2H); LCMS (ESI) m/e 341.2 [(M−H)$^-$, calcd for C$_{22}$H$_{21}$N$_4$, 341.2]; LC/MS retention time (method E): $t_R$=2.25 min; HPLC retention time (method C): $t_R$=9.99 min; HPLC retention time (method D): $t_R$=9.70 min.

Example 42

N-(4-(2-(1-amino-3-methylbutyl)quinolin-6-yl)pyridin-2-yl)-4-(trifluoromethyl)benzamide

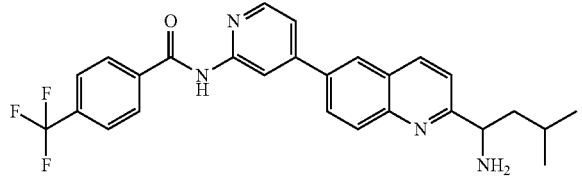 [SMILES: CC(C)CC(N)c1ccc2cc(-c3ccnc(NC(=O)c4ccc(C(F)(F)F)cc4)c3)ccc2n1]

Part A. N-(4-bromopyridin-2-yl)-4-(trifluoromethyl)benzamide

To a stirred solution of 4-(trifluoromethyl)benzoyl chloride (214 mg, 1.028 mmol) in DCM (4 mL) was added DIEA (0.748 mL, 4.29 mmol) and DMAP (20.94 mg, 0.171 mmol). The reaction mixture was cooled to 0° C. and treated with 4-bromopyridin-2-amine (150 mg, 0.87 mmol). The reaction mixture was allowed to stir for 12 h and quenched with water (3 mL). The organic layer was separated, washed with 10% NaHCO$_3$ solution (5 mL), water (3×5 mL) and brine (5 mL). The organic layer was dried over Na$_2$SO$_4$, filtered and concentrated under reduced pressure. The residue was purified by preparative silica gel TLC (40% ethyl acetate in hexanes) to afford N-(4-bromopyridin-2-yl)-4-(trifluoromethyl)benzamide (70 mg, 0.187 mmol, 22% yield). LCMS (ESI) m/e 345.0 [(M+H)$^+$, calcd for C$_{13}$H$_9$BrF$_3$N$_2$O, 345.0]; LC/MS retention time (method E): $t_R$=2.04 min.

Part B. N-(4-(2-(1-(1,1-dimethylethylsulfinamido)-3-methylbutyl)quinolin-6-yl)pyridin-2-yl)-4-(trifluoromethyl)benzamide A solution of 2-methyl-N-(3-methyl-1-(6-(trimethylstannyl)quinolin-2-yl)butyl)propane-2-sulfinamide (100 mg, 0.208 mmol) in DMF (3 mL) in a 10 mL pressure tube was treated with N-(4-bromopyridin-2-yl)-4-(trifluoromethyl)benzamide (86 mg, 0.249 mmol), tetrabutylammonium bromide (100 mg, 0.312 mmol) and K$_2$CO$_3$ (86 mg, 0.623 mmol). Nitrogen gas was bubbled through the stirred suspension for 10 min and charged with bis(triphenylphosphine)palladium(II) chloride (146 mg, 0.208 mmol). Again nitrogen gas was bubbled through the stirred suspension for 10 min and the reaction mixture was heated at 95° C. and stirred for 12 h. The reaction mixture was cooled to room temperature, diluted with water (10 mL) and then extracted with EtOAc (3×5 mL). The combined organic layers were washed with water (10 mL), then with brine (10 mL). The organic layer was dried over Na$_2$SO$_4$, filtered and concentrated under reduced pressure. The residue was purified by silica gel column chromatography using 0-18% ethyl acetate in hexane to afford N-(4-(2-(1-(1,1-dimethylethylsulfinamido)-3-methylbutyl)quinolin-6-yl)pyridin-2-yl)-4-(trifluoromethyl)benzamide (70 mg, 0.077 mmol, 37% yield). LCMS (ESI) m/e 583.2 [(M+H)$^+$, calcd for C$_{31}$H$_{34}$F$_3$N$_4$O$_2$S, 583.23]; LC/MS retention time (method E): $t_R$=2.40 min.

Part C. N-(4-(2-(1-amino-3-methylbutyl)quinolin-6-yl)pyridin-2-yl)-4-(trifluoromethyl)benzamide To a solution of N-(4-(2-(1-(1,1-dimethylethylsulfinamido)-3-methylbutyl)quinolin-6-yl)pyridin-2-yl)-4-(trifluoromethyl)benzamide (70 mg, 0.120 mmol) in ether (3 mL) at 0° C. was added 2M hydrogen chloride in diethyl ether (60 uL, 0.120 mmol) dropwise. The cooling bath was removed and the reaction mixture was to room temperature and stirred for 2 h. The volatiles were evaporated under reduced pressure. The residue was diluted with water (15 mL) and washed with ethyl acetate (10 mL). The aqueous layer was basified with 10% NaHCO$_3$ solution (20 mL) and extracted with ethyl acetate (3×10 mL). The combined organic layers were dried over Na$_2$SO$_4$, filtered and concentrated under reduced pressure. The residue was purified by preparative HPLC (0.1% TFA in water and acetonitrile) to afford N-(4-(2-(1-amino-3-methylbutyl)quinolin-6-yl)pyridin-2-yl)-4 (trifluoromethyl)benzamide, TFA (12 mg, 0.025 mmol, 20% yield) as a white solid. $^1$H NMR (400 MHz, CD$_3$OD) δ ppm 8.72 (s, 1H) 8.52-8.58 (m, 2H) 8.45 (d, J=1.6 Hz, 1H) 8.21-8.31 (m, 4H) 7.90 (d, J=8.0 Hz, 2H) 7.64-7.69 (m, 2H) 4.75 (t, J=7.2 Hz, 1H) 1.88-2.03 (m, 2H) 1.69-1.76 (m, 1H) 1.05-1.09 (m, 6H); LCMS (ESI) m/e 479.2 [(M+H)$^+$, calcd for C$_{27}$H$_{26}$F$_3$N$_4$O, 479.2]; LC/MS retention time (method A): $t_R$=1.87 min; HPLC retention time (method D): $t_R$=8.89 min; HPLC retention time (method C): $t_R$=7.85 min; Chiral HPLC (method A2): $t_R$=6.97 min.

Example 43

1-(4-ethyl-6-(pyridin-4-yl)quinolin-2-yl)-3-methylbutan-1-amine

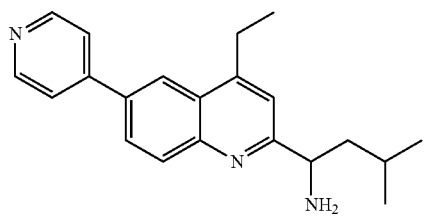 [SMILES: CCc1cc(C(N)CC(C)C)nc2ccc(-c3ccncc3)cc12]

Part A. 6-bromo-2-methylquinolin-4-ol

4-Bromoaniline (10 g, 58.1 mmol), PPA (14.30 mL, 58.1 mmol) and ethyl 3-oxobutanoate (15.13 g, 116 mmol) were heated to 170° C. for 12 h under a nitrogen atmosphere. The reaction was allowed to cool to room temperature and quenched with 20% NaOH solution so that pH=7. The precipitated solid was collected by vacuum filtration, washed with water (100 mL) and dried under vacuum. The solid was transferred to a flask and taken up in ethyl acetate (100 mL). The resultant mixture was stirred for 30 min to dissolve traces of 4-bromoaniline. The solid was again collected by vacuum filtration, washed with water (100 mL) and dried under vacuum overnight to afford 6-bromo-2-methylquinolin-4-ol (8.1 g, 32.1 mmol, 55% yield). LCMS (ESI) m/e 238.0 [(M+H)$^+$, calcd for $C_{10}H_9BrNO$, 238.0]; LC/MS retention time (method B): $t_R$=1.37 min.

Part B. 2-methyl-6-(pyridin-4-yl)quinolin-4-ol 6-bromo-2-methylquinolin-4-ol (2 g, 8.40 mmol), pyridin-4-ylboronic acid (1.239 g, 10.08 mmol) and sodium carbonate (1.157 g, 10.92 mmol) were taken up in a solvent mixture of toluene (50 mL) and EtOH (15 mL). The resultant mixture was purged with nitrogen for 5 min and Pd(PPh$_3$)$_4$ (0.971 g, 0.840 mmol) was added. The reaction mixture was then heated at 95° C. for 14 h. The reaction mixture was then cooled to room temperature and concentrated under reduced pressure. The residue was treated with water and the precipitated solid was collected by vacuum filtration, washed with water and dried under vacuum to give 2-methyl-6-(pyridin-4-yl)quinolin-4-ol (0.91 g, 3.27 mmol, 39% yield). LCMS (ESI) m/e 237.0 [(M+H)$^+$, calcd for $C_{15}H_{13}N_2O$, 237.1]; LC/MS retention time (method B): $t_R$=0.81 min.

Part C. 4-bromo-2-methyl-6-(pyridin-4-yl)quinoline

To a stirred solution of 2-methyl-6-(pyridin-4-yl)quinolin-4-ol (0.8 g, 3.39 mmol) in DMF (15 mL) was added PBr$_3$ (0.383 mL, 4.06 mmol) dropwise via syringe and the reaction was stirred at room temperature for 45 min. Ice water was added and the mixture was stirred at room temperature for 30 min. The pH of the reaction mixture was adjusted to 8 by addition of 10% NaOH solution. The mixture was transferred into a reparatory funnel containing saturated sodium bicarbonate (20 mL) and extracted with dichloromethane (2×25 mL). The organic layer was washed with brine (20 mL), dried over Na$_2$SO$_4$, filtered and concentrated under reduced pressure. The residue was purified by silica gel column chromatography (3% MeOH in DCM) to afford 4-bromo-2-methyl-6-(pyridin-4-yl)quinoline (0.85 g, 1.954 mmol, 58% yield). $^1$H NMR (400 MHz, DMSO-d$_6$) δ ppm 8.73 (d, J=6.0 Hz, 2H), 8.39 (d, J=2.0 Hz, 1H), 8.23 (dd, J=8.8, 2.0 Hz, 1H), 8.12 (d, J=8.8 Hz, 1H), 7.96 (m, 1H), 7.88 (dd, J=4.4, 1.6 Hz, 2H), 2.69 (s, 3H).

Part D.
4-bromo-6-(pyridin-4-yl)quinoline-2-carbaldehyde

Prepared in a similar fashion as described in Example 33, Part C using 4-bromo-2-methyl-6-(pyridin-4-yl)quinoline (0.8 g, 2.67 mmol) to afford 4-bromo-6-(pyridin-4-yl)quinoline-2-carbaldehyde (0.65 g, 1.827 mmol, 68% yield). LCMS (ESI) m/e 313.0 [(M+H)$^+$, calcd for $C_{15}H_{10}BrN_2O$, 313.0]; LC/MS retention time (method B): $t_R$=1.18 min. $^1$H NMR (400 MHz, DMSO-d$_6$) δ ppm 10.12 (s, 1H), 8.78 (m, 2H), 8.53 (m, 1H), 8.43 (s, 2H), 8.34 (s, 1H), 7.95 (m, 2H).

Part E. N-((4-bromo-6-(pyridin-4-yl)quinolin-2-yl)methylene)-2-methylpropane-2-sulfinamide Prepared in a similar fashion as described in Example 33, Part D using 4-bromo-6-(pyridin-4-yl)quinoline-2-carbaldehyde (0.65 g, 2.076 mmol) and 2-methylpropane-2-sulfinamide (0.252 g, 2.076 mmol) to afford N-((4-bromo-6-(pyridin-4-yl)quinolin-2-yl)methylene)-2-methylpropane-2-sulfinamide (0.45 g, 0.928 mmol, 45% yield). The crude product was taken into the next step without purification. LCMS (ESI) m/e 416.0 [(M+H)$^+$, calcd for $C_{19}H_{19}BrN_3OS$, 416.0]; LC/MS retention time (method A): $t_R$=2.21 min.

Part F. N-(1-(4-bromo-6-(pyridin-4-yl)quinolin-2-yl)-3-methylbutyl)-2-methylpropane-2-sulfinamide To a stirred solution of N-((4-bromo-6-(pyridin-4-yl)quinolin-2-yl)methylene)-2-methylpropane-2-sulfinamide (0.3 g, 0.721 mmol) in dry toluene (25 mL) at −45° C. was added isobutylmagnesium bromide, 2 M in diethyl ether (4.0 mL, 2.88 mmol) dropwise and the reaction was stirred at this temperature for 1 h. The reaction was allowed to warm to room temperature and carefully quenched with saturated ammonium chloride (10 mL). The solution was extracted with ethyl acetate (2×20 mL). The organic layer was washed with water (10 mL), dried over sodium sulfate and concentrated under reduced pressure. The crude product was purified by silica gel column chromatography (15% MeOH in DCM as an eluent) to afford N-(1-(4-bromo-6-(pyridin-4-yl)quinolin-2-yl)-3-methylbutyl)-2-methylpropane-2-sulfinamide (0.35 g, 0.634 mmol, 88% yield). LCMS (ESI) m/e 474.2 [(M+H)$^+$, calcd for $C_{23}H_{29}BrN_3OS$, 474.1]; LC/MS retention time (method A): $t_R$=2.12 min, 2.23 min (diastereomeric mixture).

Part G. 2-methyl-N-(3-methyl-1-(6-(pyridin-4-yl)-4-vinylquinolin-2-yl)butyl)propane-2-sulfinamide To a stirred solution of N-(1-(4-bromo-6-(pyridin-4-yl)quinolin-2-yl)-3-methylbutyl)-2-methylpropane-2-sulfinamide (0.2 g, 0.422 mmol) and tributylethenylstannane (0.148 mL, 0.506 mmol) in toluene (15 mL) was added Pd(PPh$_3$)$_4$ (0.024 g, 0.021 mmol) and the reaction mixture was purged with nitrogen for 5 min. The reaction mixture was then heated at 110° C. for 20 h. The reaction mixture was cooled to room temperature and diluted with EtOAc (20 mL) and water (20 mL). The organic layer was separated, washed with brine (20 mL), dried over Na$_2$SO$_4$ and concentrated under reduced pressure to afford 2-methyl-N-(3-methyl-1-(6-(pyridin-4-yl)-4-vinylquinolin-2-yl)butyl)propane-2-sulfinamide (90 mg, 0.160 mmol, 38% yield). LCMS (ESI) m/e 422.2 [(M+H)$^+$, calcd for $C_{25}H_{32}N_3OS$, 422.2]; LC/MS retention time (method A): $t_R$=1.94 min, 2.13 min (diastereomeric mixture).

Part H. N-(1-(4-ethyl-6-(pyridin-4-yl)quinolin-2-yl)-3-methylbutyl)-2-methylpropane-2-sulfinamide To a stirred solution of 2-methyl-N-(3-methyl-1-(6-(pyridin-4-yl)-4-vinylquinolin-2-yl)butyl)propane-2-sulfinamide (65 mg, 0.154 mmol) in MeOH (10 mL) was added palladium on carbon (12 mg, 0.113 mmol) and the reaction was stirred under 1 atm hydrogen pressure for 48 h. The reaction mixture was filtered through a diatomaceous earth (Celite®) pad and the pad was washed with MeOH. The solution was concentrated to afford N-(1-(4-ethyl-6-(pyridin-4-yl)quinolin-2-yl)-3-methylbutyl)-2-methylpropane-2-sulfinamide (65 mg, 0.112 mmol, 73% yield) which was taken to the next step without further purification. LCMS (ESI) m/e 424.2 [(M+H)$^+$, calcd for $C_{25}H_{34}N_3OS$, 424.2]; LC/MS retention time (method A): $t_R$=1.94 min, 2.13 min (diastereomeric mixture).

Part I. 1-(4-ethyl-6-(pyridin-4-yl)quinolin-2-yl)-3-methylbutan-1-amine

To a stirred solution of N-(1-(4-ethyl-6-(pyridin-4-yl)quinolin-2-yl)-3-methylbutyl)-2-methylpropane-2-sulfinamide (0.07 g, 0.165 mmol) in MeOH (5 mL) was added HCl in diethyl ether (2M) (5 mL) at room temperature and stirred for 4 h. The solvent was evaporated and the residue was purified by preparative HPLC (0.1% HCl in water and acetonitrile) yielding racemic 1-(4-ethyl-6-(pyridin-4-yl)quinolin-2-yl)-3-methylbutan-1-amine hydrochloride (11 mg, 0.030 mmol, 18% yield) as a yellow solid. $^1$H NMR (400 MHz, DMSO-$d_6$) δ ppm 8.67 (s, 1H), 8.29-8.50 (m, 5H), 8.20 (d, J=8.8 Hz, 1H), 7.62 (s, 1H), 4.64 (d, J=6.4 Hz, 1H), 3.28-3.34 (m, 2H), 1.81-1.85 (m, 2H), 1.59 (t, J=6.8 Hz, 1H), 1.39 (t, J=7.6 Hz, 3H), 0.91-0.96 (m, 6H); LCMS (ESI) m/e 320.2 [(M+H)$^+$, calcd for $C_{21}H_{26}N_3$, 320.2]; LC/MS retention time (method B): $t_R$=1.35 min; HPLC retention time (method A): $t_R$=8.85 min; HPLC retention time (method B): $t_R$=9.79 min.

Example 44

2-(1-amino-3-methylbutyl)-8-fluoro-6-(pyridin-4-yl)quinoline-4-carbonitrile

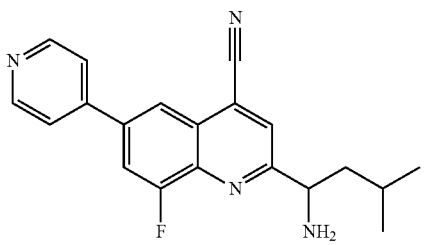 [SMILES: CC(C)CC(N)c1cc(C#N)c2cc(-c3ccncc3)cc(F)c2n1]

Part A. ethyl 3-(4-bromo-2-fluorophenylamino)-6-methylhept-2-enoate

To a solution of 4-bromo-2-fluoroaniline (9.22 g, 48.5 mmol) and ethyl 6-methyl-3-oxoheptanoate (9.037 g, 48.5 mmol) in toluene (200 mL) was added acetic acid (1.389 mL, 24.26 mmol) and 4 Å molecular sieves (9 g). The mixture was heated at 85° C. for 24 h. The mixture was cooled to room temperature and was concentrated. The crude product was purified by column chromatography on silica gel (10%-50% ethyl acetate in hexanes) to afford ethyl 3-((4-bromo-2-fluorophenyl)amino)-6-methylhept-2-enoate (9 g, 25.1 mmol, 52% yield) as a pale yellow oil. LCMS (ESI) m/e 358.00 [(M+H)$^+$, calcd for $C_{16}H_{22}BrFNO_2$, 358.07]; LC/MS retention time (method A): $t_R$=2.34 min, 2.63 min (E & Z isomers).

Part B.
6-bromo-8-fluoro-2-isopentylquinolin-4(1H)-one

A mixture of phenyl ether (40 mL) and ethyl 3-((4-bromo-2-fluorophenyl)amino)-6-methylhept-2-enoate (9 g, 25.1 mmol) in a 500 mL round bottom flask was heated at 250° C. for 1 h. The mixture was cooled to room temperature and transferred to a larger flask containing hexanes (200 mL) preheated to 40° C. The mixture was stirred for 30 min and then filtered. The filtrate was concentrated under reduced pressure to afford a residue which was purified by column chromatography on silica gel (0-30% ethyl acetate in petroleum ether) to afford 6-bromo-8-fluoro-2-isopentylquinolin-4(1H)-one (9.99 g, 20.47 mmol, 81% yield) as an oil. LCMS (ESI) m/e 312.0 [(M+H)$^+$, calcd for $C_{14}H_{16}BrFNO$, 312.0]; LC/MS retention time (method A): $t_R$=1.69 min.

Part C. 8-fluoro-2-isopentyl-6-(pyridin-4-yl)quinolin-4(1H)-one

Prepared in a similar fashion as described in Example 31, Part D using 6-bromo-8-fluoro-2-isopentylquinolin-4(1H)-one (0.660 g, 2.114 mmol) and 4-Pyridylboronic acid (0.390 g, 3.17 mmol) to afford 8-fluoro-2-isopentyl-6-(pyridin-4-yl)quinolin-4(1H)-one (0.370 g, 1.192 mmol, 56% yield) as a solid. LCMS (ESI) m/e 311.0 [(M+H)$^+$, calcd for $C_{19}H_{20}FN_2O$, 311.2]; LC/MS retention time (method A): $t_R$=1.51 min.

Part D. 4-bromo-8-fluoro-2-isopentyl-6-(pyridin-4-yl)quinoline

Prepared in a similar fashion as described in Example 37, Part A using 8-fluoro-2-isopentyl-6-(pyridin-4-yl)quinolin-4(1H)-one (1.162 g, 3.74 mmol). The residue was purified by preparative TLC on silica gel (2% methanol in $CH_2Cl_2$ mobile phase) to afford 4-bromo-8-fluoro-2-isopentyl-6-(pyridin-4-yl)quinoline (0.441 g, 1.181 mmol, 32% yield) as an orange oil. LCMS (ESI) m/e 373.0 [(M+H)$^+$, calcd for $C_{19}H_{19}BrFN_2$, 373.1]; LC/MS retention time (method E): $t_R$=2.32 min.

Part E. 8-fluoro-2-isopentyl-6-(pyridin-4-yl)quinoline-4-carbonitrile

Prepared in a similar fashion as described in Example 37, Part F using 4-bromo-8-fluoro-2-isopentyl-6-(pyridin-4-yl)quinoline (0.441 g, 1.181 mmol). The crude product was purified by preparative TLC on silica gel (3% methanol in $CH_2Cl_2$) to afford 8-fluoro-2-isopentyl-6-(pyridin-4-yl)quinoline-4-carbonitrile (0.179 g, 0.560 mmol, 47% yield) as a solid. LCMS (ESI) m/e 320.2 [(M+H)$^+$, calcd for $C_{20}H_{19}FN_3$, 320.2]; LC/MS retention time (method E): $t_R$=2.12 min.

Part F. 2-(1-bromo-3-methylbutyl)-8-fluoro-6-(pyridin-4-yl)quinoline-4-carbonitrile Prepared in a similar fashion as described in Example 37, Part B using 8-fluoro-2-isopentyl-6-(pyridin-4-yl)quinoline-4-carbonitrile (0.179 g, 0.560 mmol). The crude product was purified by preparative TLC (2% methanol in $CH_2Cl_2$ mobile phase) to afford 2-(1-bromo-3-methylbutyl)-8-fluoro-6-(pyridin-4-yl)quinoline-4-carbonitrile (0.082 g, 0.206 mmol, 37% yield) as an oil. LCMS (ESI) m/e 398.2 [(M+H)$^+$, calcd for $C_{20}H_{18}BrFN_3$, 398.1]; LC/MS retention time (method E): $t_R$=2.20 min.

Part G. 2-(1-azido-3-methylbutyl)-8-fluoro-6-(pyridin-4-yl)quinoline-4-carbonitrile Prepared in a similar fashion as described in Example 37, Part C using 2-(1-bromo-3-methylbutyl)-8-fluoro-6-(pyridin-4-yl)quinoline-4-carbonitrile (0.082 g, 0.206 mmol) to afford 2-(1-azido-3-methylbutyl)-8-fluoro-6-(pyridin-4-yl)quinoline-4-carbonitrile (0.093 g, 0.145 mmol, 70% yield). The crude product was taken to next step without purification. LCMS (ESI) m/e 361.5 [(M+H)+, calcd for $C_{20}H_{18}FN_6$, 361.2]; LC/MS retention time (method D): $t_R$=0.88 min.

Part H. 2-(1-amino-3-methylbutyl)-8-fluoro-6-(pyridin-4-yl)quinoline-4-carbonitrile Prepared in a similar fashion as described in Example 37, Part D using 2-(1-azido-3-methylbutyl)-8-fluoro-6-(pyridin-4-yl)quinoline-4-carbonitrile (0.093 g, 0.258 mmol). The crude product was purified by preparative HPLC (10 mM ammonium acetate in water and acetonitrile) to afford 2-(1-amino-3-methylbutyl)-8-fluoro-6-(pyridin-4-yl)quinoline-4-carbonitrile (6 mg, 0.018 mmol, 7% yield) as a pale brown solid. $^1$H NMR (400 MHz, CD$_3$OD) δ ppm 8.73-8.74 (m, 2H) 8.32-8.33 (m, 1H) 8.23 (s, 1H) 8.13-8.16 (m, 1H) 7.93-7.94 (m, 2H) 4.45-4.49 (m, 1H) 1.67-1.84 (m, 3H) 1.01-1.05 (m, 6H); LCMS (ESI) m/e 335.2 [(M+H)+, calcd for $C_{20}H_{20}FN_4$, 335.2]; LC/MS retention time (method A): $t_R$=1.58 min; HPLC retention time (method E): $t_R$=8.71 min; HPLC retention time (method F): $t_R$=9.24 min.

Example 45

N-(4-(2-(1-hydroxy-3-methylbutyl)quinolin-6-yl)pyridin-2-yl)acetamide

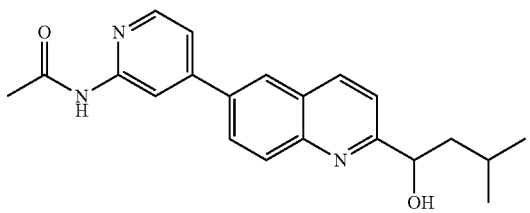 [SMILES: CC(=O)Nc1cc(-c2ccc3nc(C(O)CC(C)C)ccc3c2)ccn1]

Part A.
1-(6-bromoquinolin-2-yl)-3-methylbutan-1-ol

To a stirred solution of 6-bromoquinoline-2-carbaldehyde (prepared as described in Example 25, Part A) (1 g, 4.24 mmol) in anhydrous toluene (20 mL) at −40° C. was added isobutylmagnesium bromide, 2M in diethyl ether (4.23 mL, 8.47 mmol) dropwise. The mixture was then stirred for 3 h at −40° C. The reaction mixture was quenched with aqueous ammonium chloride (10 mL) and extracted with ethyl acetate (2×25 mL). The combined organic layers were dried over Na$_2$SO$_4$ and evaporated under reduced pressure. The crude product was purified by column chromatography to afford 1-(6-bromoquinolin-2-yl)-3-methylbutan-1-ol (300 mg, 1.04 mmol, 24% yield). LCMS (ESI) m/e 294.0 [(M+H)+, calcd for $C_{14}H_{17}BrNO$, 294.1]; LC/MS retention time (method A): $t_R$=2.08 min.

Part B. 3-methyl-1-(6-(trimethylstannyl)quinolin-2-yl)butan-1-ol

Preparation as described in Example 25, Part D using 1-(6-bromonaphthalen-2-yl)-3-methylbutan-1-ol (0.2 g, 0.682 mmol) to afford 3-methyl-1-(6-(trimethylstannyl)quinolin-2-yl)butan-1-ol (160 mg, 0.424 mmol, 62% yield). LCMS (ESI) m/e 380.2 [(M+H)+, calcd for $C_{17}H_{26}NOSn$, 380.1]; LC/MS retention time (method A): $t_R$=2.49 min.

Part C. N-(4-(2-(1-hydroxy-3-methylbutyl)quinolin-6-yl)pyridin-2-yl)acetamide

To the stirred solution of 3-methyl-1-(6-(trimethylstannyl)naphthalen-2-yl)butan-1-ol (0.080 g, 0.212 mmol) and (4-bromopyridin-2-yl)acetamide (0.046 g, 0.212 mmol) in anhydrous DMF (2 mL) was added tetrabutylammonium bromide (0.103 g, 0.318 mmol), bis(triphenylphosphine)palladium (II) chloride (0.019 g, 0.021 mmol), K$_2$CO$_3$ (0.088 g, 0.636 mmol) and the mixture purged with nitrogen for 5 min then heated at 95° C. for 14 h. The reaction mixture was diluted with water and extracted with ethyl acetate. The combined organic layers were dried over Na$_2$SO$_4$ and evaporated under reduced pressure. The residue was purified by preparative HPLC (0.1% TFA in water and acetonitrile) to afford N-(4-(2-(1-hydroxy-3-methylbutyl)quinolin-6-yl)pyridin-2-yl)acetamide, TFA (9 mg, 0.026 mmol, 12% yield). $^1$H NMR (400 MHz, CD$_3$OD) δ ppm 8.98 (d, J=8.8 Hz, 1H) 8.65 (d, J=1.6 Hz, 1H) 8.40-8.49 (m, 3H) 8.30 (s, 1H) 8.04 (d, J=8.8 Hz, 1H) 7.77-7.79 (m, 1H) 5.21-5.24 (m, 1H) 2.31 (s, 3H) 2.01-2.04 (m, 1H) 1.80-1.87 (m, 1H) 1.69-1.75 (m, 1H) 1.00-1.12 (m, 6H); LCMS (ESI) m/e 350.2 [(M+H)+, calcd for $C_{21}H_{24}N_3O_2$, 350.2]; LC/MS retention time (method A): $t_R$=1.62 min; HPLC retention time (method A): $t_R$=11.25 min.

Example 46

N-(2'-(1-amino-3-methylbutyl)-4,6'-biquinolin-2-yl)acetamide

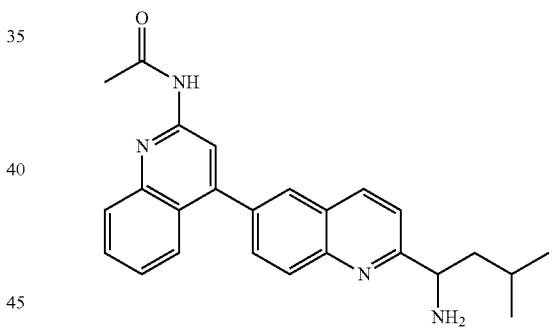

Part A. 2-aminoquinolin-4-ol

To a stirring solution of aniline (1 g, 10.74 mmol) in ethyl acetate (20 mL) was added 4-methylbenzenesulfinic acid (1.677 g, 10.74 mmol) at room temperature. The mixture was stirred for 10 min during which time a white solid formed. The solid was collected by vacuum filtration and dried under high vacuum to remove volatiles. The solid was then heated at 260° C. for 5 min and treated with ethyl 2-cyanoacetate (0.607 g, 5.37 mmol) dropwise at the same temperature. Heating at 260° C. was continued for another 90 min during which time the reaction mixture turned orange. The reaction mixture was then cooled to room temperature and treated with CHCl$_3$ (20 mL). The resultant mixture was refluxed at 50° C. for 12 h to dissolve any residue. Water (30 mL), ethanol (10 mL), saturated Na$_2$CO$_3$ (30 mL) solution were added in sequence and the reaction mixture was vigorously stirred for 1 h. The solid obtained was collected by vacuum filtration and dried under reduced pressure to afford 2-aminoquinolin-4-ol (1 g, 5.49 mmol, 51% yield). LCMS (ESI) m/e 159.2 [(M−H)⁻, calcd for C₉H₇N₂O, 159.1]; LC/MS retention time (method E): $t_R$=0.89 min.

Part B. 4-bromoquinolin-2-amine

2-Aminoquinolin-4-ol (0.7 g, 4.37 mmol) was taken up in a pressure tube and treated with phosphorous oxybromide (2.51 g, 8.74 mmol) and phosphorous tribromide (3 mL, 31.8 mmol). The tube was capped under $N_2$ and heated at 150° C. for 19 h. The reaction mixture was then cooled to room temperature and basified using aq. NaOH (2 M, 10 mL) and extracted with ethyl acetate (3×25 mL). The combined organic layers were washed with water (20 mL), dried over $Na_2SO_4$ and evaporated under reduced pressure. The solid obtained was washed with hexane (20 mL) to remove any nonpolar impurity and dried under reduced pressure to afford a dark brown residue which was purified by column chromatography on silica (using a gradient of methanol and chloroform) to afford 4-bromoquinolin-2-amine (160 mg, 0.71 mmol, 16% yield). LCMS (ESI) m/e 223.0 (bromo pattern observed) [(M+H)⁺, calcd for $C_9H_8BrN_2$, 223.0]; LC/MS retention time (method B): $t_R$=1.14 min.

Part C. N-(4-bromoquinolin-2-yl)acetamide

To a solution of 4-bromoquinolin-2-amine (400 mg, 1.793 mmol) in DCM (4 mL) cooled to 0° C. was added acetyl chloride (211 mg, 2.69 mmol) dropwise. Then the reaction mixture was allowed to stir at room temperature for 1 h. The reaction was quenched with water (10 mL) and extracted with ethyl acetate (5×3 mL). The combined organic layers were washed with 10% $NaHCO_3$ (10 mL), followed by brine (10 mL), dried over $Na_2SO_4$, filtered and concentrated under reduced pressure to afford N-(4-bromoquinolin-2-yl)acetamide (550 mg, 1.556 mmol, 87% yield) as an oil. LCMS (ESI) m/e 265.0 [(M+H)⁺, calcd for $C_{11}H_{10}BrN_2O$, 265.0]; LC/MS retention time (method A): $t_R$=1.70 min.

Part D. N-(2'-(1-(1,1-dimethylethylsulfinamido)-3-methylbutyl)-4,6'-biquinolin-2-yl)acetamide The diastereomeric mixture was resolved by neutral alumina column chromatography using a gradient of ethyl acetate and pet ether as mobile phase (ethyl acetate and pet ether 8:92 to 10:90 ratio). The resolved diastereomers were further enriched by prep HPLC (10 mM ammonium acetate in water and acetonitrile) to afford two diastereomers: Isomer 1: 2-methyl-N-(3-methyl-1-(6-(trimethylstannyl)quinolin-2-yl)butyl)propane-2-sulfinamide and Isomer 2: 2-methyl-N-(3-methyl-1-(6-(trimethylstannyl)quinolin-2-yl)butyl)propane-2-sulfinamide. The absolute stereochemistry of the isomers was not determined.

Part E. N-(2'-(1-(1,1-dimethylethylsulfinamido)-3-methylbutyl)-4,6'-biquinolin-2-yl)acetamide To a stirring solution of 2-methyl-N-(3-methyl-1-(6-(trimethylstannyl)quinolin-2-yl)butyl)propane-2-sulfinamide (Isomer-1) (100 mg, 0.208 mmol) in DMF (4 mL), $K_2CO_3$ (86 mg, 0.623 mmol), tetrabutylammonium bromide (100 mg, 0.312 mmol) and N-(4-bromoquinolin-2-yl)acetamide (66.1 mg, 0.249 mmol) were added. Nitrogen gas was bubbled through the suspension for 5 min. Bis(triphenylphosphine)palladium(II) chloride (14.58 mg, 0.021 mmol) was added and nitrogen gas was bubbled through the solution for another 10 min. The reaction mixture was then heated at 95° C. and stirred for 12 h. The reaction mixture was cooled to room temperature and diluted with water (3 mL) then extracted with ethyl acetate (3×4 mL). The organic layer was separated and washed with water (10 mL) followed by brine (5 mL), dried over $Na_2SO_4$ and concentrated under reduced pressure to afford optically pure N-(2'-(1-(1,1-dimethylethylsulfinamido)-3-methylbutyl)-[4,6'-biquinolin]-2-yl)acetamide (95 mg, 0.068 mmol, 33% yield) as an oil. The crude product was taken for next step without purification. LCMS (ESI) m/e 503.2 [(M+H)⁺, calcd for $C_{29}H_{35}N_4O_2S$, 503.24]; LC/MS retention time (method E): $t_R$=2.08 min. The absolute stereochemistry was not determined.

Part F. N-(2'-(1-amino-3-methylbutyl)-4,6'-biquinolin-2-yl)acetamide

Prepared as described in Example 25, Part F from optically pure N-(2'-(1-(1,1-dimethylethylsulfinamido)-3-methylbutyl)-[4,6'-biquinolin]-2-yl)acetamide (70 mg, 0.139 mmol). The crude product was purified by preparative HPLC (0.1% TFA in water and acetonitrile) to afford N-(2'-(1-amino-3-methylbutyl)-[4,6'-biquinolin]-2-yl)acetamide, TFA (15 mg, 0.034 mmol, 24% yield) as a yellow solid. ¹H NMR (400 MHz, CD₃OD) δ ppm 8.50-8.55 (m, 1H), 8.30-8.33 (m, 2H), 8.20 (d, J=1.6 Hz, 1H), 8.00 (dd, J=8.4, 1.6 Hz, 2H), 7.85 (d, J=8.4 Hz, 1H), 7.76-7.80 (m, 1H), 7.67 (d, J=8.4 Hz, 1H), 7.49-7.53 (m, 1H), 4.74-4.78 (m, 1H), 2.29 (s, 3H), 1.93-2.04 (m, 2H), 1.72-1.75 (m, 1H), 1.06-1.10 (m, 6H); LCMS (ESI) m/e 399.2 [(M+H)⁺, calcd for $C_{25}H_{27}N_4O$, 399.2]; LC/MS retention time (method E): $t_R$=1.70 min; HPLC retention time (method D): $t_R$=6.60 min; HPLC retention time (method C): $t_R$=5.80 min; Chiral HPLC (method C1): $t_R$=8.34 min. The absolute stereochemistry was not determined.

Example 47

N-(2'-(1-amino-3-methylbutyl)-4,6'-biquinolin-2-yl)acetamide

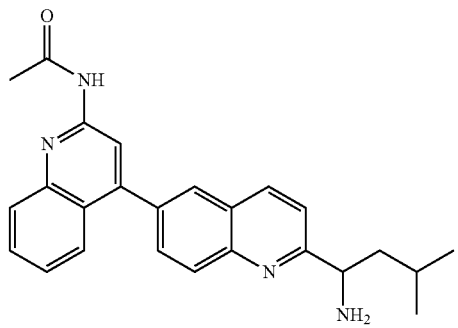 [SMILES: CC(=O)Nc1cc(-c2ccc3nc(C(N)CC(C)C)ccc3c2)c2ccccc2n1]

Prepared in a similar fashion as described in Example 46, Parts D-F using 2-methyl-N-(3-methyl-1-(6-(trimethylstannyl)quinolin-2-yl)butyl)propane-2-sulfinamide (Isomer-2) (100 mg, 0.208 mmol). The crude product was purified by preparative HPLC (0.1% TFA in water and acetonitrile) to afford optically pure N-(2'-(1-amino-3-methylbutyl)-[4,6'-biquinolin]-2-yl)acetamide, TFA (12 mg, 0.028 mmol, 9% yield for two steps) as a yellow solid. ¹H NMR (400 MHz, CD$_3$OD) δ ppm 8.50-8.60 (m, 1H), 8.30-8.35 (m, 1H), 8.21-8.26 (m, 2H), 8.00-8.04 (m, 2H), 7.87 (d, J=8.4 Hz, 1H), 7.78-7.83 (m, 1H), 7.68 (d, J=8.8 Hz, 1H), 7.51-7.55 (m, 1H), 4.76-4.79 (m, 1H), 2.31 (s, 3H), 1.92-2.04 (m, 2H), 1.72-1.76 (m, 1H), 1.06-1.10 (m, 6H); LCMS (ESI) m/e 399.2 [(M+H)$^+$, calcd for C$_{25}$H$_{27}$N$_4$O, 399.2]; LC/MS retention time (method E): $t_R$=1.69 min; HPLC retention time (method D): $t_R$=6.66 min; HPLC retention time (method C): $t_R$=5.60 min; Chiral HPLC (method B2): $t_R$=6.71 min. The absolute stereochemistry was not determined.

Example 48

2'-(1-amino-3-methylbutyl)-4,6'-biquinolin-2-amine

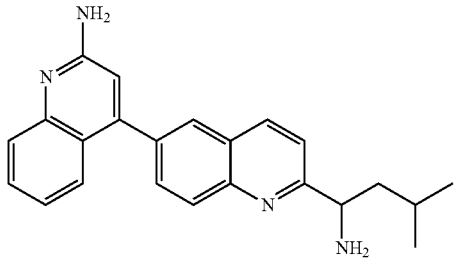

Prepared in a similar fashion as described in Example 46, carrying forward the first eluting isomer from step C to afford optically pure 2'-(1-amino-3-methylbutyl)-[4,6'-biquinolin]-2-amine, TFA (15 mg, 0.042 mmol, 29% yield for the final step) as a colorless solid. $^1$H NMR (400 MHz, CD$_3$OD) δ ppm 8.54-8.57 (m, 1H), 8.35 (d, J=8.8 Hz, 1H), 8.24 (d, J=1.6 Hz, 1H), 7.98 (dd, J=8.4, 2.0 Hz, 1H), 7.80-7.89 (m, 1H), 7.75-7.78 (m, 2H), 7.69-7.72 (m, 1H), 7.50-7.54 (m, 1H), 7.13 (s, 1H), 4.78 (t, J=7.2 Hz, 1H), 1.91-2.01 (m, 2H), 1.70-1.74 (m, 1H), 1.05-1.09 (m, 6H); LCMS (ESI) m/e 357.2 [(M+H)$^+$, calcd for C$_{23}$H$_{25}$N$_4$, 357.20]; LC/MS retention time (method E): $t_R$=1.66 min; HPLC retention time (method D): $t_R$=5.79 min; HPLC retention time (method A): $t_R$=9.91 min; Chiral HPLC (method D1): $t_R$=10.85 min. The absolute stereochemistry was not determined.

Example 49

2'-(1-amino-3-methylbutyl)-4,6'-biquinolin-2-amine

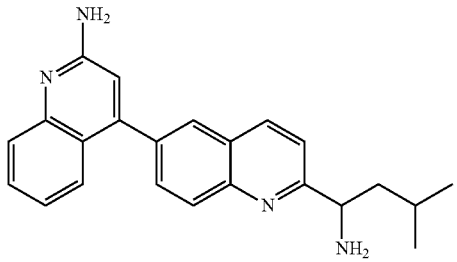 [SMILES: CC(C)CC(N)c1ccc2cc(-c3cc(N)nc4ccccc34)ccc2n1]

Prepared in a similar fashion as described in Example 46, carrying forward the second eluting isomer from step C to afford optically pure to afford 2'-(1-amino-3-methylbutyl)-[4,6'-biquinolin]-2-amine, TFA (15 mg, 0.040 mmol, 15% yield for the final step) as a colorless solid. $^1$H NMR (400 MHz, CD$_3$OD) δ ppm 8.55-8.60 (m, 1H) 8.36 (d, J=8.8 Hz, 1H) 8.25 (d, J=2.0 Hz, 1H) 7.99 (dd, J=8.4, 2.0 Hz, 1H) 7.85-7.90 (m, 1H) 7.70-7.80 (m, 3H) 7.51-7.55 (m, 1H) 7.13 (s, 1H) 4.77-4.81 (m, 1H) 1.90-2.03 (m, 2H) 1.69-1.76 (m, 1H) 1.05-1.10 (m, 6H); LCMS (ESI) m/e 357.2 [(M+H)$^+$, calcd for C$_{23}$H$_{25}$N$_4$, 357.20]; LC/MS retention time (method H): $t_R$=1.64 min; HPLC retention time (method A): $t_R$=9.61 min; HPLC retention time (method B): $t_R$=11.28 min; Chiral HPLC (method B1): $t_R$=8.26 min.

Example 50

1-(6-(2-cyclopropylpyridin-4-yl)quinolin-2-yl)-3-methylbutan-1-amine

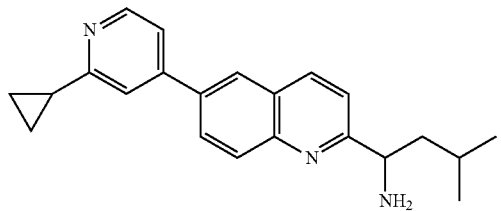 [SMILES: CC(C)CC(N)c1ccc2cc(-c3ccnc(C4CC4)c3)ccc2n1]

Part A. 4-bromo-2-cyclopropylpyridine

To a solution of 2,4-dibromopyridine (0.500 g, 2.111 mmol) in tetrahydrofuran (5 mL) was added tetrakis(triphenylphosphine)palladium(0) (0.073 g, 0.063 mmol). The reaction mixture was cooled to 0° C., then cyclopropylzinc bromide, 0.5M in THF (12.66 mL, 6.33 mmol) was added dropwise over 10 min. The reaction mixture was stirred at 20° C. for 16 h. The reaction mixture was quenched with of 10% NaHCO$_3$ solution (50 mL) and extracted with ethyl acetate (3×50 mL). The combined organic layers were washed with brine (50 mL), dried over Na$_2$SO$_4$, filtered and concentrated under reduced pressure to afford crude which was purified by column chromatography (mobile phase—ethyl acetate:petroleum ether) to afford 4-bromo-2-cyclopropylpyridine (100 mg, 0.51 mmol, 24% yield). $^1$H NMR (400 MHz, CDCl$_3$) δ ppm 8.17 (d, J=5.2 Hz, 1H), 7.15 (d, J=1.6 Hz, 1H), 6.89 (dd, J=5.2, 1.6 Hz, 1H), 1.81-1.85 (m, 1H), 1.10-1.15 (m, 2H), 0.75-0.85 (m, 2H).

Part B. N-(1-(6-(2-cyclopropylpyridin-4-yl)quinolin-2-yl)-3-methylbutyl)-2-methylpropane-2-sulfinamide To a solution of 4-bromo-2-cyclopropylpyridine (100 mg, 0.505 mmol) in DMF (4 mL) was added 2-methyl-N-(3-methyl-1-(6-(trimethylstannyl)quinolin-2-yl)butyl)propane-2-sulfinamide (219 mg, 0.454 mmol). Tetrabutyl ammonium bromide (244 mg, 0.757 mmol) and potassium carbonate (209 mg, 1.515 mmol) were added and nitrogen gas was bubbled through the solution for 5 min. Bis(triphenylphosphine)palladium (II) chloride (35.4 mg, 0.050 mmol) was added and nitrogen gas was bubbled through the solution for 5 min. The reaction mixture was then heated at 95° C. for 16 h. The reaction mixture was cooled to room temperature and diluted with water. The aqueous layer was extracted with ethyl acetate (3×50 mL). The combined organic layers were washed with brine (50 mL), dried over Na$_2$SO$_4$, filtered and concentrated to afford N-(1-(6-(2-cyclopropylpyridin-4-yl)

quinolin-2-yl)-3-methylbutyl)-2-methylpropane-2-sulfinamide (80 mg, 0.18 mmol, 40% yield). The crude product was taken to next step without purification. LCMS (ESI) m/e 436.2 [(M+H)$^+$, calcd for $C_{26}H_{34}N_3OS$, 436.23]; LC/MS retention time (method A): $t_R$=2.23 min.

Part C. 1-(6-(2-cyclopropylpyridin-4-yl)quinolin-2-yl)-3-methylbutan-1-amine

To a solution of N-(1-(6-(2-cyclopropylpyridin-4-yl)quinolin-2-yl)-3-methylbutyl)-2-methylpropane-2-sulfinamide (80 mg, 0.184 mmol) in dichloromethane (2 mL) cooled to 0° C. was added 4M HCl in dioxane (2 mL, 8.00 mmol) dropwise. The reaction mixture was stirred at 0° C. for 5 min. then allowed to warm to room temperature and stirred for 2 h. The reaction mixture was concentrated under reduced pressure. To the residue was added water (5 mL). The aqueous layer was washed with ethyl acetate (3×15 mL). To the aqueous layer was concentrated under reduced pressure. The crude product was purified by preparative HPLC (0.1% TFA in water and acetonitrile) to afford 1-(6-(2-cyclopropylpyridin-4-yl)quinolin-2-yl)-3-methylbutan-1-amine, TFA (10 mg, 0.029 mmol, 16% yield) as an off-white solid. $^1$H NMR (400 MHz, CD$_3$OD) δ ppm 8.56-8.59 (m, 3H), 8.33-8.34 (m, 2H), 8.03 (d, J=1.2 Hz, 1H), 7.69 (d, J=8.8 Hz, 1H), 7.49 (d, J=6.0, 1.6 Hz, 1H), 4.76 (t, J=7.6 Hz, 1H), 2.27-2.32 (m, 1H), 1.89-2.00 (m, 2H), 1.69-1.73 (m, 1H), 1.40-1.45 (m, 2H), 1.16-1.21 (m, 2H), 0.04-0.08 (m, 6H); LCMS (ESI) m/e 332.2 [(M+H)$^+$, calcd for $C_{22}H_{26}N_3$, 332.20]; LC/MS retention time (method A): $t_R$=1.64 min; HPLC retention time (method C): $t_R$=4.74 min; HPLC retention time (method D): $t_R$=5.84 min.

Methods

AAK1 Kinase Assay

The assays were performed in U-bottom 384-well plates. The final assay volume was 30 µl prepared from 15 µl additions of enzyme and substrates (fluoresceinated peptide (5-FAM)-Aha-KEEQSQITSQVTGQIGWR-NH2 and ATP) and test compounds in assay buffer (10 mM Tris-HCL pH 7.4, 10 mM MgCl$_2$, 0.01% Tween-20 and 1.0 mM DTT). The reactions were initiated by the combination of bacterially expressed, GST-Xa-hAAK1 with substrates and test compounds. The reactions were incubated at room temperature for 3 hours and terminated by adding 60 µl of 35 mM EDTA buffer to each sample. The reactions were analyzed on the Caliper LabChip 3000 (Caliper, Hopkinton, Mass.) by electrophoretic separation of the fluorescent substrate and phosphorylated product. Inhibition data were calculated by comparison to EDTA quenched control reactions for 100% inhibition and vehicle-only reactions for 0% inhibition. The final concentration of reagents in the assays are ATP, 22 µM; (5-FAM)-Aha-KEEQSQITSQVTGQIGWR-NH2, 1.5 µM; GST-Xa-hAAK1, 3.5 nM; and DMSO, 1.6%. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

HEK281 Cell-Based Assay

HEK293F cells were cultured in media containing DMEM (Gibco, cat. #11965), 10% FBS (SAFC Biosciences, cat.#12103C), 1×GPS (glutamine, penicillin and streptomycin). On day one, cells were plated on a 10 cm dish so that they are ~80% confluent at time of transfection. Roughly 12 million cells were in a 10 cm dish at time of transfection. On day two, each dish was transfected with 48 ug DNA and 144 ul Lipofectamine 2000 (Invitrogen, cat.#11668-019). The DNA was comprised of a mixture (per 10 cm dish) containing 3 ug AAK1/HA/pIRES (full length human, NCBI accession no. NP_055726.2), 45 µg Flag/AP2MI/pcDNA (full length human), and 1.5 ml OPTI-MEM. The Lipofectamine 2000 is made up of a mixture (per 10 cm dish) containing 144 µl Lipofectamine 2000 and 1.5 ml OPTI-MEM. Each mixture was transferred to individual 15 ml tubes and incubated at RT for 5 minutes, and then the two mixes were combined and incubated at RT for 20 minutes. Growth media was then aspirated from each 10 cm plate and replaced with 10 ml of DMEM+10% FBS (no GPS). Finally, 3 ml DNA/Lipofectamine mix was added to each 10 cm dish and mix gently followed by incubate of plate overnight at 37° C. and 5% CO$_2$.

On day three, compounds were diluted in 100% DMSO at 1000× final concentration, followed by 3-fold serial dilutions for a total of 5 concentrations tested. Four compounds were tested per 10 cm dish. One ul of each compound dilution was then pipetted into a deep-well, 96-well plate, followed by addition of 500 µl DMEM+0.5% FBS into each well for a 2× final concentration of each compound. Cells were resuspended in a 10 cm dish by simple pipetting (HEK293 cells come off the plate that easy at this point) and then transferred to a 50 ml conical tube and pelleted by centrifugation at 1000 rpm for 5 min. Cell pellets were then resuspended in 2.75 ml DMEM+0.5% FBS per 10 cm dish and 100 µl of cell suspension transferred into each well of 96-well TC plate. Finally, 100 µl of 2× compound diluted in DMEM+0.5% FBS was then added into wells containing cell suspension for a 1× final concentration. Plates were then incubated at 37° C. and 5% CO$_2$ for 3 hours followed by transferring of cell suspensions from each well into 12-tube PCR strips. The PCR strips were spun in a tip rack at 1000 rpm for 5 minutes to pellet cells and media was then removed by pipetting without disturbing the cell pellet.

To prepare for Western Blot analysis, cell pellets were resuspend in 40 ul 1×LDS-PAGE sample buffer (Invitrogen, cat.# NP0008)+2× Halt phophatase and protease inhibitor cocktail (Thermo Scientific, cat.#1861284), followed by sonicating each with microtip sonicator set at 5 for 8-10 seconds. Five ul of 10× NuPage Sample Reducing Agent (with 50 mM DTT) was to each sample followed by heat denaturing at 70 C for 10 min on PCR machine. A total of 10 µl per sample was loaded into each lane of a 4-20% Tris-Glycine Criterion 26-well gel (Biorad, cat.#345-0034) for the phospho-mu2 blot and 10 µl per lane in a 4-12% Bis-Tris (+MES buffer) NuPAGE 26-well gel (Invitrogen, cat.# WG1403BX10) for the mu2 blot. For controls, 2 ng of phospho-mu2 or 20 ng mu2/Flag proteins were loaded in the last well of each gel. After SDS-PAGE, samples on each gel were transferred to PVDF membrane using an iBlot and membranes were blocked for one hour in TBST+5% milk, followed by wash 3× for 5-10 min with TBST. Criterion gels were probed with rabbit anti-phospho-mu2 (1:5000; a rabbit polyclonal antibody produced by New England Peptide and affinity purified at Lexicon) in TBST+5% BSA, whereas, NuPAGE gels were probed with mouse anti-Flag (1:500; Sigma, cat.# F1804) in TBST+5% milk, and these primary antibodies were incubated overnight at 4° C. on a rocker.

On day four, Western blots were washed 3× for 5-10 minutes with TBST, probe with anti-rabbit-HRP (1:2000; BioRad, cat.#170-6515) or anti-mouse-HRP (1:2000; Biorad, cat.#170-6516) in TBST+5% milk for 1 hour at RT, washed 3× for 10 minutes with TBST, and developed with ECL reagent (GE Healthcare, cat.# RPN2132) on a Versadoc. Finally, the camera was set up to take a picture every 30 seconds for 10 minutes and the best image saved for each blot with no saturated signal (when the signal is saturated, the bands will be highlighted red). A volume analysis on each band was performed to obtain density values. Percent inhibition was calculated for each sample by first normalizing to total Mu2 expression levels and then comparing to 0% and 100% controls. IC$_{50}$ values were then calculated using Excel fitting software. Functional potency for select compounds are listed in Table 2 as 1050 ranges wherein a —=1-10 nM; b=11-100 nM; and c=101-2500 nM.

| Example | IC$_{50}$ (nM) |
|---|---|
| 1 | b |
| 2 | c |
| 3 | b |
| 4 | c |
| 5 | b |
| 6 | b |
| 7 | 12 |
| 8 | a |
| 9 | b |
| 10 | b |
| 11 | b |
| 12 | b |
| 13 | 4.1 |
| 14 | c |
| 15 | c |
| 16 | b |
| 17 | c |
| 18 | c |
| 19 | c |
| 20 | b |
| 21 | b |
| 22 | c |
| 23 | c |
| 24 | c |
| 25 | a |
| 26 | b |
| 27 | c |
| 28 | b |
| 29 | a |
| 30 | c |
| 31 | b |
| 32 | c |
| 33 | a |
| 34 | a |
| 35 | b |
| 36 | a |
| 37 | a |
| 38 | b |
| 39 | 54 |
| 40 | c |
| 41 | c |
| 42 | b |
| 43 | b |
| 44 | b |
| 45 | b |
| 46 | c |
| 47 | 1200 |
| 48 | c |
| 49 | c |
| 50 | c |

The invention claimed is:
1. A compound of formula (I)

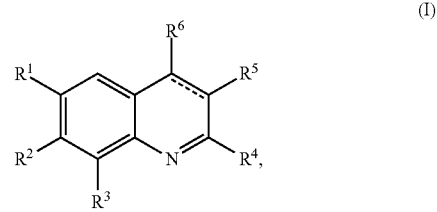

or a pharmaceutically acceptable salt thereof, wherein:
R$^1$ is selected from imidazopyridazine, isoquinolinyl, oxazolyl, pyridinyl, pyrimidinyl, pyrrolopyridinyl, and quinolinyl, wherein each ring is optionally substituted with one group selected from C$_1$-C$_3$acylamino, C$_1$-C$_3$alkyl, amino, C$_1$-C$_3$alkoxy, C$_3$-C$_6$cycloalkyl, C$_3$-C$_6$cycloalkylamino, C$_1$-C$_3$dialkylamino, —NHCO$_2$(C$_1$-C$_3$)alkyl, and phenylcarbonylamino optionally substituted with a halo or haloalkyl group;
R$^2$ is selected from hydrogen, C$_1$-C$_3$alkoxy, and C$_1$-C$_3$alkyl;
R$^3$ is selected from hydrogen, C$_1$-C$_3$alkoxy, C$_1$-C$_3$alkyl, cyano, and halo;
R$^4$ is selected from C$_3$-C$_6$alkyl optionally substituted with one group selected from amino, haloalkyloxy, hydroxy and oxo; and C$_3$-C$_6$cycloalkylC$_1$-C$_3$alkyl optionally substituted with amino;
R$^5$ is selected from hydrogen, C$_1$-C$_6$alkyl, amido, cyano, and halo;
when ⇌ is a double bond, R$^6$ is selected from hydrogen, C$_1$-C$_6$alkoxy, C$_1$-C$_6$alkyl, amido, cyano, C$_1$-C$_6$dialkylamino, halo, hydroxy, and a five-membered heteroaromatic ring; and
when ⇌ is a single bond, R$^6$ is =S.
2. A compound of claim 1 wherein R$^3$ is halo.
3. A compound of claim 1 wherein R$^3$ is hydrogen.
4. A compound of claim 3 wherein R$^2$ is C$_1$-C$_3$alkoxy.
5. A compound of claim 3 wherein R$^2$ is hydrogen.
6. A compound of claim 5 wherein R$^5$ is selected from C$_1$-C$_6$alkyl, amido, cyano, and halo.
7. A compound of claim 5 wherein R$^5$ is hydrogen.
8. A compound selected from
2-Isopentyl-6-(pyridin-4-yl)quinolin-4-ol;
2-Isopentyl-4-methoxy-6-(pyridin-4-yl)quinoline;
4-Bromo-2-isopentyl-6-(pyridin-4-yl)quinoline;
2-Isopentyl-6-(pyridin-4-yl)quinoline;
2-Isopentyl-N,N-dimethyl-6-(pyridin-4-yl)quinolin-4-amine;
2-Isopentyl-6-(pyridin-4-yl)quinoline-4-carbonitrile;
(−)-(R)-2-(1-Amino-3-methylbutyl)-6-(pyridin-4-yl)quinoline-4-carbonitrile;
(+)-(S)-2-(1-Amino-3-methylbutyl)-6-(pyridin-4-yl)quinoline-4-carbonitrile;
2-Isopentyl-7-methoxy-6-(oxazol-5-yl)quinolin-4-ol;
5-(4-Bromo-2-isopentyl-7-methoxyquinolin-6-yl)oxazole;
2-Isopentyl-7-methoxy-6-(oxazol-5-yl)quinoline-4-carbonitrile;
2-(1-Amino-3-methylbutyl)-7-methoxy-6-(oxazol-5-yl)quinoline-4-carbonitrile;

(+)-2-(1-Amino-3-methylbutyl)-7-methoxy-6-(oxazol-5-yl)quinoline-4-carbonitrile;
3-Isobutyl-2-methyl-6-(pyridin-4-yl)quinolin-4-ol;
3-Isobutyl-6-(pyridin-4-yl)quinolin-4-ol;
3-Bromo-2-isopentyl-6-(pyridin-4-yl)quinolin-4-ol;
2-Isopentyl-6-(pyridin-4-yl)quinoline-3-carboxamide;
2-Isopentyl-6-(pyridin-4-yl)quinoline-3-carbonitrile;
3-Methyl-1-(6-(pyridin-4-yl)quinolin-2-yl)butan-1-one;
(−)-3-Methyl-1-(6-(pyridin-4-yl)quinolin-2-yl)butan-1-amine;
(+)-3-Methyl-1-(6-(pyridin-4-yl)quinolin-2-yl)butan-1-amine;
(+)-1-(6-(3-methoxypyridin-4-yl)quinolin-2-yl)-3-methylbutan-1-amine;
(−)-1-(6-(3-methoxypyridin-4-yl)quinolin-2-yl)-3-methylbutan-1-amine;
1-(6-(3-methoxypyridin-4-yl)quinolin-2-yl)-3-methylbutan-1-amine;
1-(6-(1H-pyrrolo[2,3-b]pyridin-4-yl)quinolin-2-yl)-3-methylbutan-1-amine;
1-([4,6'-biquinolin]-2'-yl)-3-methylbutan-1-amine;
1(6-(isoquinolin-6-yl)quinolin-2-yl)-3-methylbutan-1-amine;
4-(2-(1-amino-3-methylbutyl)quinolin-6-yl)-N,N-dimethylpyrimidin-2-amine;
4-(2-(1-amino-3-methylbutyl)quinolin-6-yl)pyridin-2-amine;
N-(4-(2-(3-methylbutanoyl)quinolin-6-yl)pyridin-2-yl)acetamide;
2-isopentyl-6-(pyridin-4-yl)quinoline-4(1H)-thione;
2-(3-methyl-1-(2,2,2-trifluoroethoxy)butyl)-6-(pyridin-4-yl)quinoline;
N-(4-(2-(1-amino-3-methylbutyl)quinolin-6-yl)pyridin-2-yl)acetamide;
N-(4-(2-(1-amino-3-methylbutyl)quinolin-6-yl)pyridin-2-yl)-3-fluorobenzamide;
4-(2-(amino(cyclohexyl)methyl)quinolin-6-yl)-N-(prop-1-en-2-yl)pyridin-2-amine;
3-methyl-1-(6-(pyridin-4-yl)-4-(1H-tetrazol-5-yl)quinolin-2-yl)butan-1-amine;
4-(2-(1-amino-3-methylbutyl)quinolin-6-yl)-N-cyclopropylpyridin-2-amine;
2-(amino(cyclohexyl)methyl)-6-(pyridin-4-yl)quinoline-4-carboxamide;
2-(amino(cyclohexyl)methyl)-6-(pyridin-4-yl)quinoline-4-carboxamide;
2-(amino(cyclohexyl)methyl)-6-(pyridin-4-yl)quinoline-4-carbonitrile;
N-(4-(2-(1-amino-3-methylbutyl)quinolin-6-yl)pyridin-2-yl)-4-(trifluoromethyl)benzamide;
1-(4-ethyl-6-(pyridin-4-yl)quinolin-2-yl)-3-methylbutan-1-amine;
2-(1-amino-3-methylbutyl)-8-fluoro-6-(pyridin-4-yl)quinoline-4-carbonitrile;
N-(4-(2-(1-hydroxy-3-methylbutyl)quinolin-6-yl)pyridin-2-yl)acetamide;
N-(2'-(1-amino-3-methylbutyl)-4,6'-biquinolin-2-yl)acetamide;
2'-(1-amino-3-methylbutyl)-4,6'-biquinolin-2-amine;
2'-(1-amino-3-methylbutyl)-4,6'-biquinolin-2-amine; and
1-(6-(2-cyclopropylpyridin-4-yl)quinolin-2-yl)-3-methylbutan-1-amine;

or a pharmaceutically acceptable salt thereof.

9. A composition comprising a pharmaceutically acceptable amount of a compound of claim 1, or a pharmaceutically acceptable salt thereof, and a pharmaceutically acceptable carrier.

10. A method of inhibiting adaptor associated kinase 1 (AAK1) activity, comprising contacting AAK1 with a compound of claim 1, or a pharmaceutically acceptable salt thereof.

\* \* \* \* \*

UNITED STATES PATENT AND TRADEMARK OFFICE
CERTIFICATE OF CORRECTION

PATENT NO. : 9,932,320 B2  
APPLICATION NO. : 15/112294  
DATED : April 3, 2018  
INVENTOR(S) : Hartz et al.

Page 1 of 1

It is certified that error appears in the above-identified patent and that said Letters Patent is hereby corrected as shown below:

On the Title Page

Column 2, Line 2, item (57), Abstract:  
Delete "AAKI" and insert -- AAK1 --.

Column 2, Line 4, item (57), Abstract:  
Delete "AAKI." and insert -- AAK1. --.

In the Claims

Claim 8, Column 103, Line 22:  
Delete "1(6" and insert -- 1-(6 --.

Signed and Sealed this  
Eleventh Day of December, 2018

Andrei Iancu  
*Director of the United States Patent and Trademark Office*